United States Patent
Halili, Jr. et al.

(10) Patent No.: US 8,636,689 B2
(45) Date of Patent: Jan. 28, 2014

(54) PEN INJECTION DEVICE AND METHOD OF USING SAME

(75) Inventors: Reynaldo B. Halili, Jr., San Diego, CA (US); Victor Wei-Chung Chang, San Diego, CA (US); Phillip A. Estepa, San Diego, CA (US); Tyler J. Holschlag, Encinitas, CA (US); Philip J. Simpson, Encinitas, CA (US); David G. Matsuura, Encinitas, CA (US)

(73) Assignees: Amylin Pharmaceuticals, LLC, San Diego, CA (US); Astrazeneca Pharmaceuticals LP, Wilmington, DE (US)

(*) Notice: Subject to any disclaimer, the term of this patent is extended or adjusted under 35 U.S.C. 154(b) by 536 days.

(21) Appl. No.: 12/669,255

(22) PCT Filed: Jul. 16, 2008

(86) PCT No.: PCT/US2008/070172
§ 371 (c)(1),
(2), (4) Date: Jun. 30, 2010

(87) PCT Pub. No.: WO2009/014955
PCT Pub. Date: Jan. 29, 2009

(65) Prior Publication Data
US 2010/0298768 A1    Nov. 25, 2010

Related U.S. Application Data

(60) Provisional application No. 60/951,179, filed on Jul. 20, 2007.

(51) Int. Cl.
*A61M 37/00*    (2006.01)

(52) U.S. Cl.
USPC ................................................. 604/88

(58) Field of Classification Search
USPC ......... 604/82–92, 403, 411, 68–70, 232, 191, 604/131–139
See application file for complete search history.

(56) References Cited

U.S. PATENT DOCUMENTS

| | | | |
|---|---|---|---|
| 4,227,528 A | 10/1980 | Wardlaw | |
| 4,994,029 A | * 2/1991 | Rohrbough | ............ 604/88 |
| 6,062,722 A | 5/2000 | Lake | |

(Continued)

FOREIGN PATENT DOCUMENTS

| WO | WO 01/52917 | 7/2001 |
|---|---|---|
| WO | WO 2007075677 | * 7/2007 |

*Primary Examiner* — Matthew F Desanto
(74) *Attorney, Agent, or Firm* — Womble Carlyle Sandridge & Rice, LLP; Mark Pino; Alireza Behrooz

(57) ABSTRACT

Pen injection devices (10) and methods of using a pen injection device are disclosed. Pen injection devices include a sterile dual transfer spike assembly (150) including a dual transfer spike defining a fluidic pathway; a first cartridge assembly (12) including a first cartridge (20) containing a first substance; a second cartridge assembly (14) including a second cartridge (30) containing a second substance; a plunger rod (50) translatable in a first direction; and a biasing mechanism (60) configured to bias the plunger rod in a second direction opposite the first direction. Methods of using a pen injection device having a first container, a second container, a plunger rod, and a biasing mechanism include activating the pen injection device, thereby creating a fluidic pathway between the first container and the second container; and translating the plunger rod at least once, thereby transferring a first substance from one container to the other container to mix with a second substance.

20 Claims, 40 Drawing Sheets

(56) References Cited

U.S. PATENT DOCUMENTS

| | | | |
|---|---|---|---|
| 7,341,575 B2 * | 3/2008 | Rice et al. | 604/232 |
| 7,963,954 B2 * | 6/2011 | Kavazov | 604/403 |
| 7,988,660 B2 * | 8/2011 | Byland et al. | 604/70 |
| 2002/0101785 A1 | 8/2002 | Edwards | |

* cited by examiner

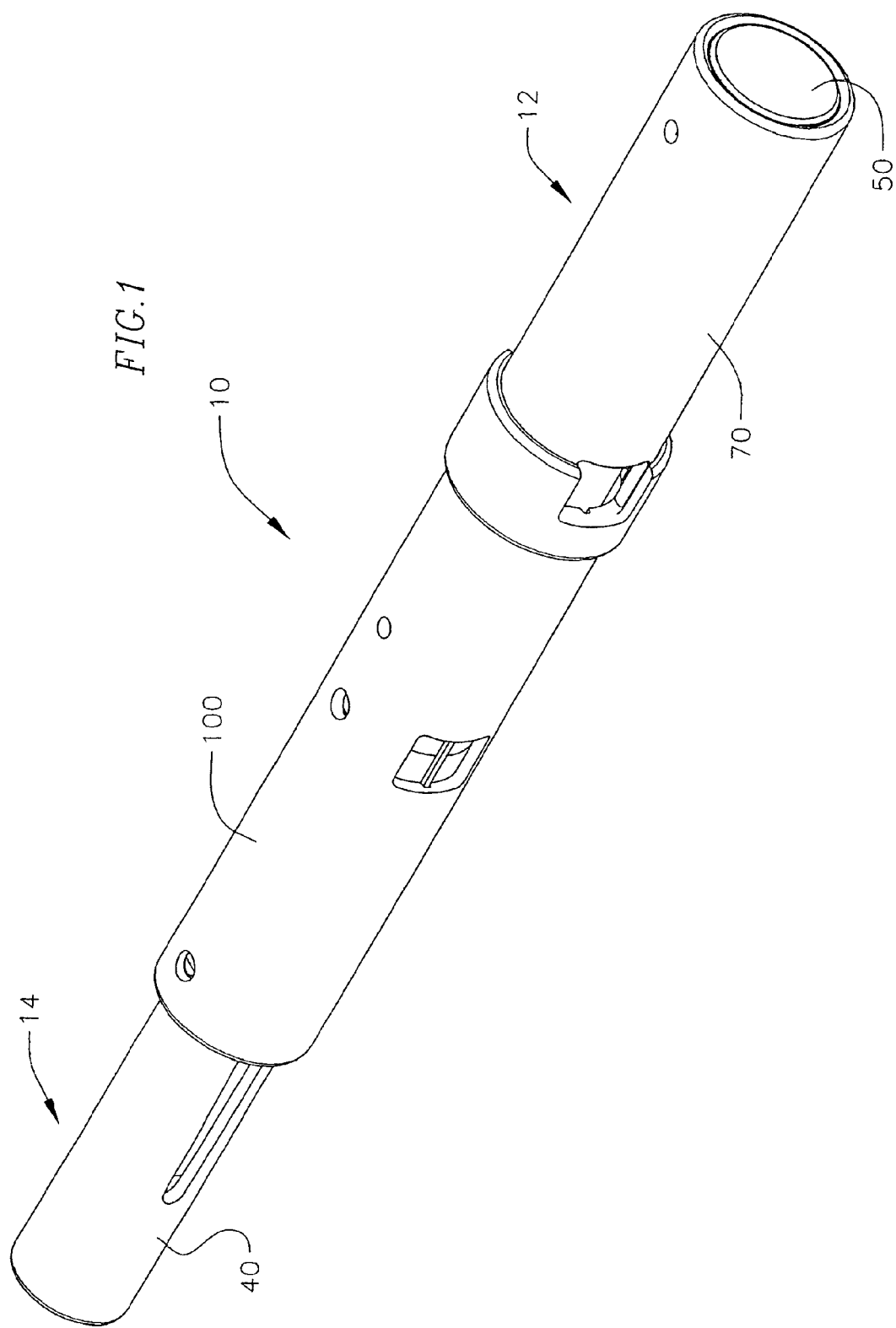

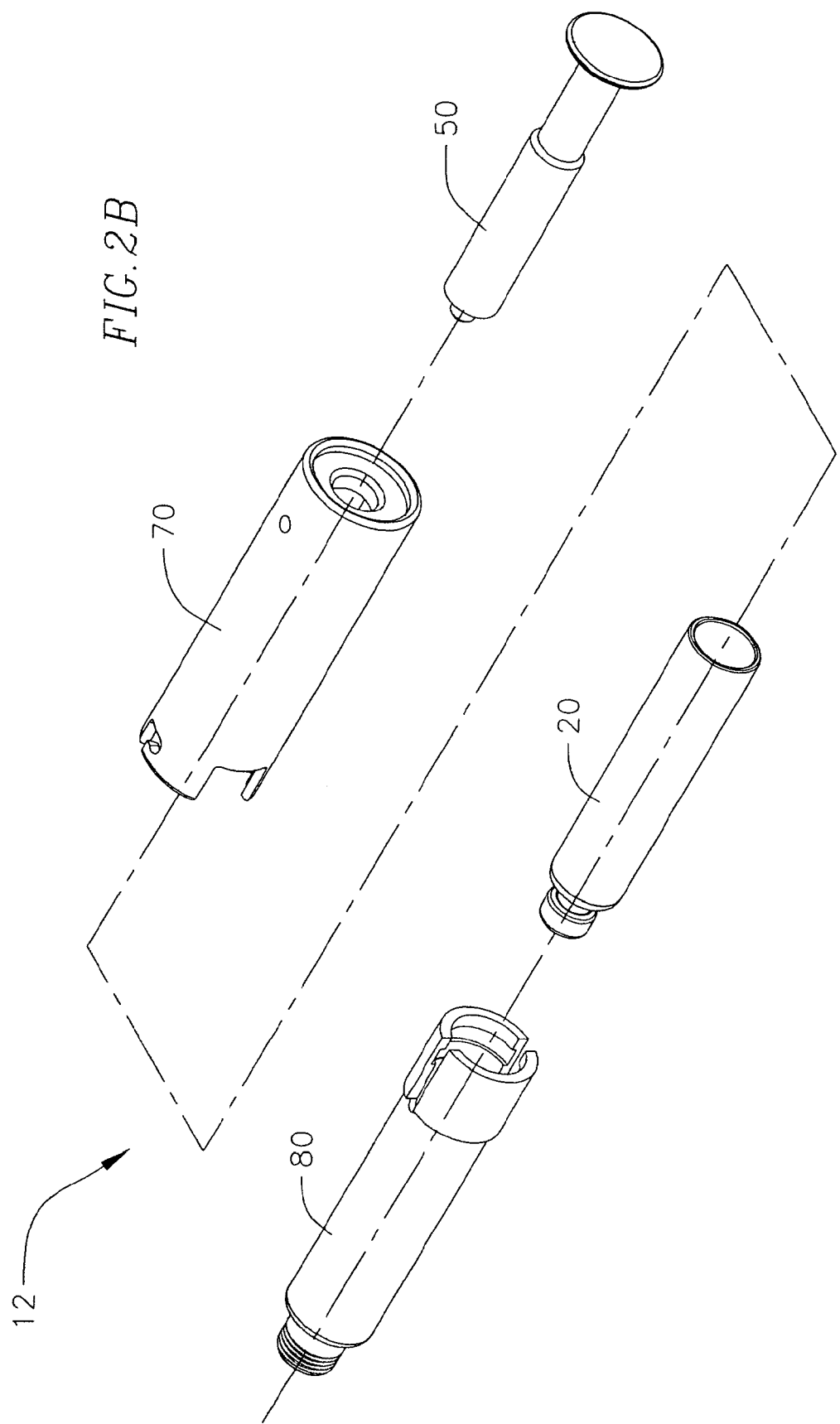

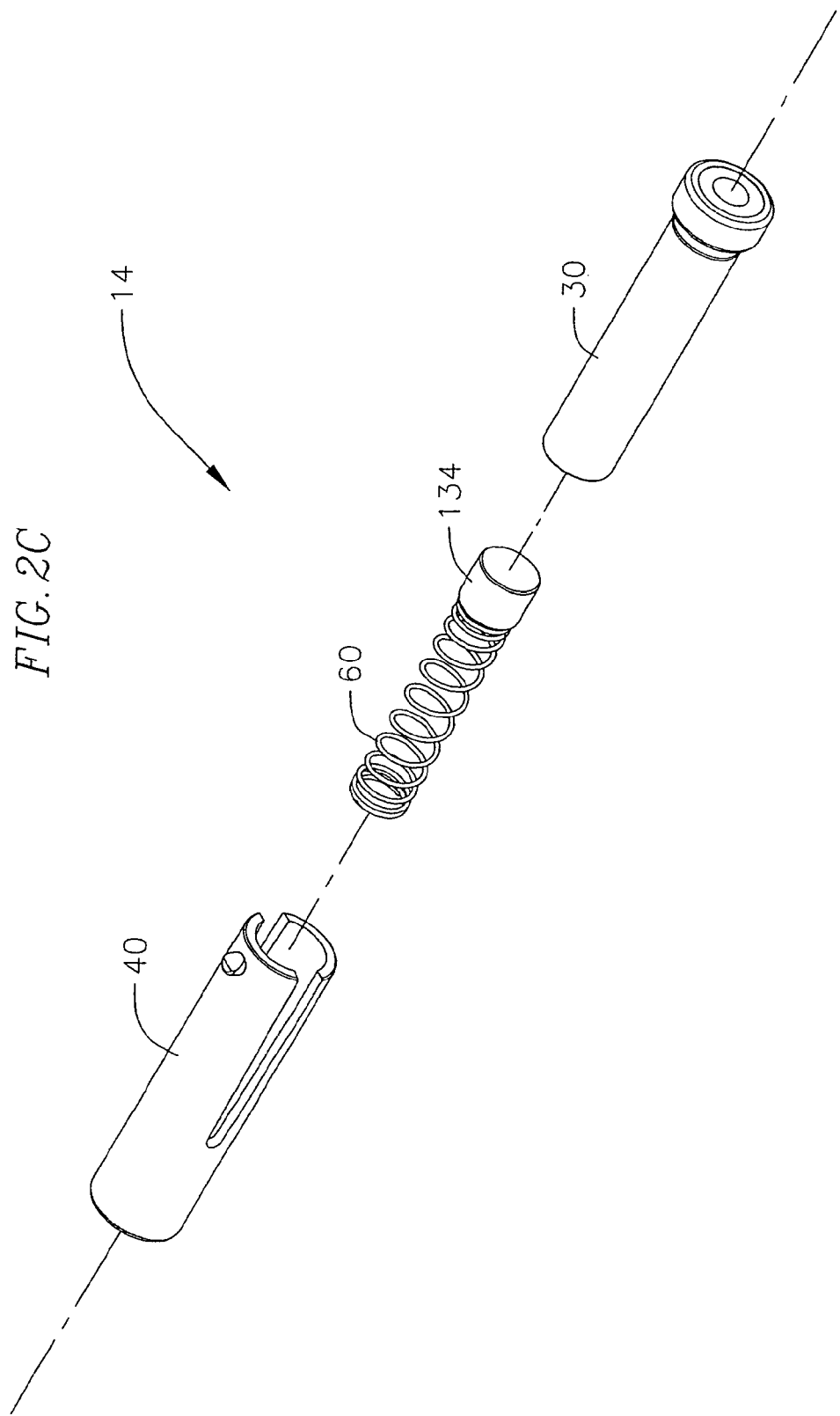

FIG.4A
FIG.4B
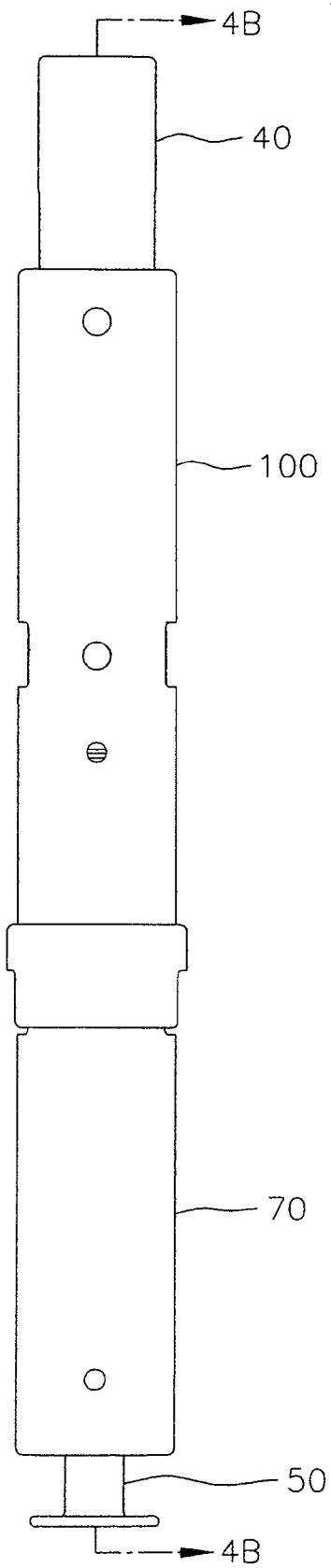
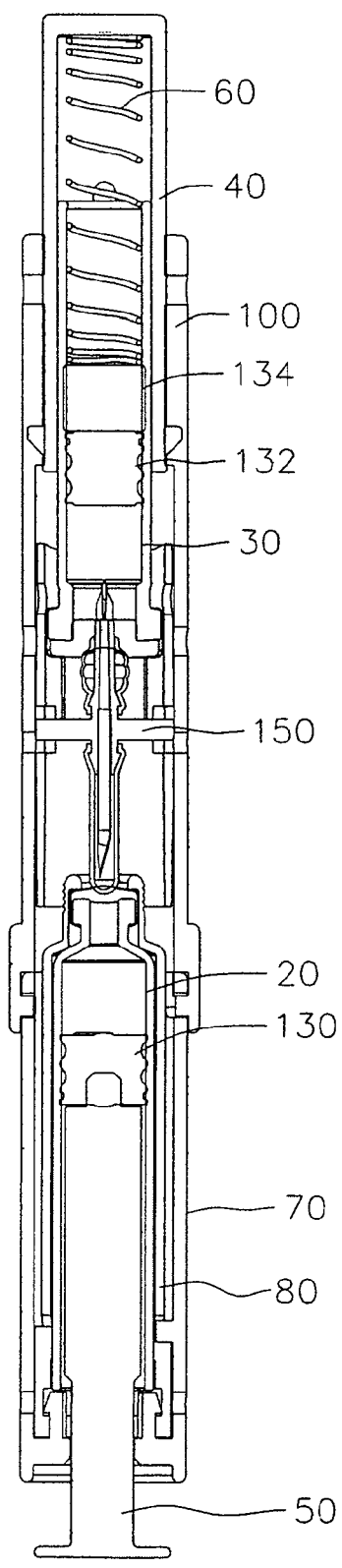

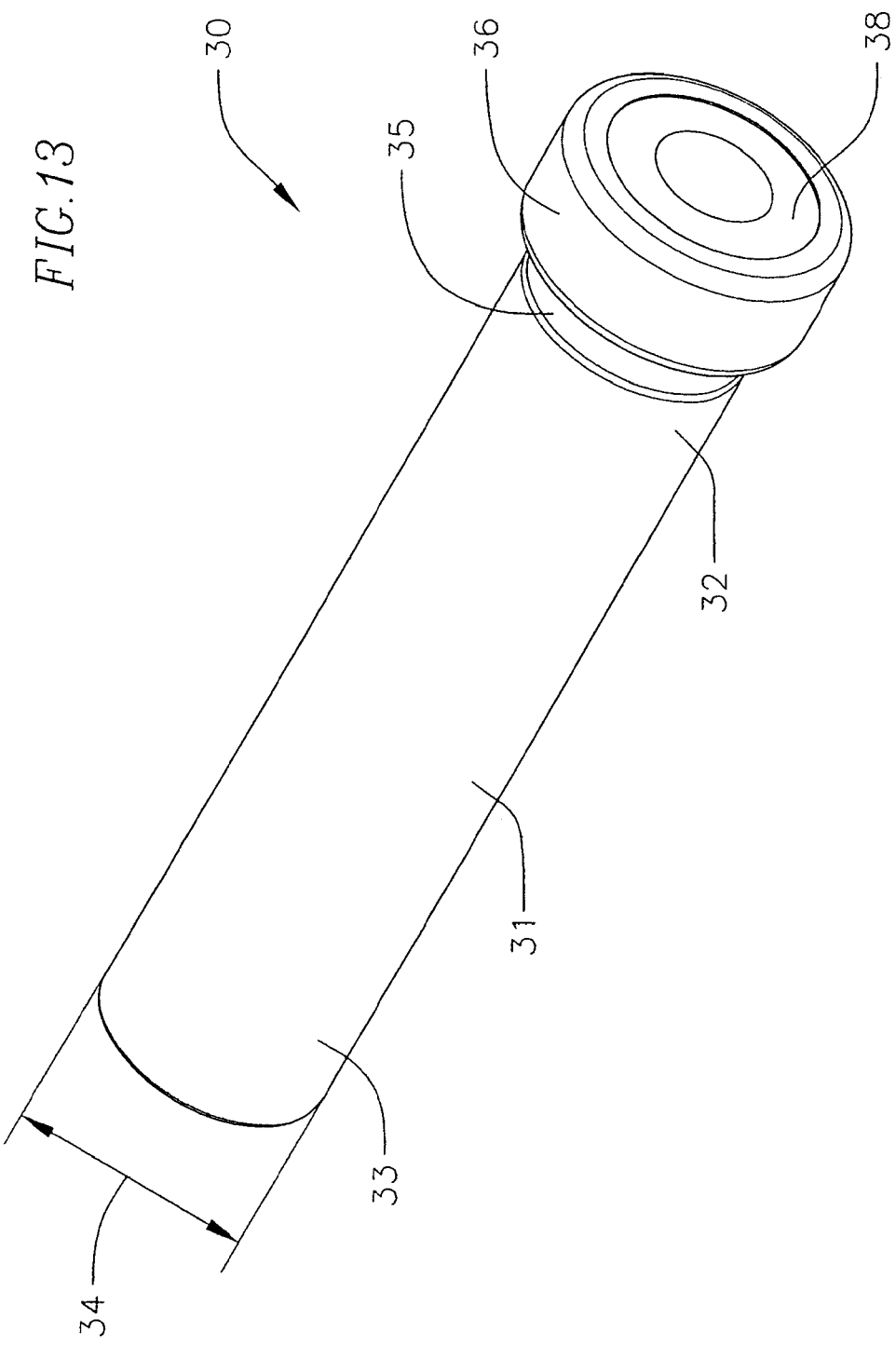

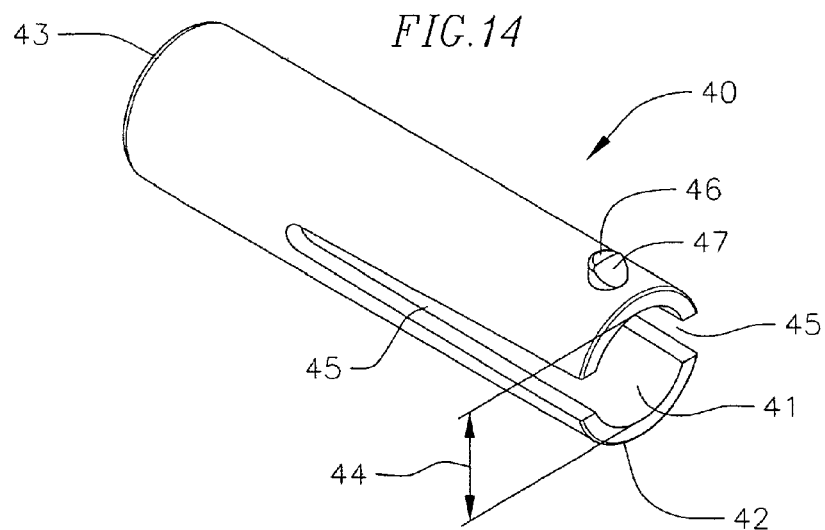
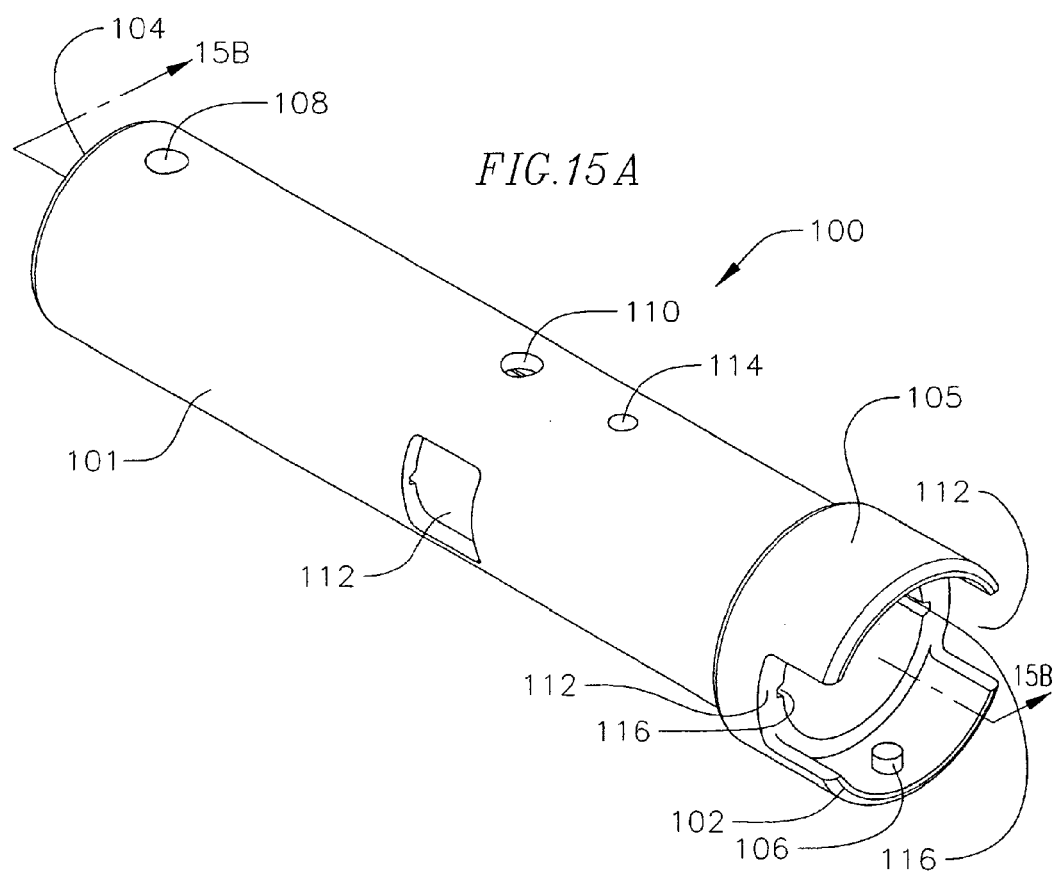

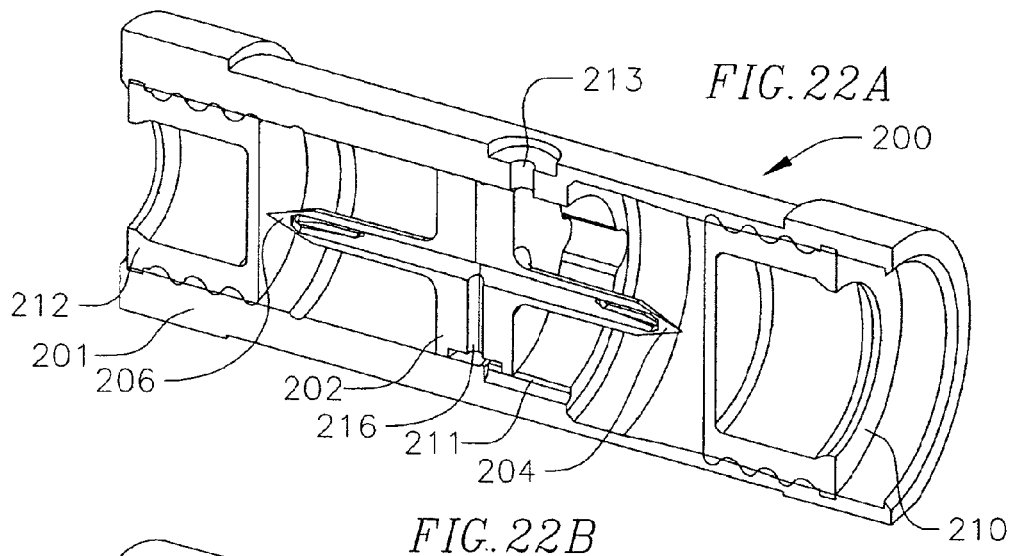
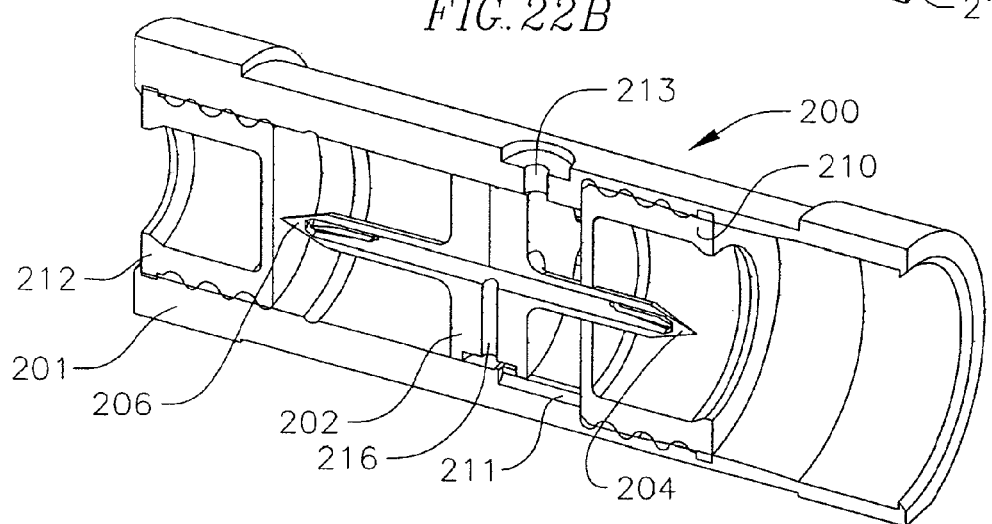
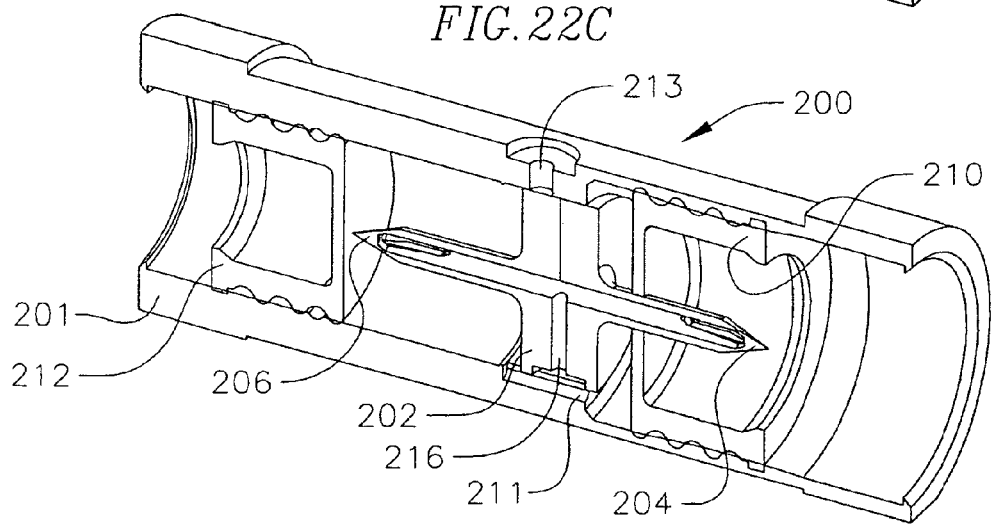

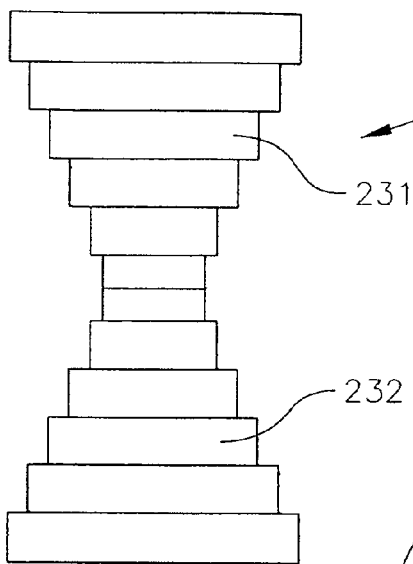
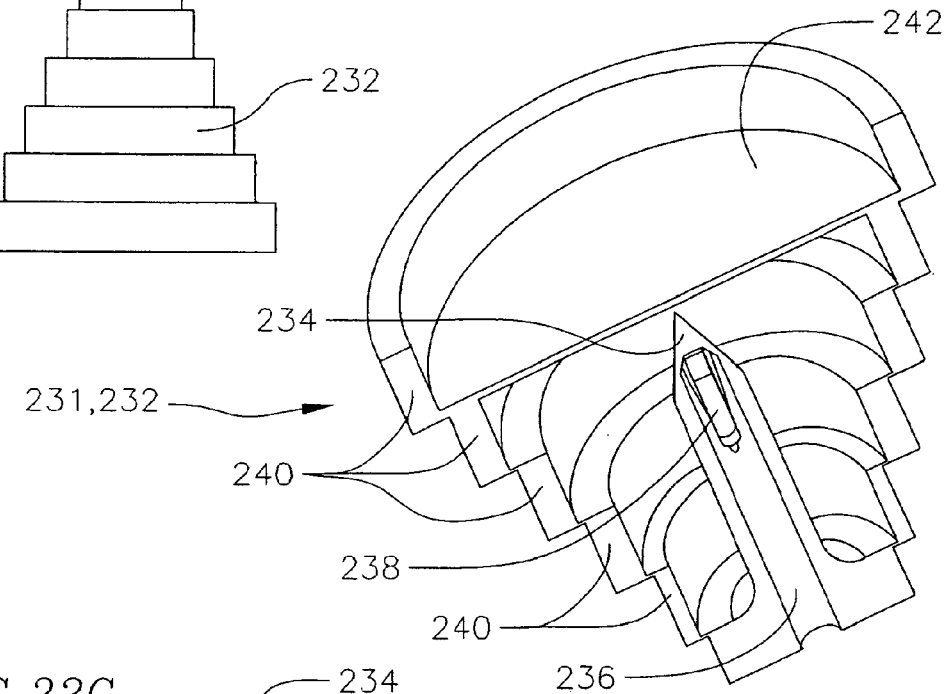
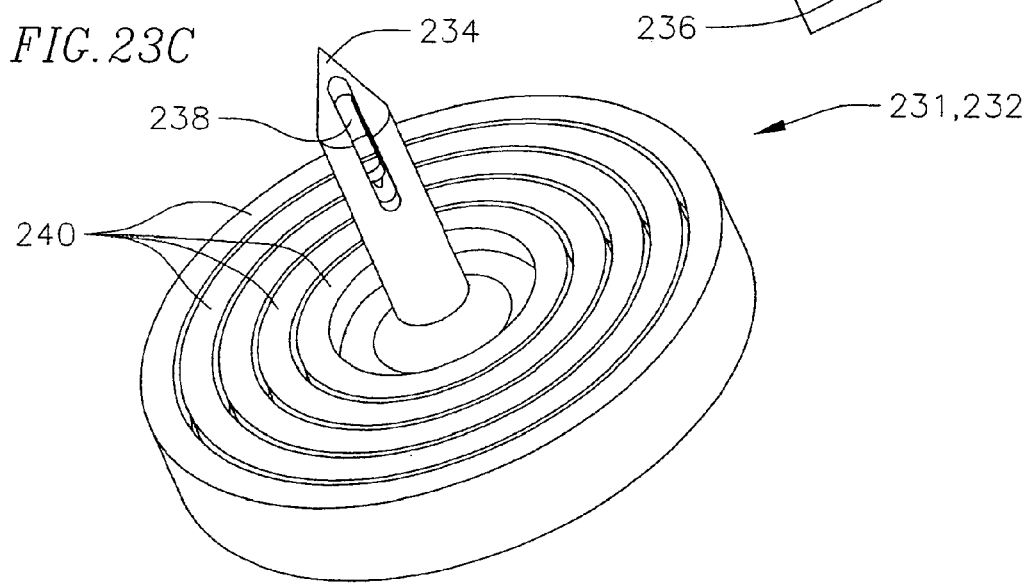

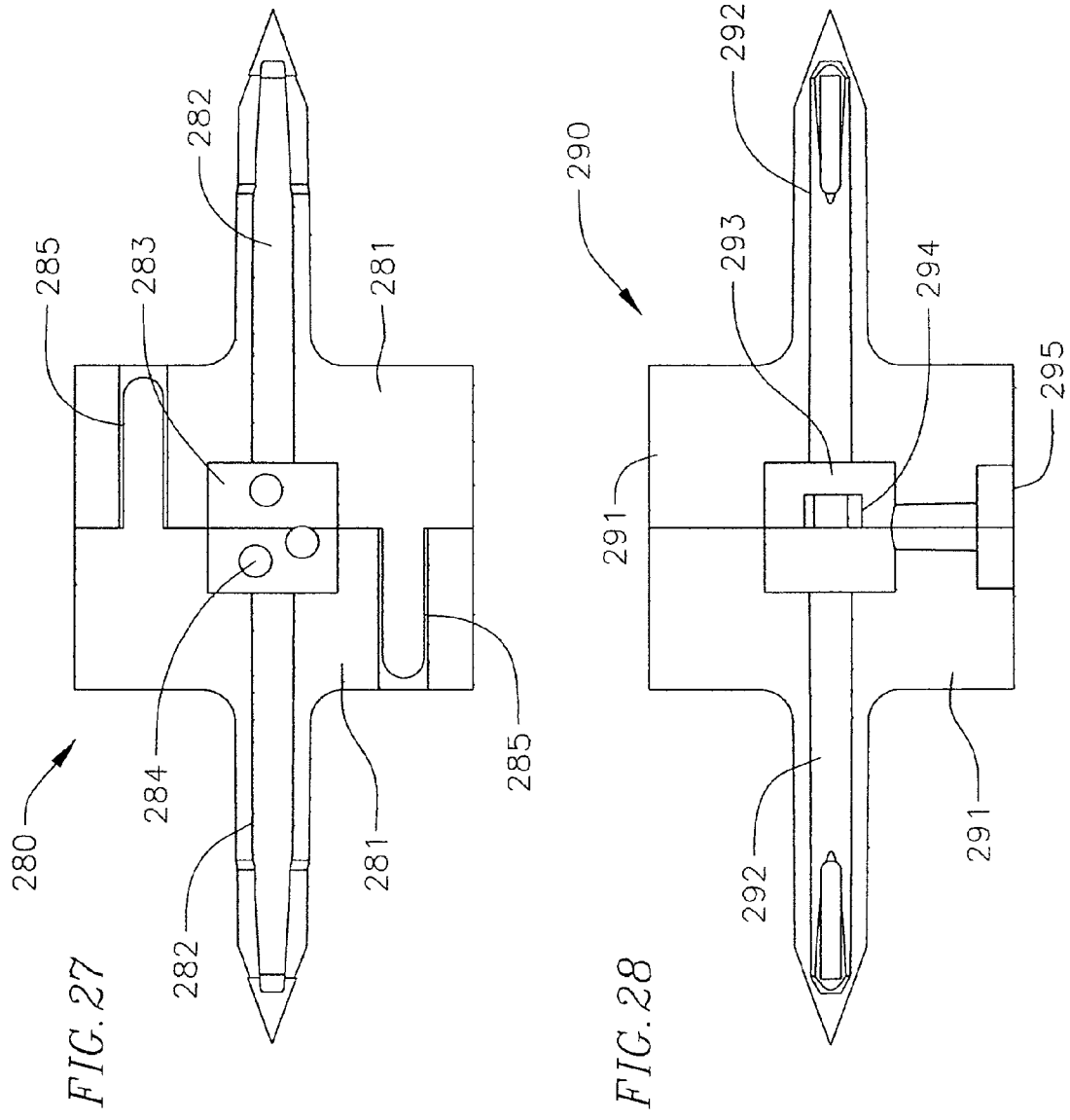

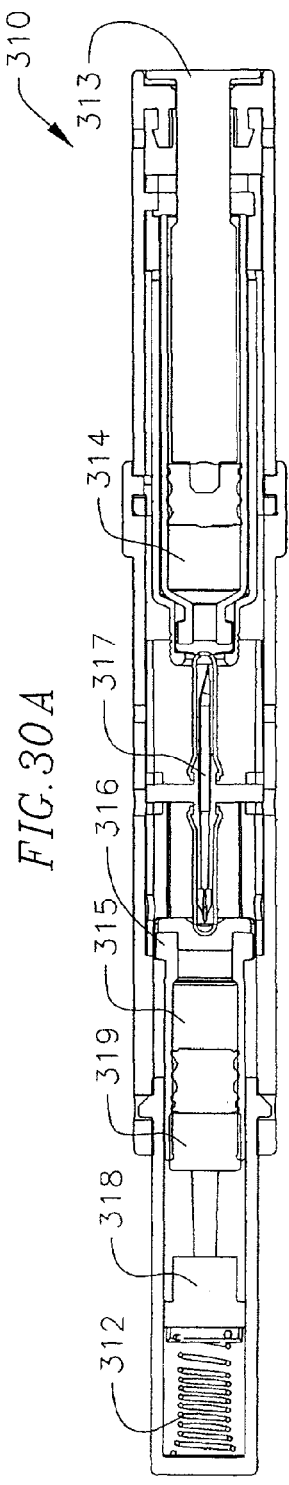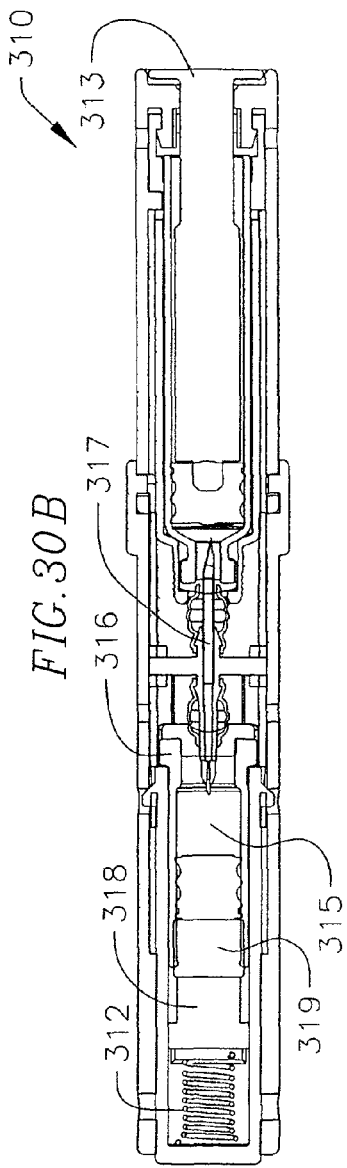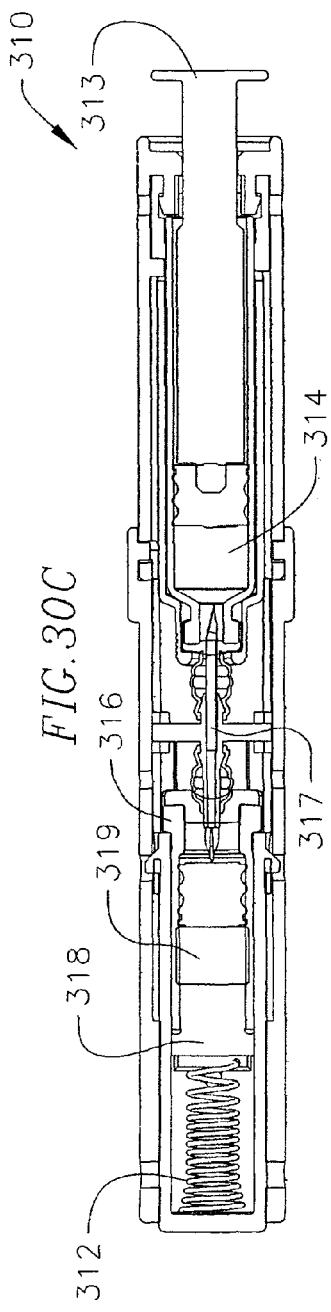

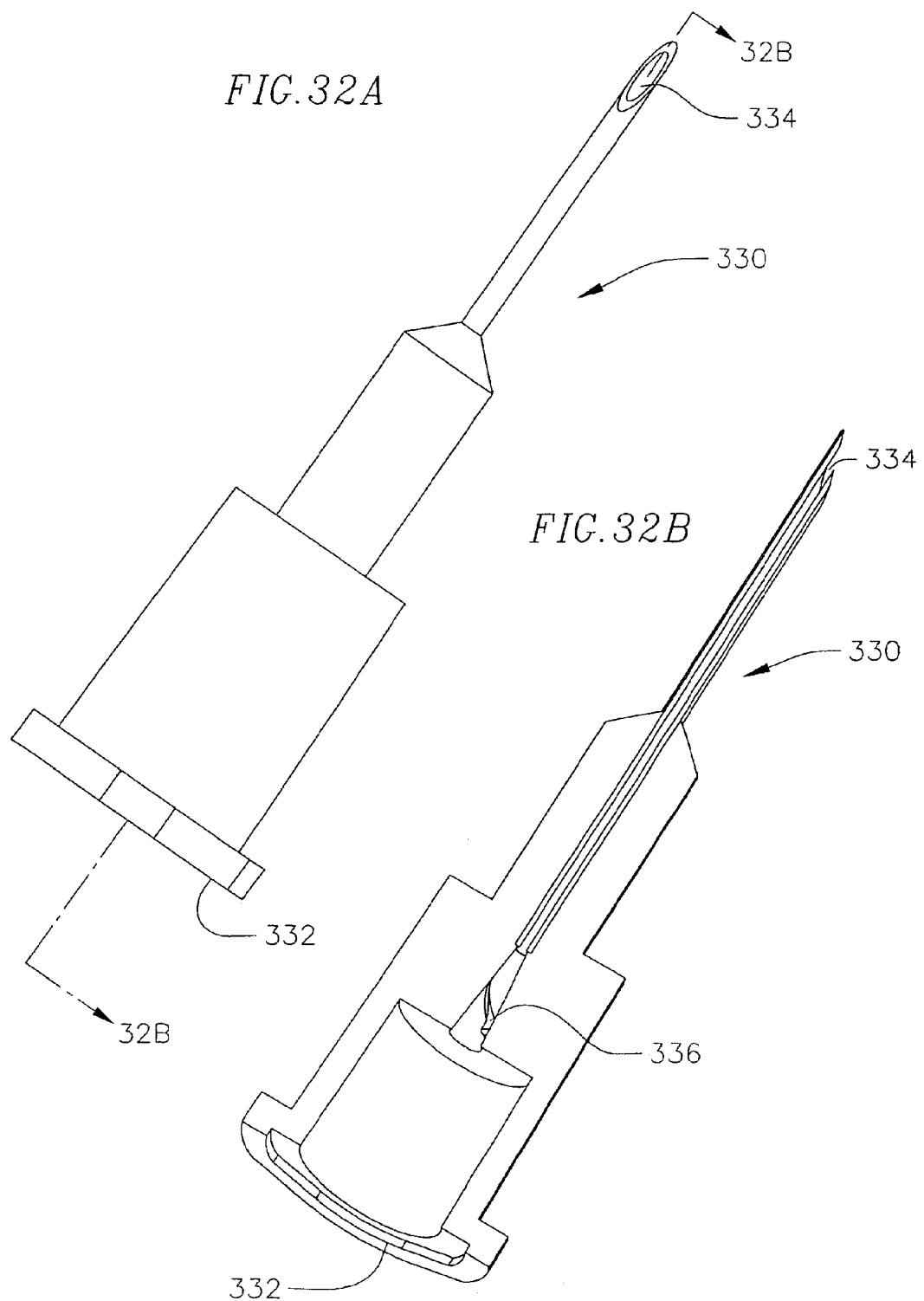

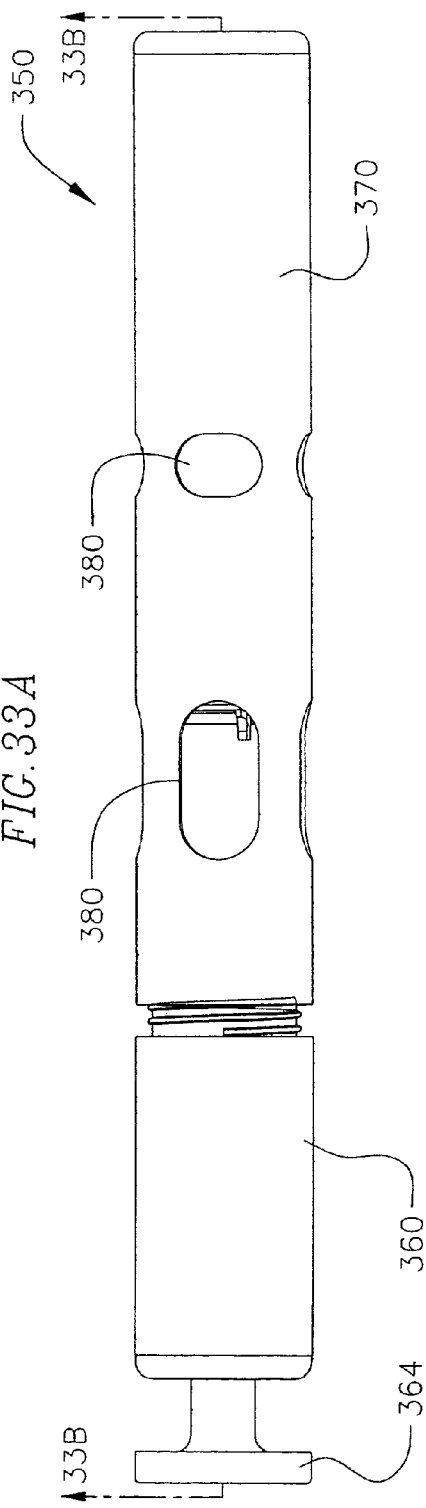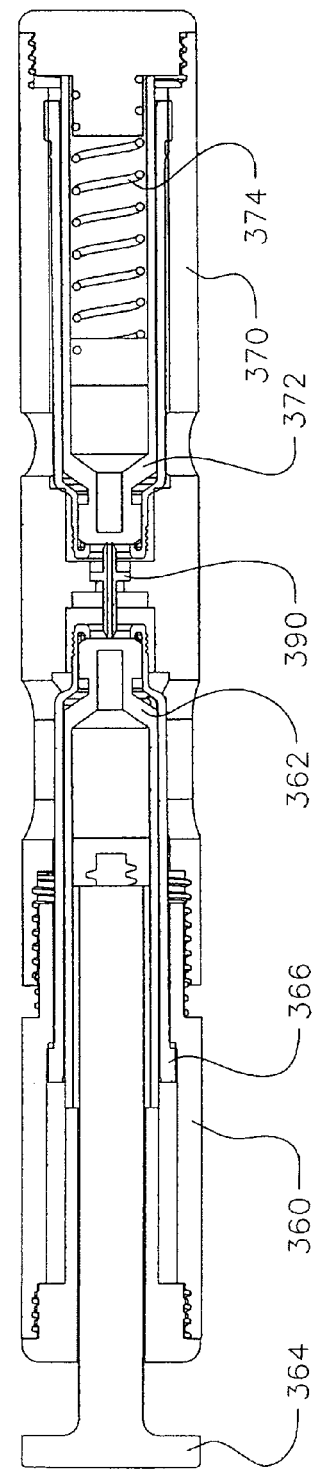

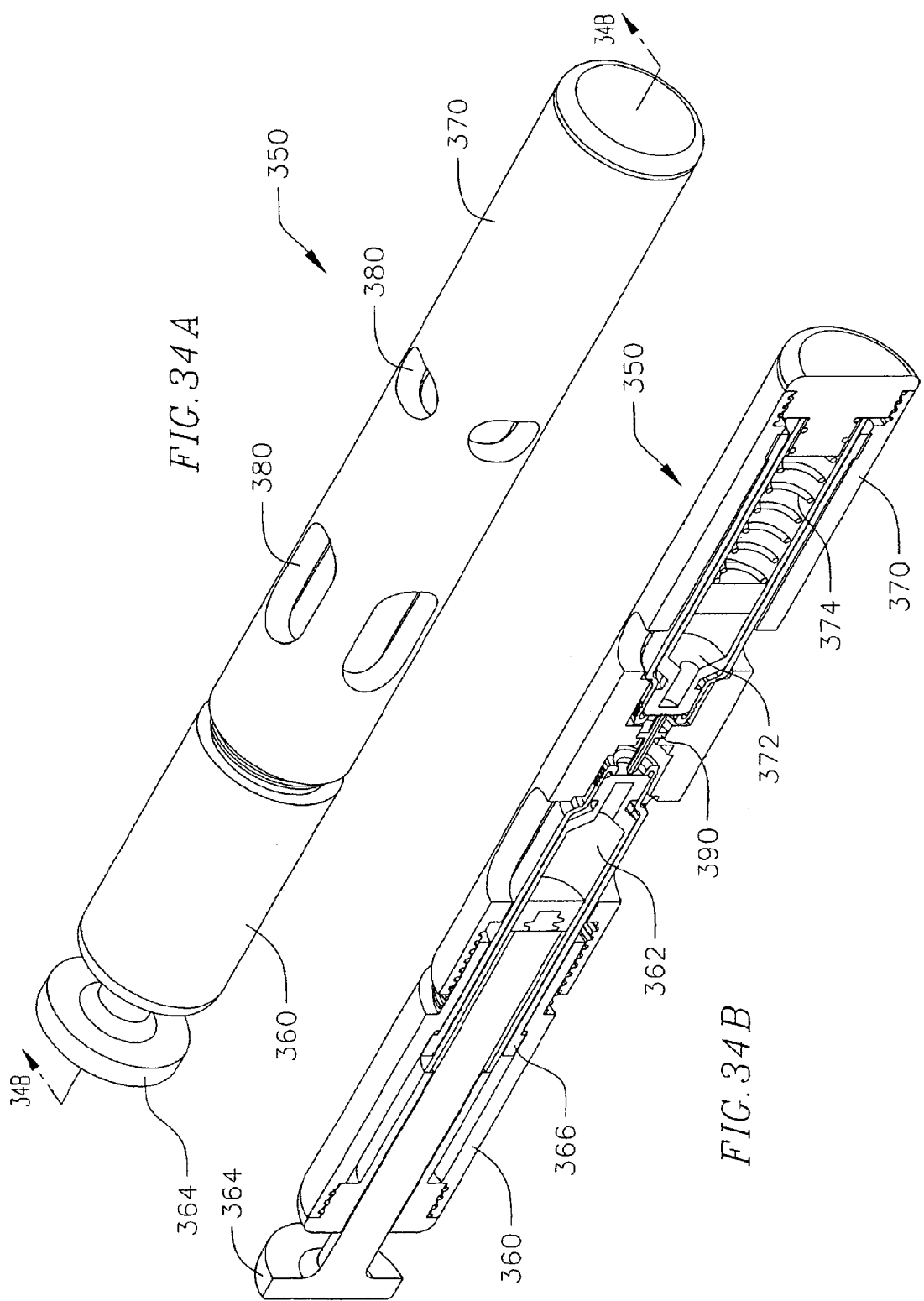

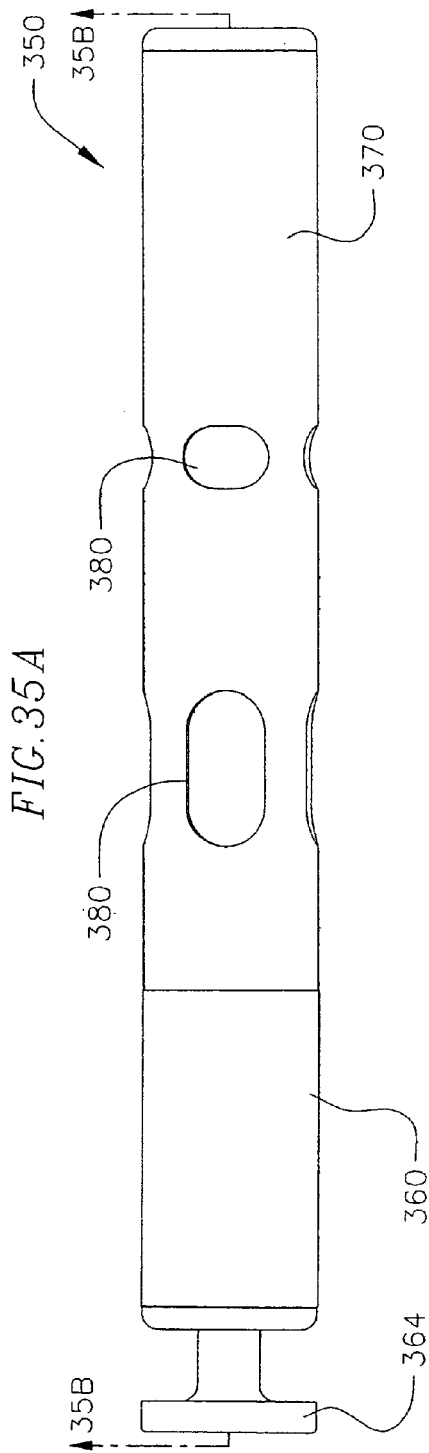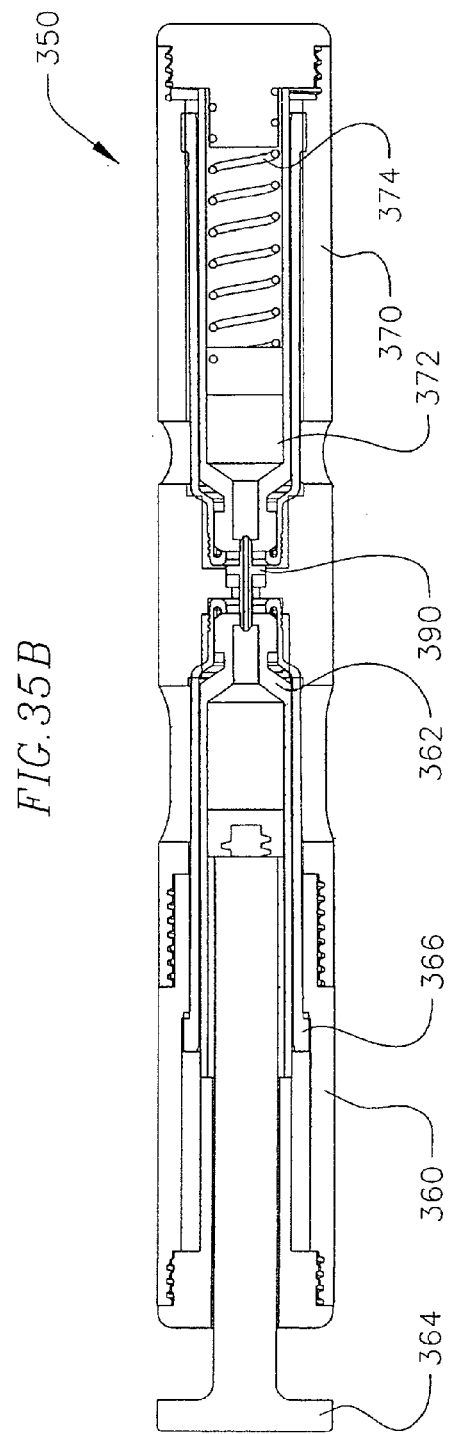

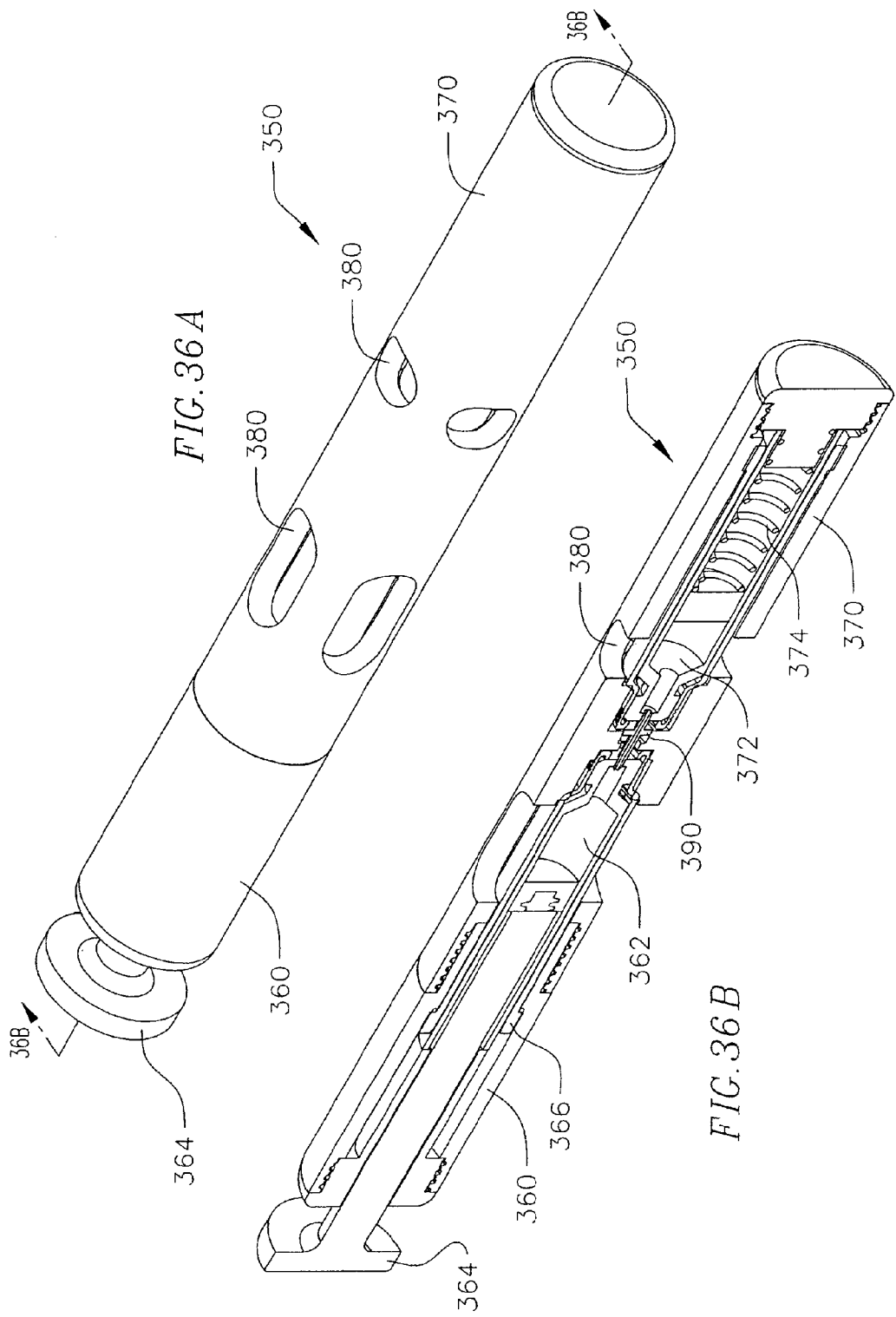

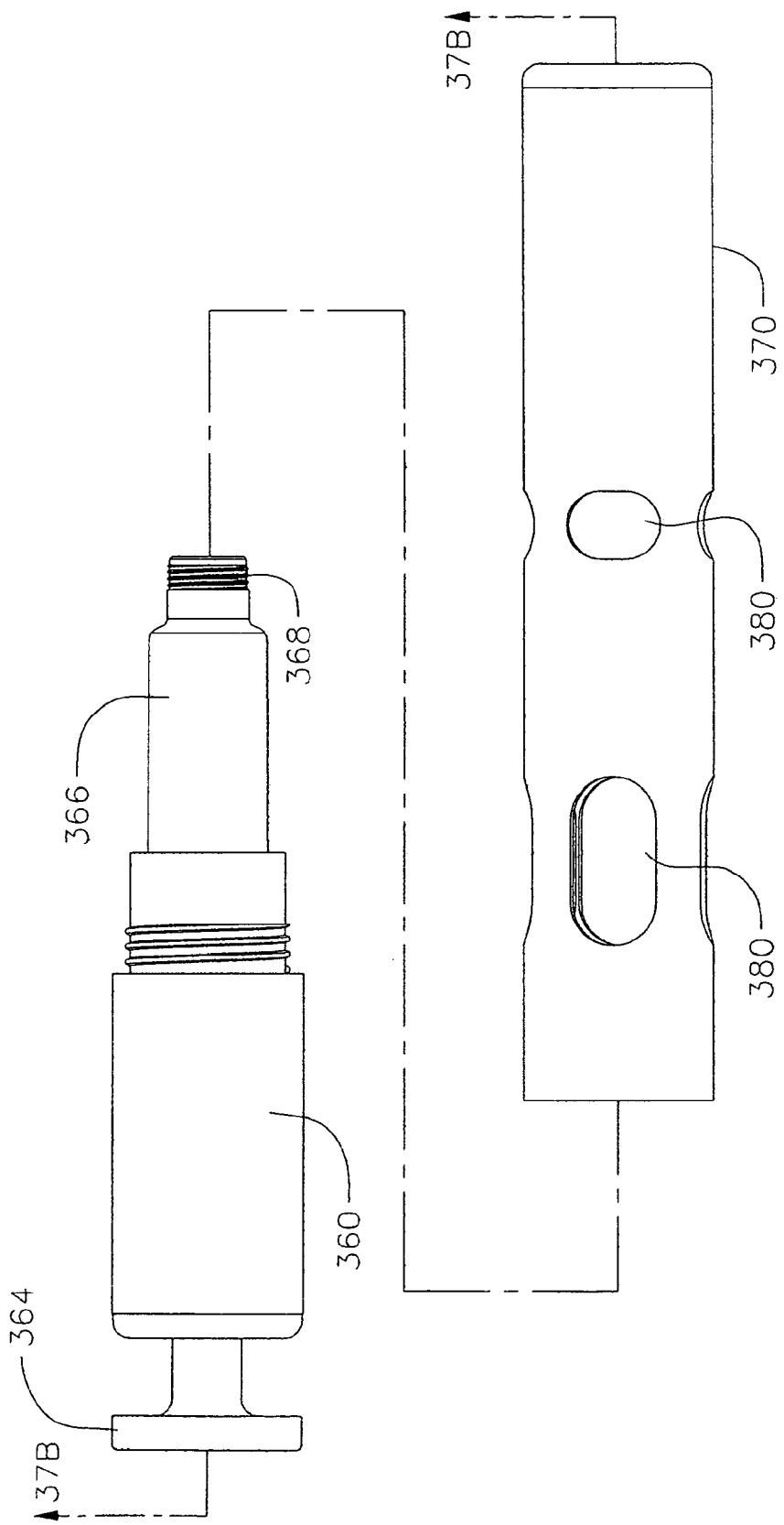

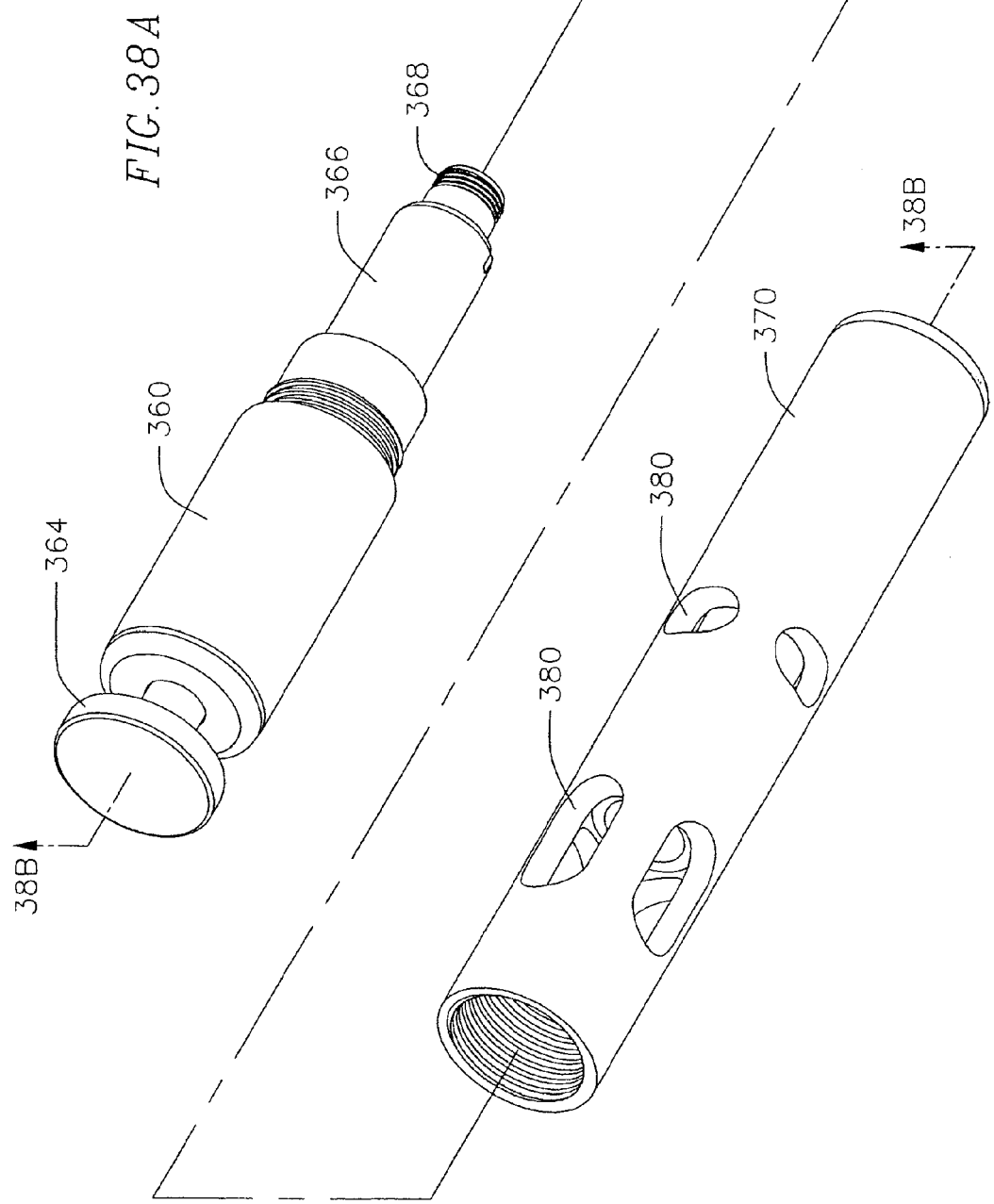

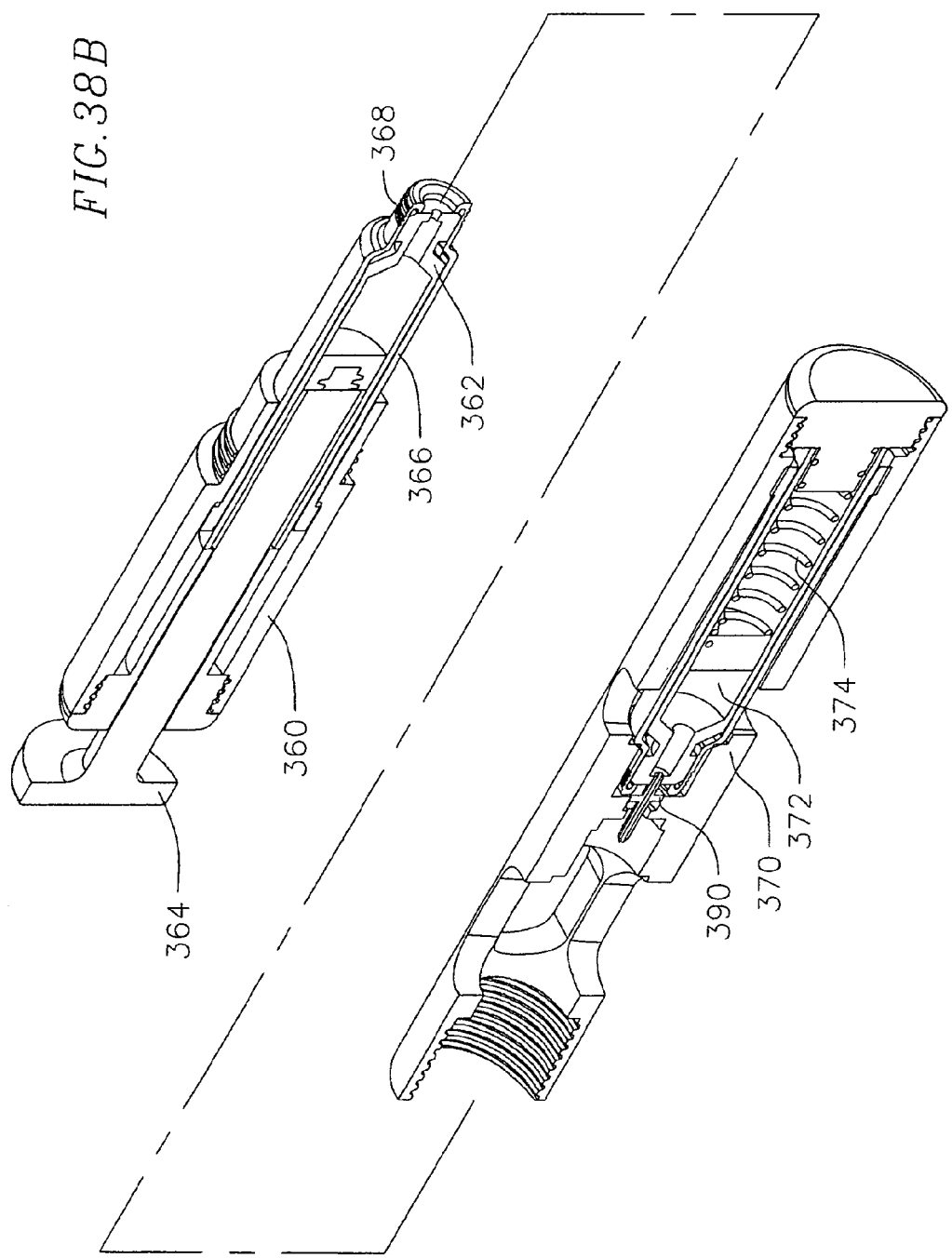

PEN INJECTION DEVICE AND METHOD OF USING SAME

CROSS-REFERENCE TO RELATED APPLICATION(S)

This application claims priority to and the benefit of U.S. Provisional Application No. 60/951,179, filed on Jul. 20, 2007, the entire content of which is incorporated herein by reference.

TECHNICAL FIELD

The present invention relates to injection devices, and more particularly to pen injection devices for mixing and self-injecting a medication and methods of using the same.

BACKGROUND ART

It is common for medical patients to self-inject medicines. For reasons of convenience and/or reduction of cost, patients generally desire that they be able to inject or otherwise administer medicines to themselves or others in their homes, offices, or other locations besides a doctor's office, clinic, hospital, or other medical facility that may be inconvenient and/or expensive to visit. However, some medicines, including those which may be self-injected, are a mixture, suspension, or other combination of two substances. Furthermore, often such medicines must be injected immediately or shortly after the two substances are combined. In some cases, one of the two substances is a diluent and the other is a powder, microspheres, or similar substance. In other cases, each of the two substances to be combined is a liquid.

There are existing devices for combining two substances for self-injection. U.S. Patent Publication No. 2005/0113747 to Moir discloses a device having two tubular bodies, two chambers configured to communicate with each other, and a double-ended needle held in position by a guide member. The double-ended needle is between the two chambers such that when the two tubular bodies are slid toward each other, the respective ends of the needle pass into the two chambers.

Another existing device is disclosed in U.S. Pat. No. 7,077,835 to Robinson et al. This patent discloses a device configured to reconstitute a liquid for medical use by combining a first liquid medium contained in a first vessel and a second medium, such as a drug in solid form, contained in a second vessel. The device further includes a movable member for applying a force to cause the first liquid medium to be delivered at a controlled rate from the first vessel to the second vessel. The device is further configured to receive a needle for transferring the liquid from the device.

SUMMARY OF THE INVENTION

Aspects of embodiments of the present invention are directed toward pen injection devices for injecting a mixture into a subject. The pen injection devices of the present invention may be used for self-injection or injection into another of a medicine, wherein such medicine consists of a mixture, suspension, or other combination of two substances. Another aspect of embodiments of the present invention is a pen injection device configured to allow a user to sufficiently mix two substances to form a mixture or suspension by combining a diluent and a powder, microspheres, or similar substance, wherein the combining is performed just prior to injection. Another aspect of embodiments of the present invention is a pen injection device adapted to mix two separate liquids that are combined just prior to injection. Another aspect of embodiments of the present invention is a pen injection device that is shippable to a user properly aligned and ready for actuation, such that the user is not required to assemble any components of the device. Another aspect of embodiments of the present invention is a pen injection device having a dual transfer spike for mixing two components, wherein the dual transfer spike remains safely inside the device during and after mixing. Yet another aspect of the present invention is a pen injection device having only one possible sequence of operation, such that the device may be intuitively and simply used. Still another aspect of the present invention is a pen injection device configured to maintain sterility of the two substances and of a fluidic pathway therebetween.

A pen injection device according to an embodiment of the present invention includes: a sterile dual transfer spike assembly including a dual transfer spike having a first open end and a second open end, the dual transfer spike defining a fluidic pathway extending through the dual transfer spike from the first end to the second end; a first cartridge assembly including a first cartridge housing, and a first cartridge containing a first substance inside the first cartridge housing; a second cartridge assembly including a second cartridge housing, and a second cartridge containing a second substance inside the second cartridge housing, wherein the second cartridge housing is movable relative to the first cartridge housing from a first position wherein the first and second cartridges are not in fluid communication through the dual transfer spike to a second position wherein the first and second cartridges are in fluid communication through the dual transfer spike; a plunger rod in the first cartridge, translatable in a first direction to transfer at least a portion of the first and second substances from one of the first and second cartridges to the other of the first and second cartridges via the fluidic pathway between the first cartridge and the second cartridge; and a biasing mechanism configured to bias the plunger rod in a second direction opposite the first direction to transfer at least a portion of the first and second substances from the other of the first and second cartridges to the one of the first and second cartridges.

In one embodiment, the first cartridge housing is removably coupled to the second cartridge housing.

In one embodiment, the first cartridge assembly further includes a first cartridge holder receiving the first cartridge therein, the first cartridge holder is received in the first cartridge housing, and the first cartridge holder is interlocked with the first cartridge housing and not axially movable relative to the first cartridge housing when the second cartridge housing is in the second position.

In one embodiment, a pen injection device further includes an outer housing including a first end receiving the first cartridge assembly, and a second end receiving the second cartridge assembly, wherein the dual transfer spike assembly is slidable in the outer housing between the first cartridge assembly and the second cartridge assembly.

In one embodiment, the first cartridge housing is removably coupled to the outer housing. In one embodiment, the dual transfer spike assembly is retained in the outer housing when the first cartridge housing and the outer housing are uncoupled. In one embodiment, the second cartridge housing is slidable in the outer housing.

In one embodiment, the second cartridge housing is rotatable relative to the first cartridge housing from the first position to the second position.

In one embodiment, the fluidic pathway of the dual transfer spike and contents of the first and second cartridges are sterile before the first and second cartridges are in fluid communication through the dual transfer spike.

In one embodiment, the dual transfer spike assembly further includes a first separating member located at the first end of the dual transfer spike and pierceable by the first end of the dual transfer spike, and a second separating member located at the second end of the dual transfer spike and pierceable by the second end of the dual transfer spike.

In one embodiment, the first separating member of the dual transfer spike assembly includes a first sheath surrounding the first end of the dual transfer spike, and the second separating member of the dual transfer spike assembly includes a second sheath surrounding the second end of the dual transfer spike.

In another embodiment of the invention, a pen injection device includes: a sterile transfer assembly including two open ends and providing a fluidic pathway between the two open ends; a first housing portion receiving a first cartridge containing a first substance therein; a second housing portion receiving a second cartridge containing a second substance therein; and a third housing portion including a first end detachably coupled to the first housing portion and a second end engaging the second housing portion, the second housing portion movable relative to the third housing portion from a first position wherein the first and second cartridges are not in fluid communication through the transfer assembly to a second position wherein the first and second cartridges are in fluid communication through the transfer assembly, wherein the first housing portion is engageable with an injection mechanism for injecting the first and second substances when the first housing portion and the third housing portion are uncoupled.

In one embodiment, the transfer assembly includes: a sterile first transfer housing portion including a first spike; a sterile second transfer housing portion including a second spike; a first sheath surrounding the first spike and pierceable by the first spike; and a second sheath surrounding the second spike and pierceable by the second spike.

In another embodiment of the invention, a pen injection device includes: a sterile dual transfer spike assembly including a dual transfer spike having a first open end and a second open end, the dual transfer spike defining a fluidic pathway extending through the dual transfer spike from the first end to the second end; a first cartridge assembly including a first cartridge housing, and a first cartridge containing a first substance inside the first cartridge housing; a second cartridge assembly including a second cartridge housing, and a second cartridge containing a second substance inside the second cartridge housing, wherein the second cartridge housing is movable relative to the first cartridge housing from a first position wherein the first and second cartridges are not in fluid communication through the dual transfer spike to a second position wherein the first and second cartridges are in fluid communication through the dual transfer spike; a first separating member located at the second end of the dual transfer spike and pierceable by the second end of the dual transfer spike to create a fluidic pathway between the second cartridge and the dual transfer spike; and a second separating member located at the first end of the dual transfer spike and pierceable by the first end of the dual transfer spike after the first separating member is pierced, the second separating member pierceable to create a fluidic pathway between the first cartridge and the dual transfer spike.

In another embodiment of the invention, a sterilizable transfer assembly for a pen injection device includes: a tubular housing having an interior, the housing defining a vent opening for venting air from the interior of the housing; a dual transfer spike including a first end having a first opening, a second end having a second opening, an internal cavity extending from the first opening to the second opening and defining a fluidic pathway therebetween, and a vent channel for venting air from the internal cavity of the dual transfer spike to the interior of the housing, the dual transfer spike axially slidable in the interior of the housing from a first position wherein the vent opening is blocked to a second position wherein the vent opening is open for venting air from the interior of the housing; a first separating member axially slidable in the interior of the housing and pierceable by the first end of the dual transfer spike; and a second separating member axially slidable in the interior of the housing and pierceable by the second end of the dual transfer spike.

In one embodiment, a transfer assembly further includes at least one filter for allowing air to pass therethrough and deterring liquids and solids from passing therethrough and for maintaining sterility in the transfer assembly, the at least one filter covering at least one of the vent opening of the housing and the vent channel of the dual transfer spike.

In one embodiment, the first separating member is axially slidable in the interior of the housing from a first position wherein the first separating member is not pierced to a second position wherein the first separating member is pierced by the first end of the dual transfer spike and a venting path for venting air from a first cartridge is defined by the first opening of the dual transfer spike, the internal cavity of the dual transfer spike, the vent channel of the dual transfer spike, and the vent opening of the housing; and the second separating member is axially slidable in the interior of the housing from a first position wherein the second separating member is not pierced to a second position wherein the second separating member is pierced by the second end of the dual transfer spike and a venting path for venting air from a second cartridge is defined by the second opening of the dual transfer spike, the internal cavity of the dual transfer spike, the vent channel of the dual transfer spike, and the vent opening of the housing.

In still another embodiment of the invention, a method of using a pen injection device having a first container, a second container, a plunger rod, and a biasing mechanism includes: activating the pen injection device, thereby creating a fluidic pathway between the first container and the second container; and translating the plunger rod in a first direction from a first position at least once, thereby transferring at least a portion of a first substance from one of the first and second containers to the other of the first and second containers to mix therein with a second substance, the biasing mechanism thereafter moving at least a portion of the second substance from the other of the first and second containers to the one of the first and second containers.

In one embodiment, a method of using a pen injection device further includes: determining whether the first and second substances are sufficiently mixed by viewing the first and second substances through at least one window of the pen injection device; and if the first and second substances are not sufficiently mixed, translating the plunger rod in the first direction at least once again to further mix the first and second substances.

In one embodiment, a method of using a pen injection device further includes: disconnecting the second container from the first container; connecting an injection needle to the first container; piercing a subject with the injection needle; and depressing the plunger rod toward the first container, thereby injecting a mixture of the first and second substances into the subject.

In one embodiment, activating the pen injection device includes applying an activation force to an activation member of the pen injection device, and translating the plunger rod from an unactivated position to the first position.

In one embodiment, activating the pen injection device includes piercing a first sheath surrounding a first spike end of a transfer assembly, and piercing a second sheath surrounding a second spike end of the transfer assembly.

BRIEF DESCRIPTION OF THE DRAWINGS

These and other features, aspects, and advantages of the present invention will become better understood with regard to the following description, appended claims, and accompanying drawings where:

FIG. 1 is a side perspective view of a pen injection device according to an embodiment of the present invention, the pen injection device in an unactivated state;

FIG. 2B is an exploded side perspective view of a first cartridge assembly of the pen injection device of FIG. 1;

FIG. 2C is an exploded side perspective view of a second cartridge assembly of the pen injection device of FIG. 1;

FIG. 4A is a side view of the pen injection device of FIG. 1, the pen injection device in a first partially activated position;

FIG. 4B is a side sectional view through the pen injection device of FIG. 1 taken at line 4B-4B, the pen injection device in a first partially activated position;

FIG. 13 is a side perspective view of a second cartridge of the pen injection device of FIG. 1;

FIG. 14 is a side perspective view of an activation member of the pen injection device of FIG. 1;

FIG. 15A is a side perspective view of an outer housing of the pen injection device of FIG. 1;

FIGS. 22A-E are perspective sectional views through the dual transfer spike assembly of FIG. 19 showing components in various positions for venting;

FIG. 23A is a side view of a transfer assembly of a pen injection device according to another embodiment of the present invention;

FIG. 23B is a perspective sectional view of a portion of the transfer assembly of FIG. 23A;

FIG. 23C is a perspective view of a portion of the transfer assembly of FIG. 23A;

FIG. 27 is a sectional view through a transfer assembly of a pen injection device according to another embodiment of the present invention;

FIG. 28 is a sectional view through a transfer assembly of a pen injection device according to another embodiment of the present invention;

FIGS. 30A-C are sectional views through a pen injection device according to another embodiment of the present invention, the pen injection device at various stages of activation;

FIG. 32A is a side view of an injection needle of a pen injection device according to another embodiment of the present invention;

FIG. 32B is a side sectional view through the injection needle of FIG. 32A taken at line 32B-32B;

FIG. 33A is a side view of a pen injection device according to another embodiment of the present invention, the pen injection device in an unactivated state;

FIG. 33B is a side sectional view through the pen injection device of FIG. 33A taken at line 33B-33B, the pen injection device in an unactivated state;

FIG. 34A is a side perspective view of the pen injection device of FIG. 33A, the pen injection device in an unactivated state;

FIG. 34B is a perspective sectional view through the pen injection device of FIG. 33A taken at line 34B-34B, the pen injection device in an unactivated state;

FIG. 35A is a side view of the pen injection device of FIG. 33A, the pen injection device in an activated state;

FIG. 35B is a side sectional view through the pen injection device of FIG. 33A taken at line 35B-35B, the pen injection device in an activated state;

FIG. 36A is a side perspective view of the pen injection device of FIG. 33A, the pen injection device in an activated state;

FIG. 36B is a perspective sectional view through the pen injection device of FIG. 33A taken at line 36B-36B, the pen injection device in an activated state;

FIG. 37A is a side view of the pen injection device of FIG. 33A, the pen injection device in an activated state and having a first housing portion disconnected from a second housing portion;

FIG. 38A is a side perspective view of the pen injection device of FIG. 33A, the pen injection device in an activated state and having a first housing portion disconnected from a second housing portion;

FIG. 38B is a perspective sectional view through the pen injection device of FIG. 33A taken at line 38B-38B, the pen injection device in an activated state and having a first housing portion disconnected from a second housing portion.

DETAILED DESCRIPTION

In the following detailed description, certain exemplary embodiments of the present invention are shown and described, by way of illustration. As those skilled in the art would recognize, the described exemplary embodiments may be modified in various ways, all without departing from the spirit or scope of the present invention. Accordingly, the drawings and description are to be regarded as illustrative in nature, rather than restrictive.

Figure 2A:
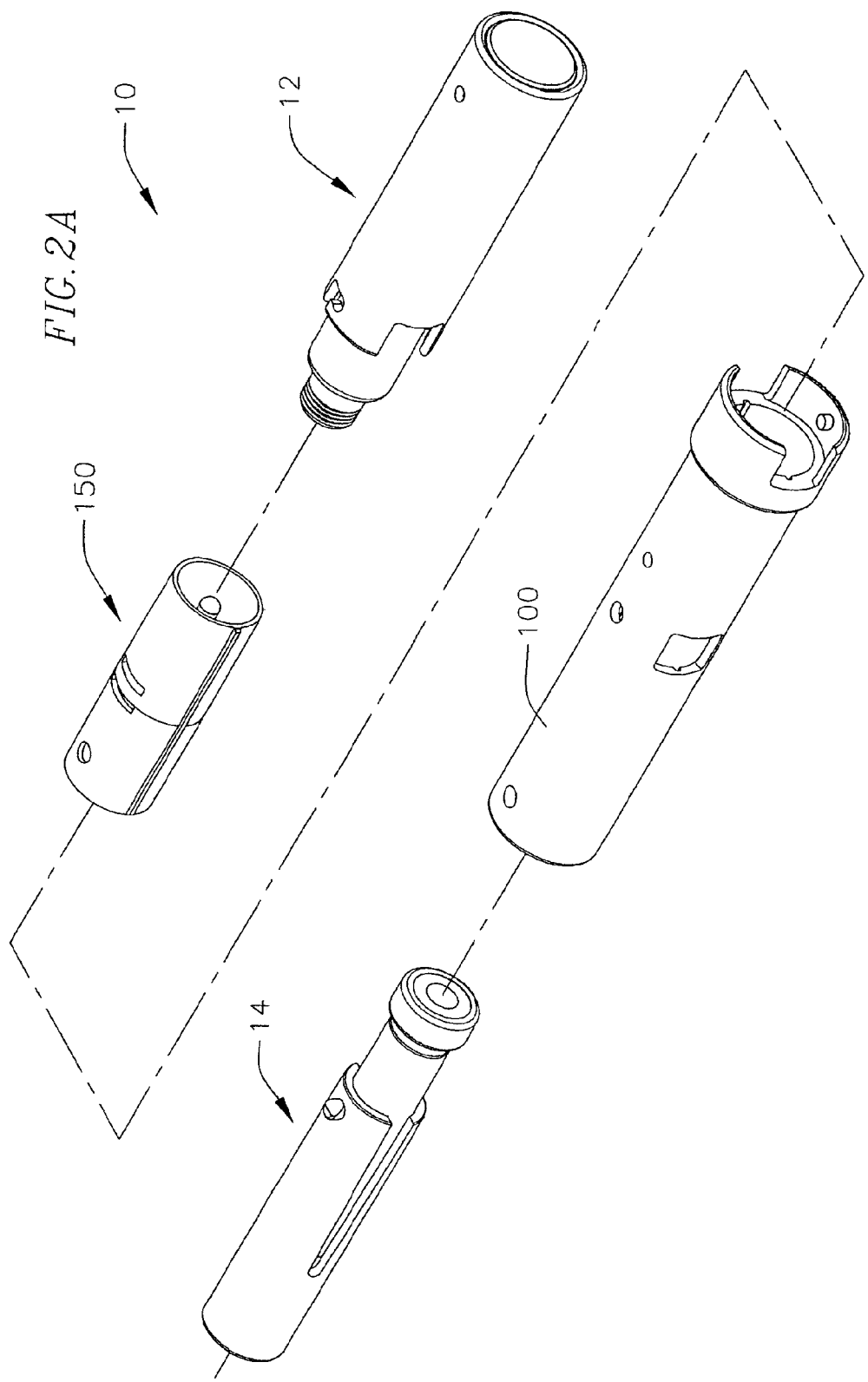
FIG. 2A is a partially exploded side perspective view of the pen injection device of FIG. 1.
Figures 3A, 3B:
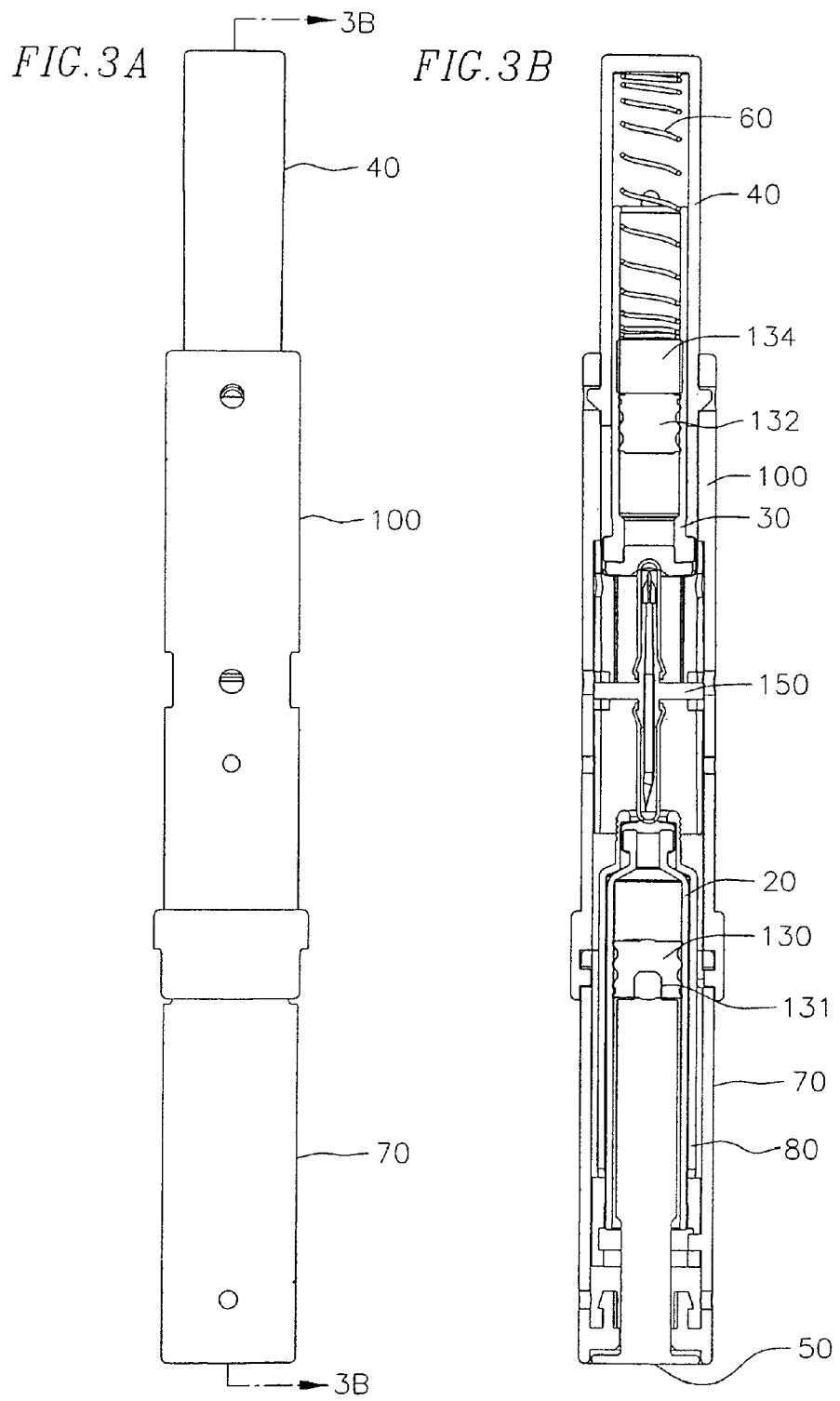
FIG. 3A is a side view of the pen injection device of FIG. 1, the pen injection device in an unactivated state.
FIG. 3B is a side sectional view through the pen injection device of FIG. 1 taken at line 3B-3B, the pen injection device in an unactivated state.

With reference to FIGS. 1 and 2A, a pen injection device 10 is configured to combine a first substance and a second substance, thereby forming a mixture, a suspension, or any other combination of the first and second substances. Each of the first and second substances may be a liquid or solid, such as a diluent, a powder, microspheres, or another similar substance, and is initially contained in an unactivated state. In the unactivated state, as depicted in FIGS. 1 and 3A-B, each of the first and second substances is contained separately, the first substance in a first cartridge 20, and the second substance in a second cartridge 30. When the pen injection device 10 is activated by applying an activation force to an activation member 40, a fluidic pathway is created between the first and second substances. The pen injection device 10 is shown in two stages of partial activation in FIGS. 4A-B and 5A-B, and in a completely activated state in FIGS. 6A-B.

The pen injection device 10 is also configured to thoroughly mix the first and second substances. A desired degree of mixing may be achieved by depressing one or more times, or pumping, a plunger rod 50, shown in a depressed position in FIGS. 7A-B. Such pumping action forces the first substance and/or the mixture from the first cartridge 20 to the second cartridge 30. A biasing mechanism 60 of the pen injection device 10 then causes the mixture to move back to the first cartridge 20, at which point the plunger rod 50 may be depressed again to mix the first and second substances still further.

Figure 8:
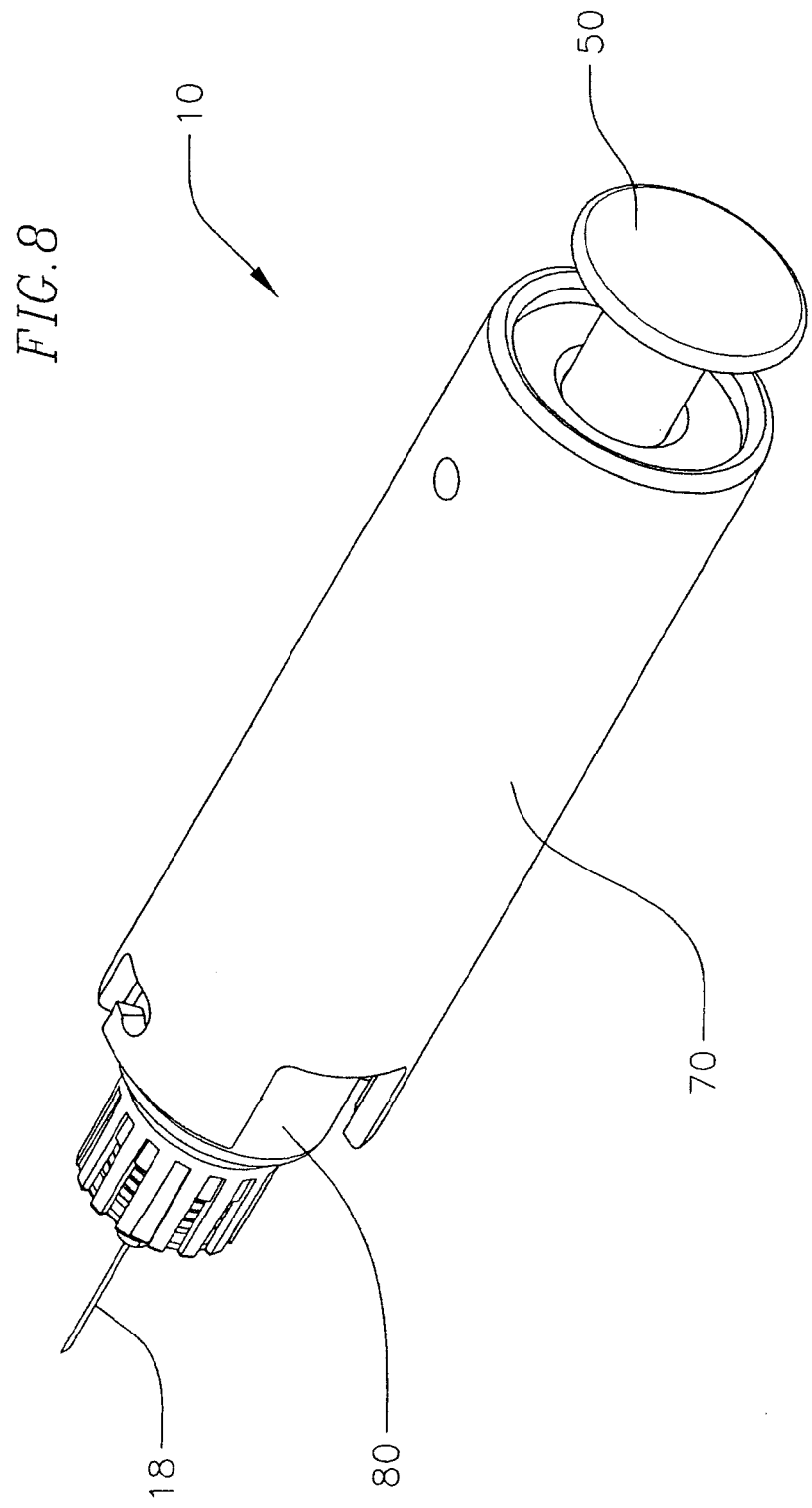
FIG. 8 is a side perspective view of the pen injection device of FIG. 1, the pen injection device in an activated state and having an injection needle connected.

The pen injection device 10 is further configured to inject or otherwise administer the mixture to a subject, such as by self-administration or to another patient. The pen injection device 10 is configured such that an outer housing 100 connecting the second cartridge 30 to the first cartridge 20 may be removed, thereby indirectly disconnecting the second cartridge 30 from the first cartridge 20. The first cartridge 20 is configured such that an injection needle 18 or other injection or administering device may be connected to the first cartridge 20, as shown in FIG. 8, such as by a threaded connection.

With reference to FIG. 2A, a present embodiment of the pen injection device 10 includes a first cartridge assembly 12, a second cartridge assembly 14, the outer housing 100, and a dual transfer spike assembly 150.

With reference to FIG. 2B, a present embodiment of the first cartridge assembly 12 includes the first cartridge 20, a first cartridge housing 70 configured to receive the first cartridge 20, a first cartridge holder 80, the plunger rod 50, and a plunger 130 (see also FIG. 3B).

Figure 9:
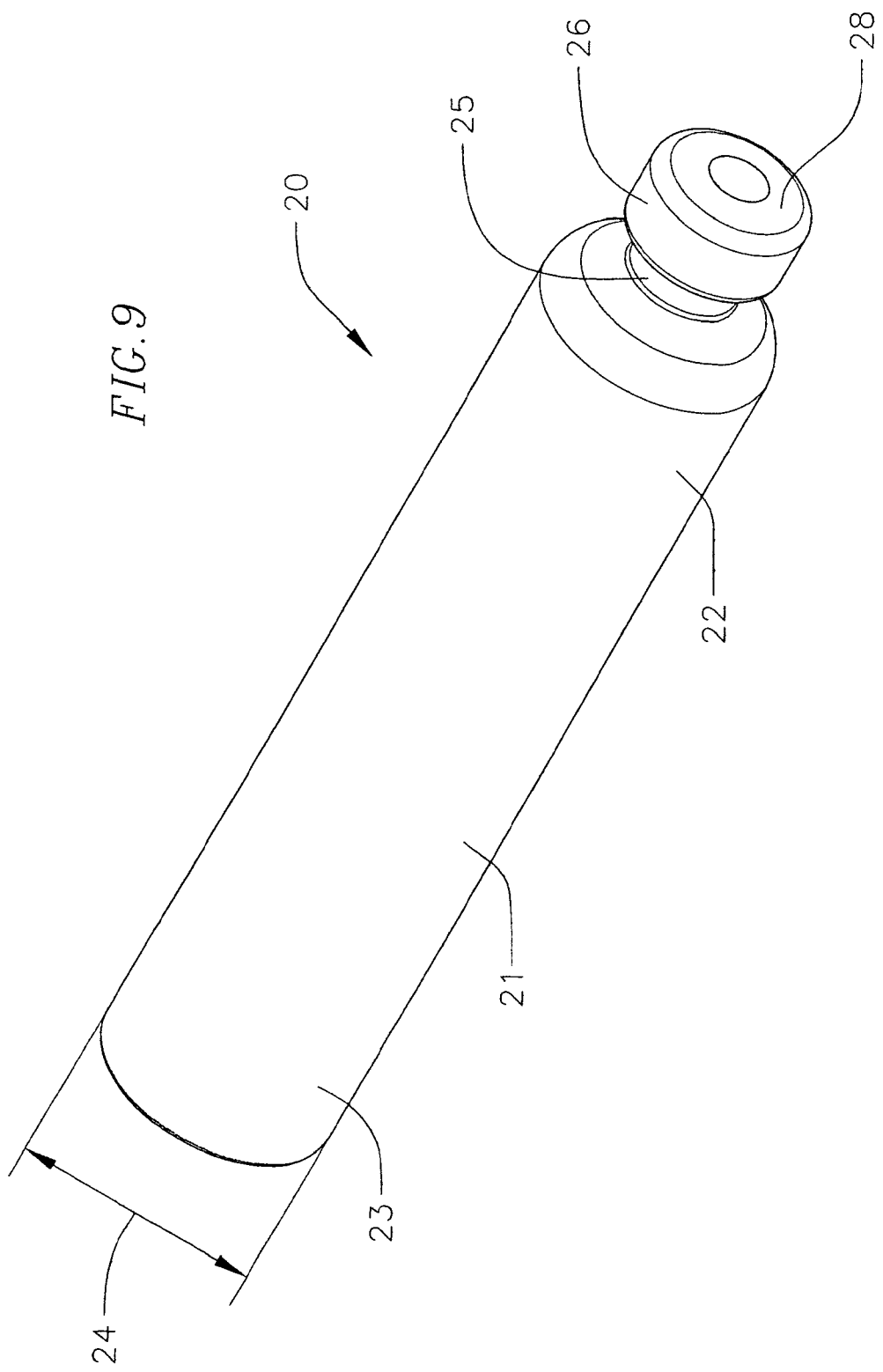
FIG. 9 is a side perspective view of a first cartridge of the pen injection device of FIG. 1.

With reference to FIG. 9, the first cartridge 20 may be any cartridge, vial, or other container containing the first substance. In the present embodiment, the first cartridge 20 is a glass cartridge configured to hold a liquid diluent. Alternatively, the first cartridge 20 may be formed of any other suitable sterilizable material, such as a plastic or stainless steel. In the present embodiment, the first cartridge 20 includes a cylinder 21 having a wall of substantially uniform thickness extending in a cylindrical shape from a first end 22 to a second end 23. The wall of the cylinder 21 forms an internal cavity configured to contain the first substance, the internal cavity having an inner diameter 24. The second end 23 of the first cartridge 20 is open and configured to receive the plunger 130 and the plunger rod 50.

The first cartridge 20 further includes a neck 25 adjacent the first end 22 of the cylinder 21, the neck 25 tapering from and connecting the cylinder 21 and a flange portion 26. The flange portion 26 has an opening configured to release the first substance from the first cartridge 20. In the present embodiment, the flange portion 26 has a diameter greater than a diameter of the neck 25, but less than the inner diameter 24 of the cylinder 21. The first cartridge 20 further includes a seal 28 covering the opening of the flange portion 26. The seal 28 is configured to be pierced by a spike of the dual transfer spike assembly 150 and, as such, is formed of an elastomeric material or, alternatively, from any other suitable material. The seal 28 may be crimped to the flange portion 26 or connected to the flange portion 26 by another suitable device.

Figure 10A:
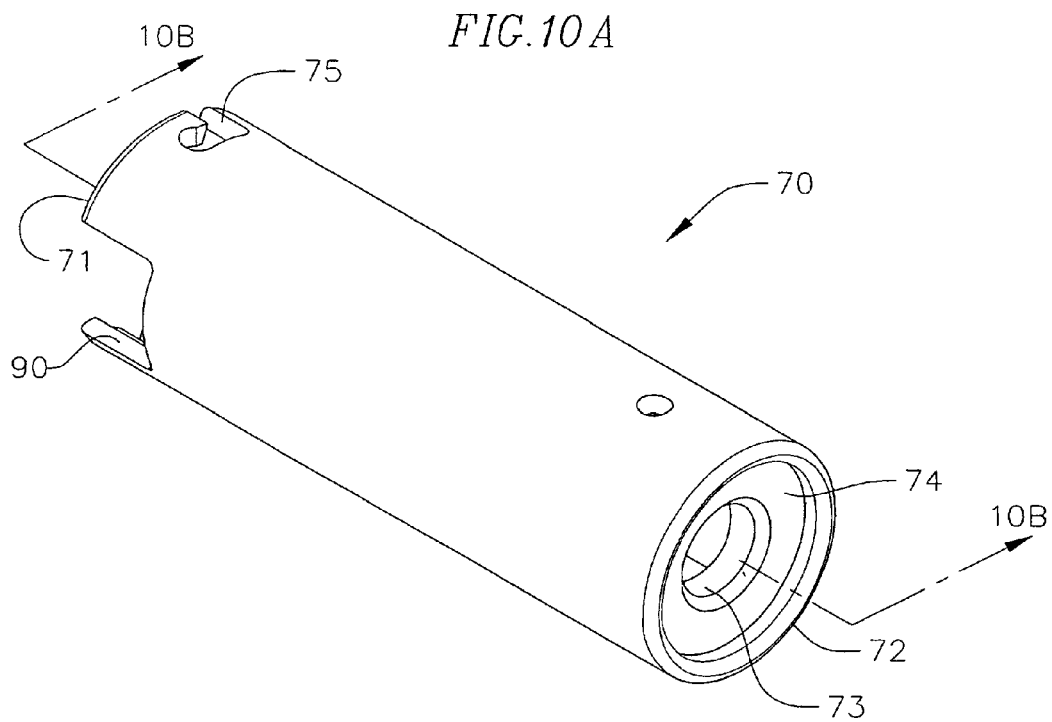
FIG. 10A is a side perspective view of a first cartridge housing of the pen injection device of FIG. 1.
Figure 10B:
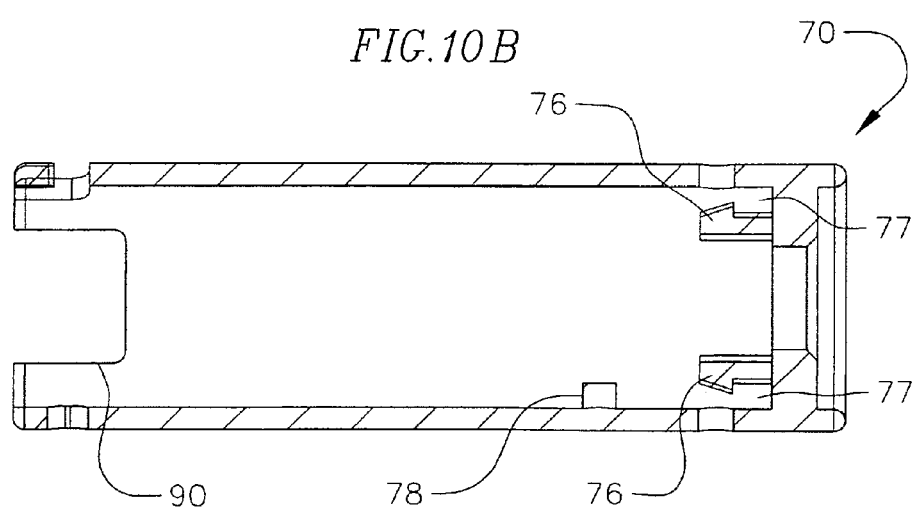
FIG. 10B is a side sectional view through the first cartridge housing of FIG. 10A taken at line 10B-10B.

With reference to FIGS. 10A-B, the first cartridge housing 70 is configured to receive and support the first cartridge 20 and also to receive the plunger rod 50. As such, the first cartridge housing 70 is a tubular structure having a cylindrical shape and a hollow cavity extending from a first end 71 to a second end 72. The first cartridge housing 70 includes an opening 73 at the second end 72 configured to receive a shaft portion of the plunger rod 50. Additionally, in the present embodiment, the first cartridge housing 70 includes a recessed surface 74 at the second end 72 and surrounding the opening 73. The recessed surface 74 is also configured to receive a disc-shaped head 58 of the plunger rod 50 (see also FIG. 12).

The first cartridge housing 70 may be injection molded from medical grade acrylonitrile butadiene styrene (ABS). Alternatively, the first cartridge housing 70 may be formed from any other suitable plastic material or other suitable material, such as a metal, ceramic, glass, or composite material, by any other suitable process.

In the present embodiment, the first cartridge housing 70 includes two or more L-shaped slots 75 located at the first end 71. Each of the L-shaped slots 75 is open at the first end 71, extends a short distance toward the second end 72, forms an angle of approximately ninety degrees, and extends a short distance around the perimeter of the first cartridge housing 70. The first cartridge housing 70, according to the present embodiment, also includes two windows 90 opposite each other and configured to allow a user to view the contents of the first cartridge 20 (i.e., the first substance or the mixture). The windows 90 are formed of a transparent plastic, such as clear medical grade ABS, acrylic, or polycarbonate, or alternatively may be formed of glass or any other suitable transparent material. Alternatively, the windows 90 may be open apertures in the first cartridge housing 70.

With further reference to FIG. 10B, the first cartridge housing 70 includes two protrusions 76 near the second end 72. The protrusions 76 are inside the first cartridge housing 70 and extend away from the second end 72, thereby forming a cavity 77 between each of the protrusions 76 and an inner surface of the tubular wall. The cavities 77 are configured to receive a portion of the first cartridge holder 80, and the protrusions 76 are configured to lock a portion of the first cartridge holder 80, thereby preventing the first cartridge holder 80 from moving axially relative to the first cartridge housing 70, such as during injection of the mixture. The first cartridge housing 70 also includes a protrusion 78 near the second end 72 extending radially inward from an inside surface of the tubular wall. The protrusion 78 is configured to engage a feature of the first cartridge holder 80 and thereby constrain the first cartridge holder 80 from rotating relative to the first cartridge housing 70.

Figure 11A:
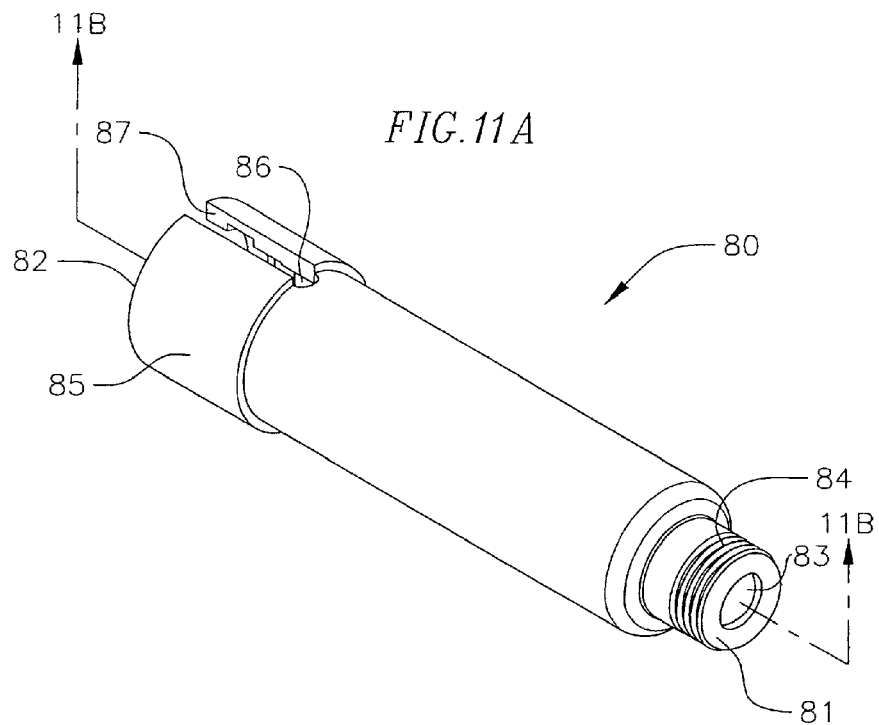
FIG. 11A is a side perspective view of a first cartridge holder of the pen injection device of FIG. 1.
Figure 11B:
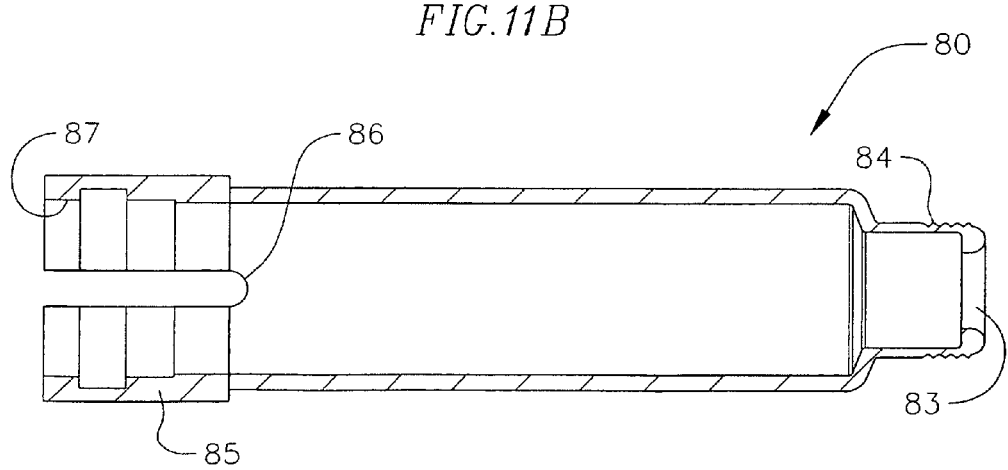
FIG. 11B is a side sectional view through the first cartridge holder of FIG. 11A taken at line 11B-11B.

With reference to FIGS. 11A-B, the first cartridge holder 80 also has a cylindrical shape and an internal cavity extending from a first end 81 to a second end 82. The first cartridge holder 80 is configured to receive the first cartridge 20, which together are received in the first cartridge housing 70. The first cartridge holder 80 is also configured at the first end 81 to connect the injection needle 18 to the first cartridge 20. The first cartridge holder 80 includes an opening 83 at the first end 81 and also, in the present embodiment, a threaded connection 84 configured to connect the injection needle 18 (see FIG. 8). Alternatively, the first end 81 may include any other suitable connection device for connecting the injection needle 18 or another administering device. Also, in the present embodiment, the first cartridge holder 80 has a collar 85 at the second end 82 having an outer diameter that is slightly less than an inner diameter of the first cartridge housing 70, such that when the first cartridge holder 80 is received by the first cartridge housing 70, the first cartridge holder 80 is movable by only a slight amount relative to the first cartridge housing 70 in a radial direction.

The first cartridge holder 80 also has a slot 86 extending from the second end 82 to the end of the collar 85 The slot 86 has a width slightly greater than a width or a diameter of the projection 78 of the first cartridge housing 70. As a result, the projection 78 of the first cartridge housing 70 may extend at least partially through the slot 86 and thereby constrain the first cartridge holder 80 from rotating relative to the first cartridge housing 70, while not constraining the first cartridge holder 80 from moving axially relative to the first cartridge housing 70.

The first cartridge holder 80 is configured to lock into the first cartridge housing 70 when the pen injection device 10 is in an activated position. As such, the first cartridge holder 80 includes a protrusion 87 at the second end 82 extending inwardly from an inner surface of the collar 85 from one edge of the slot 86 and around the inner perimeter of the collar 85 to the opposite edge of the slot 86. The protrusion 87 is configured to slide into the cavities 77 of the first cartridge housing 70 when the activation member 40 is depressed and interlock with the protrusions 76 of the first cartridge housing 70, thereby preventing the first cartridge holder 80 (and the first cartridge 20) from moving axially relative to the first cartridge housing 70 when the plunger rod 50 is depressed.

The first cartridge holder 80 may be injection molded from clear medical grade ABS, acrylic, or polycarbonate. Alternatively, the first cartridge holder 80 may be formed by an alternative process from any other suitable plastic material, or other suitable material, such as a metal, ceramic, glass, or composite material. Further, if the first cartridge holder 80 is formed from a material that is not transparent, then the first cartridge holder 80 may also include one or more windows similar to and positioned to align with the windows 90 of the first cartridge housing 70 when the first cartridge holder 80 is received by the first cartridge housing 70. Such windows may be open apertures in the first cartridge holder 80 or localized portions of a transparent material coupled to the material of the first cartridge holder 80.

Figure 12:
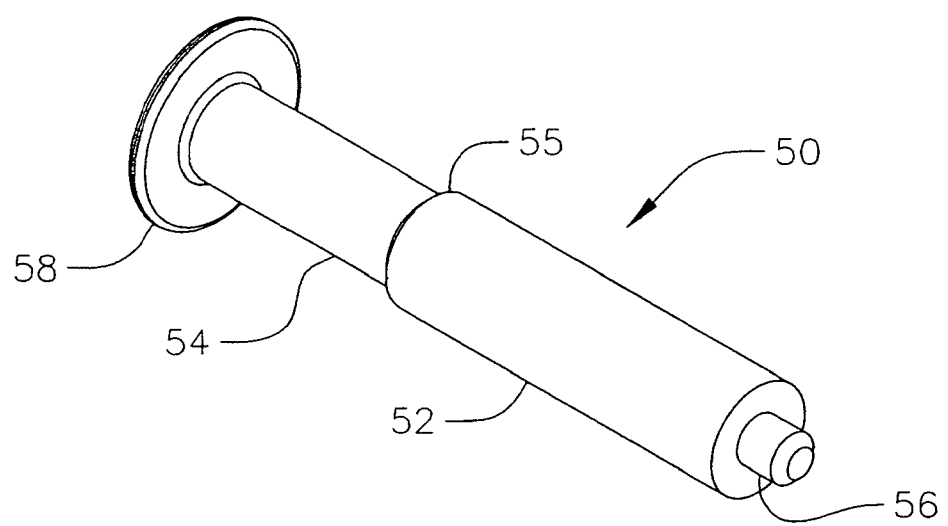
FIG. 12 is a side perspective view of a plunger rod of the pen injection device of FIG. 1.

With reference to FIG. 12, the plunger rod 50 includes a first shaft portion 52 that is substantially cylindrical and has a diameter that is slightly smaller than the inner diameter 24 of the cylinder 21 of the first cartridge 20. The plunger rod 50 further includes a second shaft portion 54 joined to the first shaft portion 52 at a shoulder 55. The second shaft portion 54 has a diameter that is smaller than the diameter of the first shaft portion 52.

The plunger rod 50 includes a protrusion 56 at an end of the first shaft portion 52 opposite the shoulder 55. The protrusion 56 is also cylindrical in shape and has a diameter smaller than the diameter of the first shaft portion 52. Additionally, the protrusion 56 may be externally threaded. The plunger rod 50 further includes the disc-shaped head 58 at an end of the second shaft portion 54 opposite the shoulder 55 and having a diameter greater than the diameter of the second shaft portion 54. The head 58 is configured to withstand a force exerted on the head 58 by a user, such as when the user depresses the plunger rod 50 into the first cartridge housing 70 to mix the first and second substances or inject the mixture.

In the present embodiment, the plunger rod 50 is injection molded as a unitary component from medical grade ABS. Alternatively, the plunger rod 50 may be formed from any other suitable plastic material, or other material, such as a metal, ceramic, glass, or composite material, by any other suitable process. Moreover, some or all of the components described above, such as the first shaft portion 52 and the second shaft portion 54, may be formed separately and connected by a suitable device.

In the present embodiment, the plunger 130, depicted in FIG. 3B, is configured to deter the first substance or the mixture from exiting the first cartridge 20 past the plunger rod 50, including while the first substance is under increased pressure when the plunger rod 50 is depressed. The plunger 130 may be formed of an elastomeric material or an alternative suitable compressible material. The plunger 130 has a cylindrical shape having a diameter substantially equal to the inner diameter 24 of the cylinder 21 of the first cartridge 20. In the present embodiment, the plunger 130 has an opening 131 at one end. The opening 131 is cylindrical in shape and has a diameter substantially equal to the diameter of the protrusion 56 of the plunger rod 50. As such, the opening 131 of the plunger 130 is configured to receive the protrusion 56 of the plunger rod 50 with a snug fit. Alternatively, the opening 131 may have threads for threadedly engaging an embodiment of the protrusion 56 also having threads.

To assemble the first cartridge assembly 12, with reference to FIGS. 2B and 3B, the plunger 130 is inserted into the first cartridge 20 through the open second end 23. The plunger 130 is inserted such that the plunger 130 is near the first end 22 of the first cartridge 20 and adjacent the first substance. Alternatively, the first cartridge 20 may be supplied having the plunger 130 inserted therein. The plunger 130, having a diameter substantially equal to the inner diameter 24 of the cylinder 21 of the first cartridge 20 and being formed of a compressible elastomeric material, forms a tight seal against the internal cavity of the first cartridge 20, thereby deterring the first substance or the mixture from exiting the second end 23 of the first cartridge 20. The first cartridge 20, having the plunger 130 inserted therein, is inserted into the opening at the second end 82 of the first cartridge holder 80. Because the inside diameter of the first cartridge holder 80 is only slightly greater than an outside diameter of the cylinder 21 of the first cartridge 20, the first cartridge 20 is substantially deterred from moving in a radial direction.

Further, to assemble the first cartridge assembly 12, the first cartridge holder 80 is inserted into the first cartridge housing 70 such that the second end 82 of the first cartridge holder 80 is on the same end as the second end 72 of the first cartridge housing 70 and the projection 78 of the first cartridge housing 70 moves through the slot 86 of the first cartridge holder 80 to align the first cartridge holder 80 relative to the first cartridge housing 70. The first cartridge housing 70 and the first cartridge holder 80 may be configured such that the first cartridge holder 80 is held by a friction fit in the first cartridge housing 70. Alternatively, the first cartridge holder 80 may be constrained from sliding in the first cartridge housing 70 by a locking feature, such as a tab. When the pen injection device 10 is in an activated position, the protrusion 87 of the first cartridge holder 80 is received in the cavities 77 at the second end 72 of the first cartridge housing 70 and captured by the protrusions 76 of the first cartridge housing 70.

Finally, the end of the plunger rod 50 having the first shaft portion 52 is inserted through the opening 73 of the first cartridge housing 70 and the open second end 82 of the first cartridge holder 80 and into the first cartridge 20 through the open second end 23 of the first cartridge 20, such that the plunger rod 50 is adjacent the plunger 130. The protrusion 56 of the plunger rod 50 is threadedly engaged into or otherwise received by the opening 131 of the plunger 130.

With reference to FIG. 2C, a present embodiment of the second cartridge assembly 14 includes a second cartridge 30, an activation member 40 (or "second cartridge housing") configured to receive the second cartridge 30, a biasing mechanism 60, a plunger 132 (see also FIG. 3B), and a spacer 134.

With reference to FIG. 13, the second cartridge 30, similar to the first cartridge 20, may be any cartridge, vial, or other container containing the second substance. The second cartridge 30 may have the same or a different configuration than the first cartridge 20. In the present embodiment, as shown in FIG. 13, the second cartridge 30 is configured similarly to the first cartridge 20, as described above, but is configured to contain a solid, such as a powder. As such, the second cartridge 30 has a neck 35 and a flange portion 36 having larger diameters than the respective diameters of the neck 25 and the flange portion 26 of the first cartridge 20, the smaller diameters of the neck 25 and the flange portion 26 of the first cartridge 20 providing more accurate metering of a liquid, such as a diluent. The second cartridge 30 is formed of glass in the present embodiment, but may alternatively be formed of any other suitable sterilizable material, such as a plastic or stainless steel. In the present embodiment, the second cartridge 30 includes a cylinder 31 having a wall of substantially uniform thickness extending in a cylindrical shape from a first end 32 to a second end 33. The wall of the cylinder 31 forms an internal cavity configured to contain the second substance, the internal cavity having an inner diameter 34. The second end 33 of the second cartridge 30 is open and configured to receive the plunger 132, the spacer 134, and the biasing mechanism 60.

The second cartridge 30 further includes the neck 35 adjacent the first end 32, the neck 35 tapering from and connecting the cylinder 31 and the flange portion 36. The flange portion 36 has an opening configured to release the second substance or the mixture of the first and second substances from the second cartridge 30. In the present embodiment, the flange portion 36 has a diameter greater than a diameter of the neck 35, and also greater than the inner diameter 34 of the cylinder 31. The second cartridge 30 further includes a seal 38 covering the opening of the flange portion 36. The seal 38 is configured to be pierced by a spike of the dual transfer spike assembly 150 and, as such, is formed of an elastomeric material or, alternatively, from any other suitable material. The seal 38 may be crimped to the flange portion 36 or connected to the flange portion 36 by another suitable device.

With reference to FIG. 14, the activation member 40 is configured to receive and support the second cartridge 30. As such, the activation member 40 includes a hollow, cylindrical structure having an opening 41 at a first end 42, the opening 41 configured to receive the second cartridge 30. The activation member 40 is also configured to be at least partially received within an end of the outer housing 100. In the present embodiment, the activation member 40 is injection molded from medical grade ABS. Alternatively, the activation member 40 may be formed by an alternative process from any other suitable plastic material, or other suitable material, such as a metal, ceramic, glass, or composite material.

In the present embodiment, the activation member 40 has a closed second end 43 configured to provide a surface abutting the biasing mechanism 60. The activation member 40 also has an inside diameter 44 that is slightly greater than an outside diameter of the cylinder 31 of the second cartridge 30. Further, the activation member 40 includes two slots 45 opposite each other and extending along a portion of the length of the activation member 40 from the first end 42. The slots 45 are configured such that a force exerted on the outside of the activation member 40 adjacent and between the two slots 45 reduces a diameter of the activation member 40 at the first end 42. The present embodiment of the activation member 40 further includes one or more protrusions 46 on the outside of the cylindrical structure. Each of the protrusions 46 includes a chamfered face 47 facing the first end 42 of the activation member 40.

The biasing mechanism 60, according to the present embodiment, is a compression spring. The compression spring, in the present embodiment, is formed of stainless steel, but alternatively, may be formed of any other suitable metal, plastic, or other material. Also, in the present embodiment, the biasing mechanism 60 does not have to be sterilizable. The stiffness of the spring may be chosen according to the amount of force required to cause the mixture to move to the first cartridge 20. In the present embodiment, the biasing mechanism 60 is configured such that the second substance is not biased toward the first cartridge 20 until the activation force is applied to the activation member 40. That is, in the present embodiment, the compression spring is not compressed until the activation member 40 is depressed into the outer housing 100 toward an activated position. Alternatively, the biasing mechanism 60 may be a gas spring, a piston, a pneumatic device, a tension spring utilized in a configuration inverted from that of the compression spring, or any other suitable device or apparatus for biasing the mixture toward the first cartridge 20. Additionally, in some embodiments, the biasing mechanism 60 may include a vibratory or sonic device configured to improve mixing of the first and second substances after the pen injection device 10 has been activated.

The plunger 132, shown in FIG. 3B, is configured to deter the second substance or the mixture from exiting the second cartridge 30 past the biasing mechanism 60, including while under increased pressure when the plunger rod 50 is depressed. As such, the plunger 132 may be formed of an elastomeric material or an alternative suitable compressible material. The plunger 132 has a cylindrical shape having a diameter substantially equal to the inner diameter 34 of the cylinder 31 of the second cartridge 30.

With further reference to FIGS. 2C and 3B, in the present embodiment, the spacer 134 is between the biasing mechanism 60 and the plunger 132. The spacer 134 is cylindrical in shape and has a diameter that is slightly smaller than the inner diameter 34 of the cylinder 31 of the second cartridge 30. The spacer 134 is configured such that the biasing mechanism 60 may include a compression spring of a predetermined or standard size. Additionally, because the plunger 132 is formed of an elastomeric material, the spacer 134 is configured to provide a more durable surface to press against the biasing mechanism 60. As such, the spacer 134 is formed of a hard plastic material, such as ABS, DELRIN (DELRIN is a registered trademark of E. I. Du Pont de Nemours and Company Corporation), or polypropylene. Alternatively, the spacer 134 may be formed of any other suitable plastic material or a suitable metal, such as steel or aluminum.

To assemble the second cartridge assembly 14, with reference to FIGS. 2C and 3B, the plunger 132 is inserted into the second cartridge 30 through the open second end 33 of the second cartridge 30. The plunger 132 is located near the first end 32 of the second cartridge 30 adjacent the second substance. Alternatively, the second cartridge 30 may be supplied having the plunger 132 inserted therein. The plunger 132, having a diameter substantially equal to the inner diameter 34 of the cylinder 31 of the second cartridge 30 and being formed of a compressible elastomeric material, forms a tight seal against the internal cavity of the second cartridge 30, thereby deterring the second substance or the mixture from exiting the second end 33 of the second cartridge 30. The spacer 134 is also inserted inside the second cartridge 30 and is positioned adjacent the plunger 132. Additionally, the biasing mechanism 60 (or compression spring) is at least partially inserted into the second end 33 of the second cartridge 30. The biasing member 60 is positioned adjacent the spacer 134.

The second cartridge 30, as described above having received the plunger 132, the spacer 134, and the biasing mechanism 60, is inserted into the opening 41 of the activation member 40 to assemble the second cartridge assembly 14. As assembled, the biasing mechanism 60 abuts the inside of the closed second end 43 of the activation member 40. However, in the present embodiment, the biasing mechanism 60 is not biasing until an activation force is applied to the activation member 40. That is, the compression spring is not compressed before the pen injection device 10 is activated. Also, because the inside diameter 44 of the activation member 40 is only slightly greater than an outside diameter of the cylinder 31 of the second cartridge 30, the second cartridge 30 is substantially deterred from moving in a radial direction.

Figure 15B:
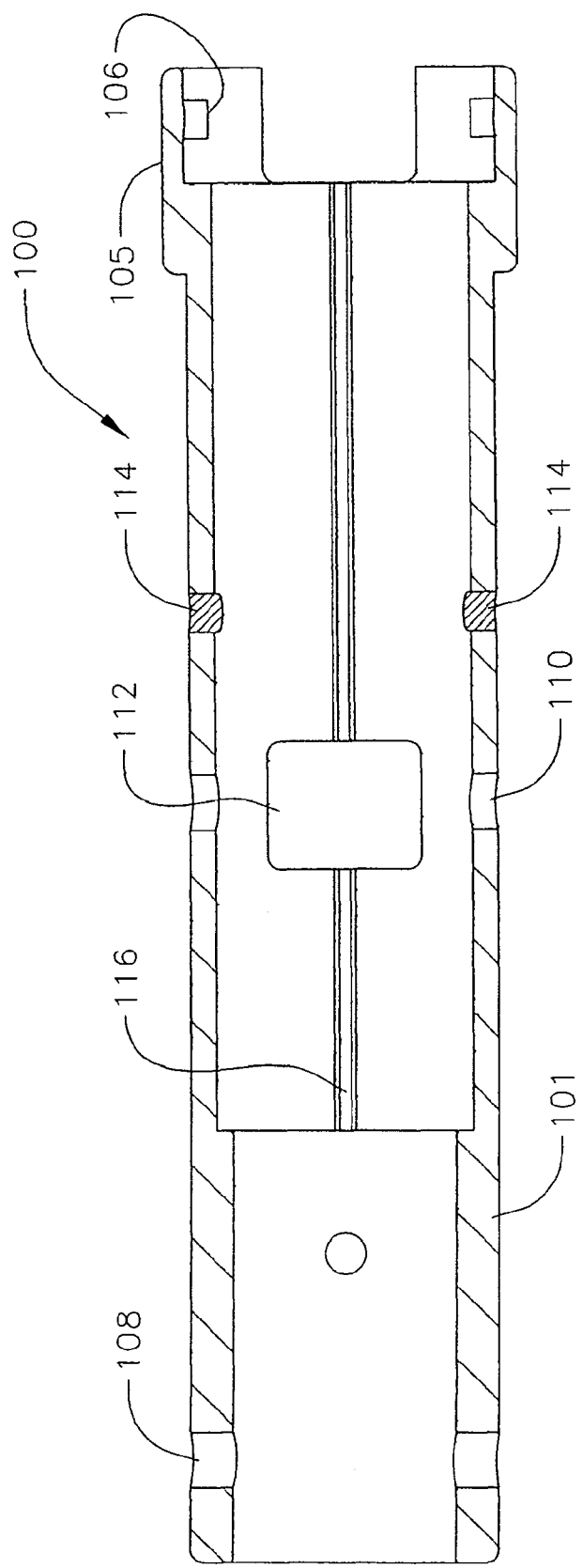
FIG. 15B is a side sectional view through the outer housing of FIG. 15A taken at line 15B-15B.

With reference to FIGS. 15A-B, the outer housing 100 of the pen injection device 10 includes a tubular member having a wall 101 surrounding an internal cavity. In the present embodiment, the wall 101 forms a circular perimeter around the internal cavity. The outer housing 100 also includes a first end 102 having an opening formed therein and a second end 104 having an opening formed therein. The outer housing 100 includes a collar 105 at the first end 102 configured to receive the first end 71 of the first cartridge housing 70. The outer housing 100 may be injection molded from medical grade ABS. Alternatively, the outer housing 100 may be formed from any other suitable plastic material, or other suitable material, such as a metal, ceramic, glass, or composite material, by any suitable process.

In the present embodiment, the outer housing 100 includes two or more pins 106 on the inside of the collar 105 near the first end 102. The pins 106 are configured to be received by the L-shaped slots 75 of the first cartridge housing 70.

The present embodiment of the outer housing 100 also includes at least one opening 108 near the second end 104 and at least one opening 110 located between the at least one opening 108 and the first end 102. The openings 108, 110 are configured to receive the protrusions 46 of the activation member 40, described above.

Additionally, in the present embodiment, the outer housing 100 includes two windows 112 configured and positioned such that the first and second cartridges 20, 30 within the internal cavity of the outer housing 100 are visible through the wall 101 of the outer housing 100. As assembled, in the present embodiment of the pen injection device 10, one of the windows 112 is positioned such that the second cartridge 30 (and the contents therein of an embodiment of the second cartridge 30 that is transparent) is visible after an activation force has been applied to the activation member 40. Another one of the windows 112 may be positioned such that the first cartridge 20 (and the contents therein of an embodiment of the first cartridge 20 that is transparent) is visible after an activation force has been applied to the activation member 40. The one or more windows 112 are formed of a transparent plastic, such as clear medical grade ABS, acrylic, or polycarbonate, or alternatively may be formed of glass or any other suitable transparent material. Alternatively, the one or more windows 112 may be open apertures in the wall 101 of the outer housing 100.

In the present embodiment, the outer housing 100 further includes at least one protrusion 114 configured to control the position of the dual transfer spike assembly 150 by fitting within an opening of the dual transfer spike assembly 150. Further, the one or more protrusions 114 may have beveled edges or be otherwise configured to restrain the dual transfer spike assembly 150 only until a minimum force is applied. Also, in the present embodiment, the outer housing 100 includes two grooves 116 opposite each other on an inner surface of the wall 101 and extending from near the first end 102 to near the second end 104. The grooves 116 are configured to receive a feature, such as a protrusion or a rib, of the activation member 40 and/or the dual transfer spike assembly 150 to constrain the activation member 40 and/or the dual transfer spike assembly 150 from rotating relative to the outer housing 100. The grooves 116 may alternatively have any other suitable configuration and may be present in a quantity other than two.

Figure 16:
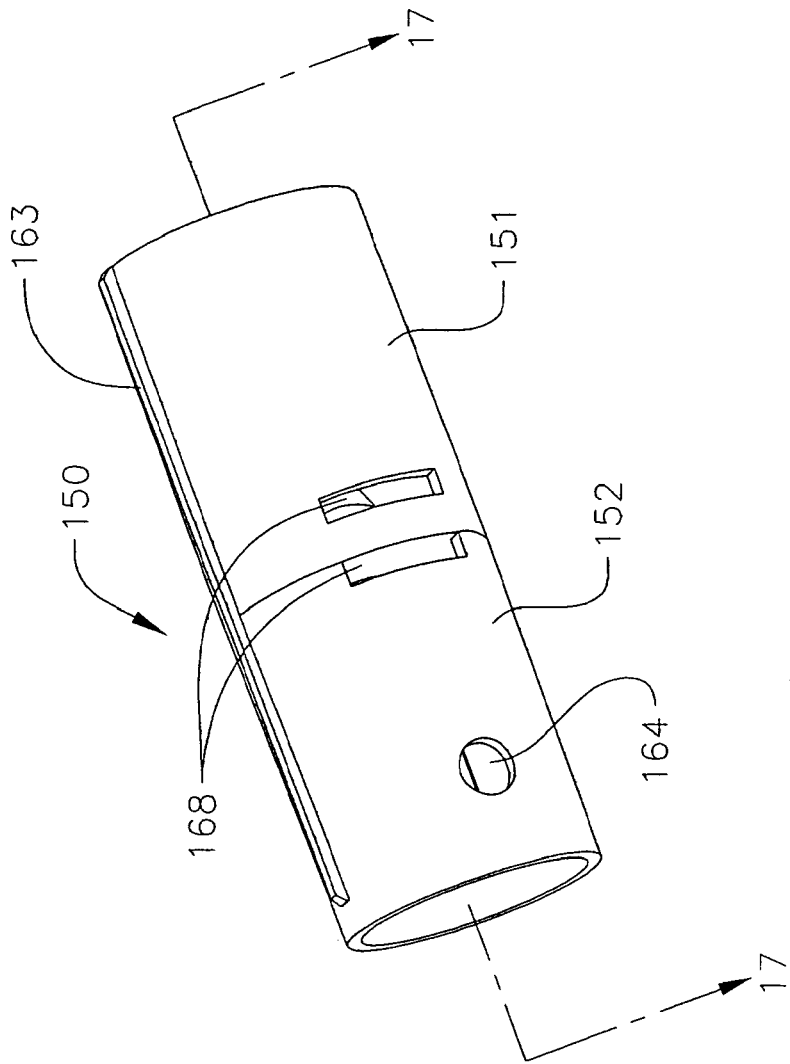
FIG. 16 is a side perspective view of a dual transfer spike assembly of the pen injection device of FIG. 1.
Figure 17:
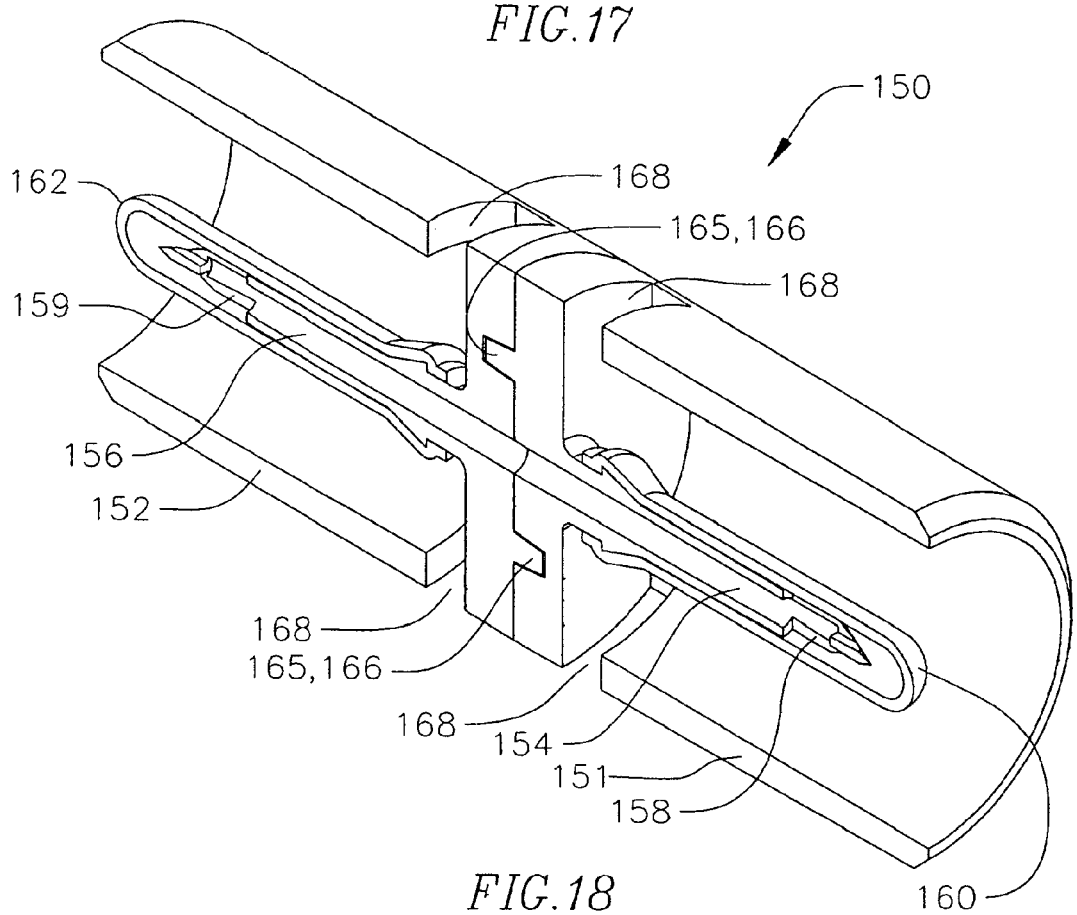
FIG. 17 is a perspective sectional view through the dual transfer spike assembly of FIG. 16 taken at line 17-17.
Figure 18:
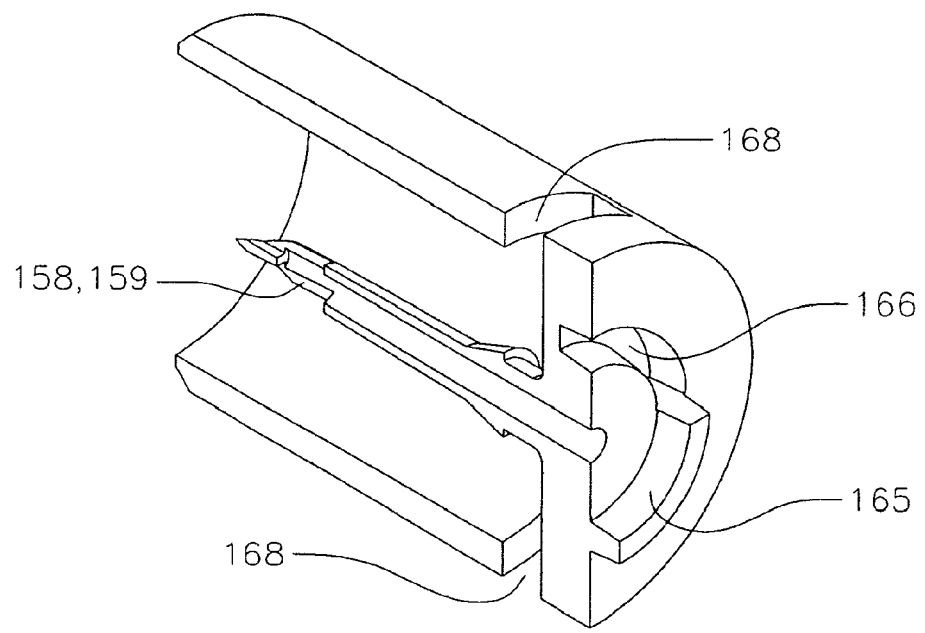
FIG. 18 is a perspective sectional view of a transfer housing portion of the dual transfer spike assembly of FIG. 16.

With reference to FIGS. 16-18, the dual transfer spike assembly 150 includes: a first transfer housing portion 151; a second transfer housing portion 152; a first spike 154 (first end of a dual transfer spike) supported by the first transfer housing portion 101 and having an opening 158; a second spike 156 (second end of a dual transfer spike) supported by the second transfer housing portion 152 and having an opening 159; a first sheath 160 (first separating member); and a second sheath 162 (second separating member), the first sheath 160 surrounding the first spike 154, and the second sheath 162 surrounding the second spike 156. The first and second sheaths 160, 162 are configured to maintain sterility between the first cartridge 20 and the second cartridge 30, while the first spike 154 and the second spike 156 each have an internal cavity, the internal cavities together being configured to provide a fluidic pathway between the first cartridge 20 and the second cartridge 30.

With further reference to FIGS. 17 and 18, in the present embodiment of the dual transfer spike assembly 150, the first and second transfer housing portions 151, 152 have substantially the same configuration. Alternatively, the dual transfer spike assembly 150 may include a unitary housing supporting the first and second spikes 154, 156. The first and second transfer housing portions 151, 152 may be injection molded from medical grade ABS. Alternatively, the first and second transfer housing portions 151, 152 may be formed by an alternative process from any other suitable plastic material, or other suitable material, such as a metal, ceramic, glass, or composite material.

With further reference to FIG. 16, the dual transfer spike assembly 150, according to the present embodiment, also includes two alignment ribs 163. The alignment ribs 163 are configured to be received by the grooves 116 of the outer housing 100 such that the dual transfer spike assembly 150 is constrained from rotating relative to the outer housing 100. The alignment ribs 163 may vary in number and shape, and may be on one or both of the first and second transfer housing portions 151, 152. The dual transfer spike assembly 150 may also include one or more openings 164 for locating and/or aligning the dual transfer spike assembly 150 inside the outer housing 100, such as by receiving the one or more protrusions 114 of the outer housing 100 or an alternative similar feature. Additionally, the openings 164 or other similar features of the dual transfer spike assembly 150, along with features of the outer housing 100, the activation member 40, the first cartridge housing 70, and/or the first cartridge holder 80, may be configured and positioned to control a sequence of activation of the pen injection device 10. For example, the pen injection device 10 may be configured so that when it is activated, one of the first and second sheaths 160, 162 is pierced before the other and a fluidic pathway is created between the dual transfer spike assembly 150 and one of the first and second cartridges 20, 30 before a fluidic pathway is created between the dual transfer spike assembly 150 and the other of the first and second cartridges 20, 30.

As further shown in FIGS. 17 and 18, the first and second transfer housing portions 151, 152 are coupled such that a fluidic pathway is provided between the opening 158 of the first spike 154 and the opening 159 of the second spike 156. Each of the first and second transfer housing portions 151, 152 has a raised portion 165 and a groove 166 configured to receive the raised portion 165, such that the first and second transfer housing portions 151, 152 may be coupled and oriented relative to each other. Alternatively, the first and second transfer housing portions 151, 152 may be coupled and oriented by any other suitable feature or device. The first and second transfer housing portions 151, 152 may also include one or more openings 168 for facilitating manufacturability.

In the present embodiment, each of the first and second spikes 154, 156 has an internal cavity, an outer wall extending along the length of the cavity, and the opening 158, 159 through the outer wall such that a fluidic pathway is provided between the opening 158 of the first spike 154 and the opening 159 of the second spike 156 through the internal cavity of each of the first and second spikes 154, 156. Also, each of the first and second spikes 154, 156 has an end configured to pierce the corresponding surrounding sheath 160, 162. Additionally, the ends of the first and second spikes 154, 156 are configured to pierce the seal 28 of the first cartridge 20 and the seal 38 of the second cartridge 30, respectively. Further, in the present embodiment, each of the first and second spikes 154, 156 is integrally formed or molded to the corresponding first or second transfer housing portion 151, 152. Alternatively, the first and second spikes 154, 156 may be connected to and supported by the first and second transfer housing portions 151, 152 by any other suitable device and may be formed of any suitable material, possibly differing from that of the first and second transfer housing portions 151, 152.

In some embodiments, one or both of the first and second spikes 154, 156 may include structural features for creating turbulence along a provided fluidic pathway. For example, the first and second spikes 154, 156 may include internal protrusions or grooves designed to cause turbulence in a fluid passing through the spikes. One such feature may include a spiral fin, as shown in FIG. 21B with respect to another embodiment of a transfer spike. Alternatively, a mixing feature may include any suitable feature or device for increasing turbulence and mixing of substances. Such a feature could bring about more efficient mixing of the first and second substances through the dual transfer spike assembly 150. Another similar feature which may be included for creating turbulent flow within the first and second spikes 154, 156 is a diameter variance, such as a step or a ridge.

In the present embodiment, the two sheaths 160, 162 surrounding the first and second spikes 154, 156 are configured such that when the pen injection device 10 is activated and the first cartridge 20 and/or the second cartridge 30 is pushed against one or both of the sheaths 160, 162, the first and second spikes 154, 156 pierce the surrounding sheath(s) 160, 162, and the sheath(s) 160, 162 thereafter are compressed along the outside wall of the first and/or second spike(s) 154, 156. A fluidic pathway is thereby created between the first and second cartridges 20, 30. In the present embodiment, the two sheaths 160, 162 are formed of an elastomeric material, such as a medical grade silicone compound. Alternatively, the sheaths 160, 162 may be formed of any other suitable material, or combination of materials, such that the sheaths 160, 162 are pierceable by the first and second spikes 154, 156, are compressible, and are capable of maintaining the sterility of the first and second spikes 154, 156 and the fluidic pathway therethrough.

The components and sub-assemblies of the pen injection device 10, according to the present embodiment, are assembled as depicted in FIGS. 1-3B, and as described above with respect to the first and second cartridge assemblies 12, 14 and the dual transfer spike assembly 150. The first cartridge assembly 12 is connected to the outer housing 100 at the first end 102 of the outer housing 100. In the present embodiment, the first cartridge housing 70 of the first cartridge assembly 12 is detachably connected to the outer housing 100 at the L-shaped slots 75 of the first cartridge housing 70, whereby the pins 106 of the outer housing 100 are received by the L-shaped slots 75 according to a bayonet-style connection. Alternatively, the first cartridge assembly 12 and the outer housing 100 may be detachably connected by any other suitable device, such as a threaded connection.

The second cartridge assembly 14 is connected to the outer housing 100 at the second end 104 of the outer housing 100. In the present embodiment, the activation member 40 of the second cartridge assembly 14 is connected to the outer housing 100 at the protrusions 46 of the activation member 40. When the pen injection device 10 is in an unactivated position, the protrusions 46 of the activation member 40 are received by the openings 108 of the outer housing 100 (see FIGS. 3A and 3B). The activation member 40 is slidable relative to the outer housing 100, and is configured to slide in the outer housing 100 from an unactivated first position to an activated second position when an activation force is applied to the activation member 40. When the pen injection device 10 is in the activated second position, the protrusions 46 of the activation member 40 are received by the openings 110 of the outer housing 100 (see FIGS. 6A and 6B). The protrusions 46 of the activation member 40 and the openings 110 of the outer housing 100 may be located to correspond to a desired activation position of the pen injection device 10. Further, the activation member 40 may include an aligning feature (not shown), such as a protrusion, configured to be received by the grooves 116, or another suitable aligning feature, of the outer housing 100, such that the second cartridge assembly 14 is constrained from rotating relative to the outer housing 100.

Alternatively, the second cartridge assembly 14 and the outer housing 100 may be connected by any other suitable device. For example, in an alternative embodiment, the activation member 40 may rotate relative to the outer housing 100 from an unactivated position or threadedly engage the second end 104 of the outer housing 100 to an activated position. In still another alternative embodiment, the activation member 40 may be held in an unactivated position by a pre-loaded spring or other device and may move relative to the outer housing 100 to an activated position upon release of a latch or other device.

The dual transfer spike assembly 150 is located in the internal cavity of the outer housing 100. In the present embodiment, the pen injection device 10 is configured such that the dual transfer spike assembly 150 is movable along the length of the internal cavity of the outer housing 100. Also, the alignment ribs 163 of the dual transfer spike assembly 150 are received by the grooves 116 of the outer housing 100. Assembled as such, the dual transfer spike assembly 150 is constrained from rotating relative to the outer housing 100 so that vent openings and other features remain aligned.

Figure 19:
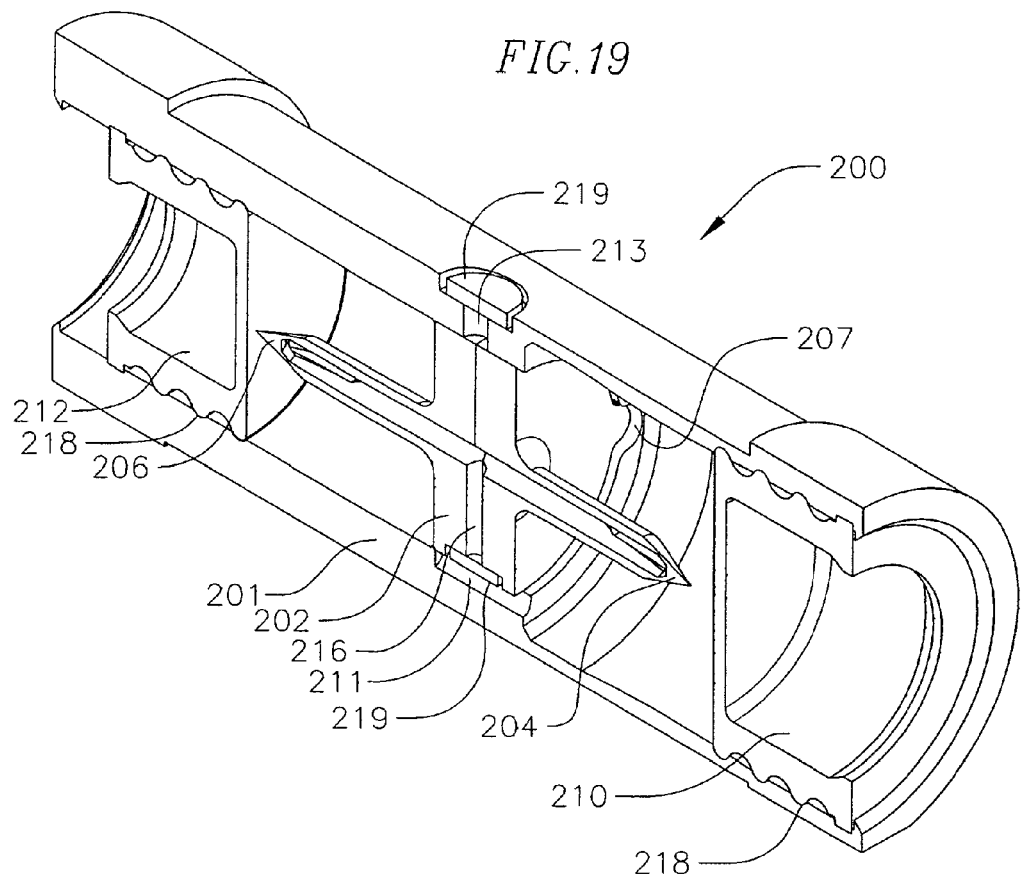
FIG. 19 is a perspective sectional view through a dual transfer spike assembly according to another embodiment of the present invention.

With reference to FIG. 19, a dual transfer spike assembly 200, according to another embodiment, includes: a dual transfer spike housing 201; a dual transfer spike 202 having a first end 204, a second end 206, an opening 208 near the first end 204, and an opening near the second end 206; a first transfer septum 210 (first separating member), and a second transfer septum 212 (second separating member). The dual transfer spike assembly 200 is configured to maintain sterility and provide a fluidic pathway between a first cartridge containing a first substance and a second cartridge containing a second substance.

With further reference to FIG. 19, the dual transfer spike housing 201 houses and supports the dual transfer spike 202. The dual transfer spike housing 201 also at least partially receives at each end one of the first and second transfer septa 210, 212. The dual transfer spike housing 201, according to one embodiment, includes one or more vent openings 213 configured to allow air to exit from the dual transfer spike assembly 200. The dual transfer spike housing 201 may also include a groove 211 for communicating with a venting feature of the dual transfer spike 202. Further, the dual transfer spike housing 201 may include an alignment feature 207, such as a recess, for constraining rotation of the dual transfer spike 202 within the dual transfer spike housing 201. The dual transfer spike housing 201 may be injection molded from medical grade ABS. Alternatively, the dual transfer spike housing 201 may be formed by any other suitable process from any other suitable plastic material, or other suitable material, such as a metal, ceramic, glass, or composite material.

Figure 20:
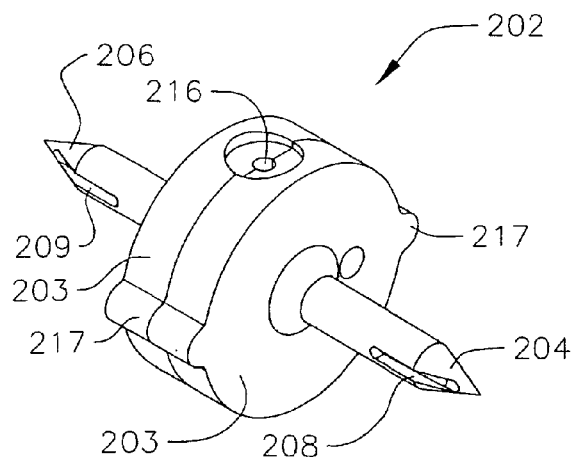
FIG. 20 is a side perspective view of a dual transfer spike of the dual transfer spike assembly of FIG. 19.

As depicted in FIG. 20, the dual transfer spike 202 includes two dual transfer spike portions 203, wherein each of the dual transfer spike portions 203 has the same configuration. One of the two dual transfer spike portions 203 of the dual transfer spike 202 includes the first end 204, and the other dual transfer spike portion 203 includes the second end 206. Alternatively, the dual transfer spike 202 may include a unitary spike including both the first end 204 and the second end 206. The dual transfer spike 202 may be injection molded from medical grade ABS. Alternatively, the dual transfer spike 202 may be formed from any other suitable plastic or other material, such as a metal, ceramic, glass, or composite material, by any suitable process.

Figure 21A:
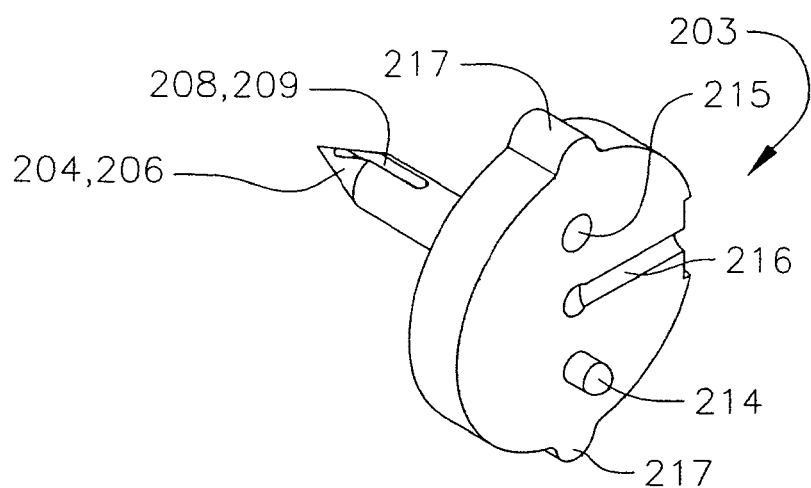
FIG. 21A is a side perspective view of a portion of the dual transfer spike of FIG. 20.
Figure 21B:
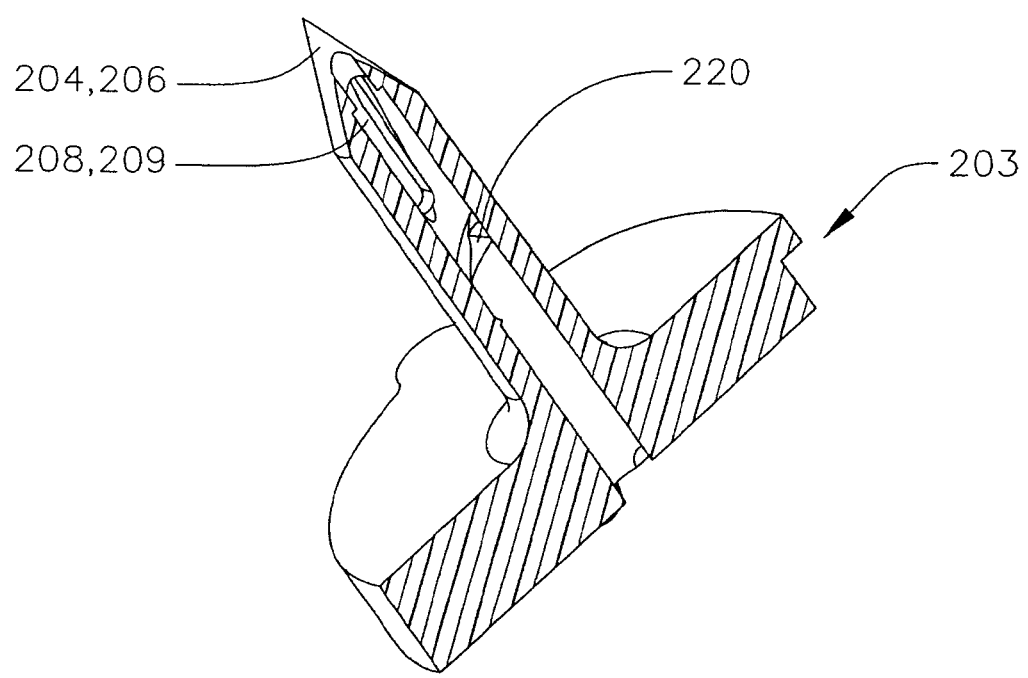
FIG. 21B is a perspective sectional view of a portion of the dual transfer spike of FIG. 20.

With reference to FIG. 21A, the two dual transfer spike portions 203 of the dual transfer spike 202 are coupled such that a fluidic pathway is provided between the opening 208 near the first end 204 and the opening 209 near the second end 206. Each of the two dual transfer spike portions 203 has a protrusion 214 and an opening 215 configured to receive the protrusion 214 such that the two dual transfer spike portions 203 may be coupled and oriented relative to each other. Alternatively, the dual transfer spike portions 203 may be coupled and oriented by any other suitable feature or device. Additionally, in the present embodiment, the dual transfer spike 202 has at least one alignment feature 217 configured to interact with the corresponding alignment feature 207 of the dual transfer spike housing 201 to prevent the dual transfer spike 202 from rotating in the dual transfer spike housing 201.

The dual transfer spike 202 may also include a vent channel 216 configured to allow air to exit from the dual transfer spike assembly 200. Specifically, the vent channel 216 is configured to allow air to be purged from one or both of the first and second cartridges 20, 30. The vent channel 216, for example, is aligned and in communication with the groove 211 of the dual transfer spike housing 201 such that air (e.g., air from one of the first and second cartridges 20, 30) may be vented through the dual transfer spike 202, out of the dual transfer spike 202 through the vent channel 216 and into the interior of the dual transfer spike housing 201 through the groove 211, and finally out of the dual transfer spike housing 201 through the one or more vent openings 213.

Further, as shown in FIG. 19, the dual transfer spike assembly 200 may include at least one filter 219 covering one or both of the vent opening 213 of the dual transfer spike housing 201 and the vent channel 216 of the dual transfer spike 202. The filters 219 are configured to allow air to pass through while deterring a liquid (e.g., a diluent) or a solid (e.g., a powder) from passing through the filters 219. The filters 219 may be membranes covering the vent opening 213 and/or the vent channel 216, or, alternatively, may be plugs at least partially inserted into the vent opening 213 and/or the vent channel 216. Another function of the filters 219 is to maintain the sterility of the dual transfer spike assembly 200.

In the present embodiment, the dual transfer spike 202 has an internal cavity, an outer wall extending along the length of the cavity, and an opening 208 through the outer wall such that a fluidic pathway is provided between the opening 208 near the first end 204 and the opening 209 near the second end 206 through the internal cavity of the dual transfer spike 202. The first and second ends 204, 206 of the dual transfer spike 202 are configured to pierce the first and second transfer septa 210, 212, respectively. Additionally, the first and second ends 204, 206 of the dual transfer spike 202 are configured to pierce the seal 28 of the first cartridge 20 and the seal 38 of the second cartridge 30, respectively.

With reference to FIG. 21B, one or both of the dual transfer spike portions 203 may include a spiral fin 220 in the interior of the dual transfer spike 202 for increasing turbulence and providing more effective mixing of the first and second substances moving through the dual transfer spike 202, as described above with respect to the dual transfer spike assembly 150. Alternatively, either or both of the dual transfer spike portions 203 may include any other suitable mixing feature, structure, or device, or combination thereof, such as internal protrusions, grooves, steps, ridges, or any other features designed to increase turbulence in a fluid passing through the dual transfer spike 202.

In the present embodiment, the first and second transfer septa 210, 212 (first and second separating members) are configured such that when the pen injection device 10 is activated and the first cartridge 20 and/or the second cartridge 30 is pushed against one or both of the first and second transfer septa 210, 212, the first and second ends of the dual transfer spike 202 pierce the first and second transfer septa 210, 212, respectively. A fluidic pathway is thereby created between the first and second cartridges 20, 30. One or both of the first and second transfer septa 210, 212 may have ridges 218 or other various features configured to determine a required amount of activation force or a sequence of activation of the pen injection device 10. In the present embodiment, the first and second transfer septa 210, 212 are formed of an elastomeric material, such as a medical grade chlorobutyl rubber or bromobutyl rubber compound, and may further include a fluoropolymer or fluorocarbon coating. Alternatively, the first and second transfer septa 210, 212 may be formed of any other suitable material, or combination of materials, such that the first and second transfer septa 210, 212 are pierceable by the first and second ends of the dual transfer spike 202. For example, a suitable combination of materials may include a pierceable material around a non-pierceable structure.

Figure 22D:
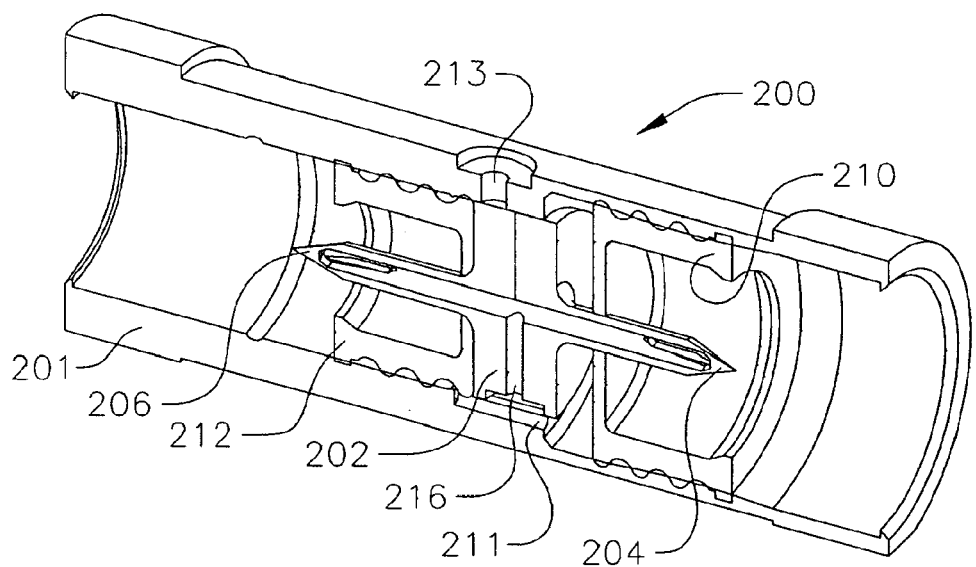

With reference to FIGS. 22A-E, the dual transfer spike 202 and the first and second transfer septa 210, 212 of the dual transfer spike assembly 200 are axially slidable inside the dual transfer spike housing 201 for piercing of the first and second transfer septa 210, 212 to provide a fluidic pathway between a first cartridge and a second cartridge, and also for venting the dual transfer spike housing 201 and the first and second cartridges. For example, the dual transfer spike assembly 200 is shown in FIG. 19 in an unactivated position. As an activation force is initially applied to the first transfer septum 210, there is no path for air venting from the dual transfer spike housing 201 because the vent opening 213 is blocked by the dual transfer spike 202. Therefore, as shown in FIG. 22A, the dual transfer spike 202 and the second transfer septum 212 move a distance substantially equal to the distance that the first transfer septum 210 moves until the dual transfer spike 202 is beyond and no longer blocking the vent opening 213. The filters 219 are not shown in FIGS. 22A-E for clarity.

With reference to FIG. 22B, as an activation force is continued to be applied to the first transfer septum 210, air in the dual transfer spike housing 201 between the dual transfer spike 202 and the first transfer septum 210 is vented through the vent opening 213. As air exits from the dual transfer spike housing 201, there is no pressure causing the dual transfer spike 202 and the second transfer septum 212 to move as the first transfer septum 210 continues to move axially. As a result, the first transfer septum 210 is forced against and is pierced by the first end 204 of the dual transfer spike 202. At this stage, excess air is also vented from the second cartridge through the opening 208 of the first end 204, the internal cavity, and the vent channel 216 of the dual transfer spike 202, and further through the groove 211 and the vent opening 213 of the dual transfer spike housing 201.

With reference to FIG. 22C, once the excess air from the dual transfer spike housing 201 between the dual transfer spike 202 and the first transfer septum 210 and the excess air from the second cartridge has vented through the vent opening 213, the activation force causes the second transfer septum 212 and the dual transfer spike 202 to move toward the first transfer septum 210. The dual transfer spike 202 moves past an edge of the groove 211 of the dual transfer spike housing 201 to define a venting path through the groove 211 through which excess air in the dual transfer spike housing 201 between the dual transfer spike 202 and the second transfer septum 212 can vent.

With reference to FIG. 22D, as the activation force is continued to be applied, the second transfer septum 212 is forced against and pierced by the second end 206 of the dual transfer spike 202. At this stage, excess air is vented from the first cartridge through the opening 209 of the second end 206, the internal cavity, and the vent channel 216 of the dual transfer spike 202, and further through the groove 211 of the dual transfer spike housing 201.

Figure 22E:
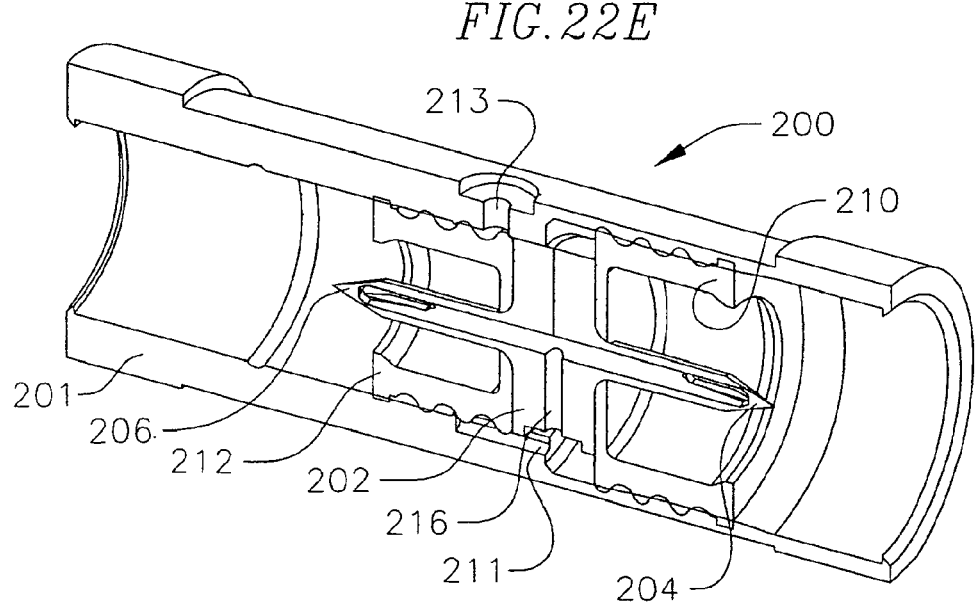

Finally, as shown in FIG. 22E, once the excess air has been vented from the first cartridge, the dual transfer spike 202 and the second transfer septum 212 are forced to a completely activated position against the first transfer septum 210.

In assembly, the dual transfer spike assembly 200 is located within and axially moveable within the internal cavity of the outer housing 100 of the pen injection device 10, similarly to the dual transfer spike assembly 150, as described above.

Still further embodiments of a pen injection device may include various alternative devices for combining a first substance and a second substance. One alternative embodiment of a pen injection device includes a transfer assembly 230, as depicted in FIGS. 23A-C. The transfer assembly 230 includes a first collapsible transfer housing portion 231 and a second collapsible transfer housing portion 232. Each of the first and second transfer housing portions 231, 232 are connected to and surround a transfer spike 234. Each of the two transfer spikes 234 has an internal channel 236 having an opening 238 at the end of the transfer spike 234. The first and second transfer housing portions 231, 232 and the transfer spikes 234 are formed, in one embodiment, of medical grade ABS, but may alternatively be formed of any other suitable plastic material or other suitable material.

Each of the first and second transfer housing portions 231, 232 of the transfer assembly 230 includes, and is collapsible and telescoping as a result of, a series of annular housing segments 240. Each of the housing segments 240 includes a thin wall connected to another one of the housing segments 240 by a very thin intersecting portion (shown in FIG. 23B) configured to break under an applied pressure during activation of the pen injection device. During such activation, each of the housing segments 240, which have sequentially decreasing diameters, collapse around each other such that in the collapsed, activated state, the transfer spike 234 protrudes from a series of radially layered housing segments 240, as shown in FIG. 23C (with a seal described below not shown for clarity).

The transfer assembly 230 further includes two sterile barrier seals 242, or separating members, one attached to each of the first and second transfer housing portions 231, 232. The seals 242 are pierceable by the transfer spikes 234 during activation to provide a fluidic pathway through the transfer assembly 230. The seals 242 are formed of TYVEK (TYVEK is a registered trademark of E. I. Du Pont de Nemours and Company Corporation) or any other suitable sterile sealing material and may be thermally or otherwise attached to the first and second transfer housing portions 231, 232. As an alternative to, or in combination with, the barrier seals 242, the transfer assembly 230 may include pierceable sheaths surrounding the transfer spikes 234. For example, the sheaths may be similar to the sheaths 160, 162 of the dual transfer spike assembly 150 described above and may be formed of an elastomeric or other suitable material.

Figure 24:
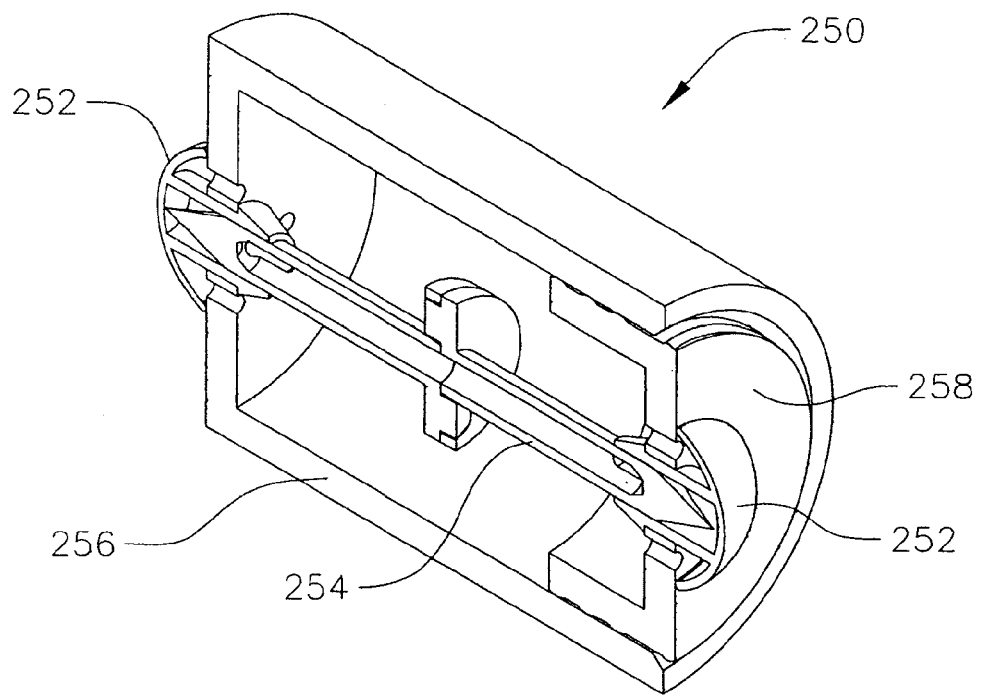
FIG. 24 is a sectional view through a transfer assembly of a pen injection device according to another embodiment of the present invention.

With reference to FIG. 24, another alternative embodiment of a pen injection device includes a transfer assembly 250. The transfer assembly 250 includes an umbrella valve 252 at each of the ends of a dual transfer spike 254. The transfer assembly 250 further includes a first housing portion 256 and a second housing portion 258, the dual transfer spike fixedly attached to the second housing portion 258. The second housing portion 258 is movable with respect to the first housing portion 256, such that an activation order may be predetermined. That is, the pen injection device and the transfer assembly 250 may be configured such that a first end of the dual transfer spike 254 pierces a first umbrella valve 252 before a second end of the dual transfer spike 254 pierces a second umbrella valve 252, thereby creating a fluidic pathway.

Figure 25:
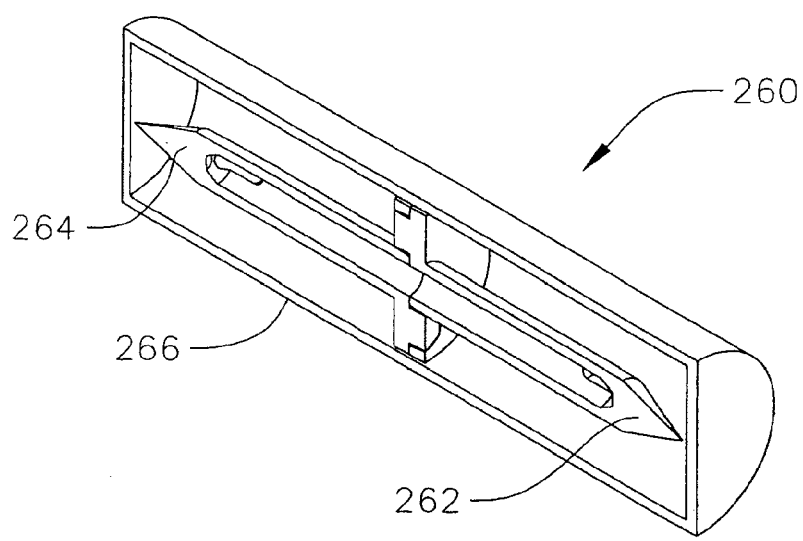
FIG. 25 is a sectional view through a transfer assembly of a pen injection device according to another embodiment of the present invention.

Another alternative embodiment of a pen injection device includes a transfer assembly 260, depicted in FIG. 25. The transfer assembly 260 is a dual transfer spike assembly having a first spike end 262 and a second spike end 264, the dual transfer spike enclosed in a pierceable shell 266. The pierceable shell 266 may be formed of an elastomer, a plastic, or a metal foil, and may be collapsed onto the first and second spike ends 262, 264 during activation to provide a fluidic pathway.

Figure 26:
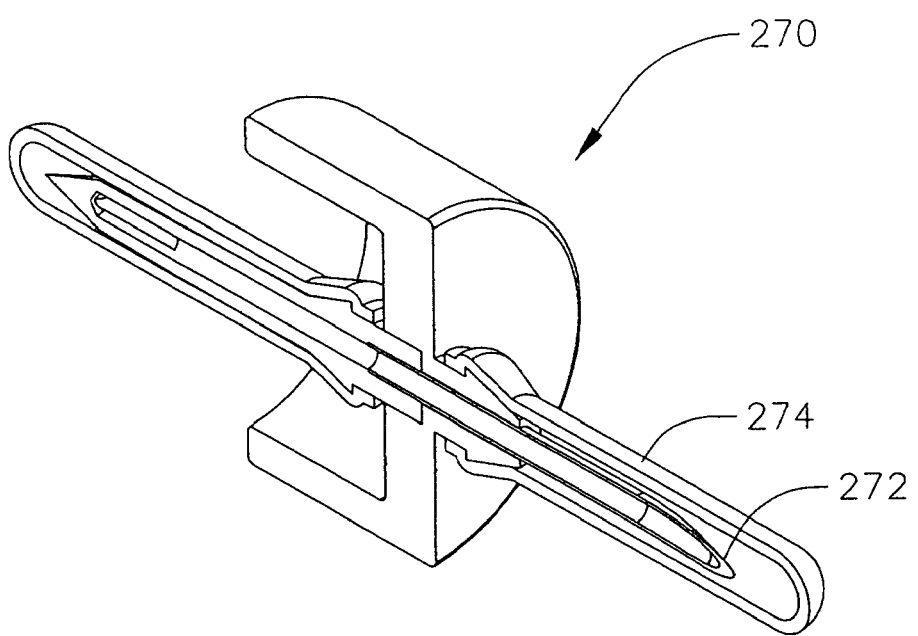
FIG. 26 is a sectional view through a transfer assembly of a pen injection device according to another embodiment of the present invention.

Yet another alternative embodiment of a pen injection device includes a transfer assembly 270, shown in FIG. 26. The transfer assembly 270 includes a needle 272 having a Huber-style point and a pierceable sheath 274 surrounding the needle 272. The transfer assembly 270 is in an outer housing and is configured to provide a fluidic pathway between a first container and a second container. The outer housing may include features configured and located to determine an activation sequence of the transfer assembly 270.

Further, in addition to the various embodiments of transfer assemblies described above for combining a first substance and a second substance, an embodiment of a transfer assembly of a pen injection device may also include various alternative or additional devices or apparatuses for mixing the first and second substances. For example, embodiments of transfer assemblies may include one or more devices, such as a device for increasing turbulence through a transfer assembly (e.g., the spiral fin 220 described above with respect to the dual transfer spike assembly 200, or a similar device), one of the devices described below, or any other suitable device, apparatus, or combination thereof for increasing mixing of the first and second substances.

With reference to FIG. 27, a transfer assembly 280 includes two transfer spike portions 281 having a channel 282 extending therethrough. The transfer assembly 280 further includes a mixing chamber 283 within the channel 282, wherein the mixing chamber 283 has a greater diameter than the channel 282 on either side of the mixing chamber 283. This sudden change of diameter creates turbulence in a fluid moving through the channel 282 and thereby facilitates mixing of the fluid. Further, the transfer assembly 280 includes beads 284, or any other suitable device, in the mixing chamber 283 for obstructing flow of a liquid through the channel 282 and the mixing chamber 283 and thereby facilitating mixing of the fluid. The transfer assembly 280 may also include interlocking devices 285 for capturing the two transfer spike portions 281 from rotating relative to each other.

With reference to FIG. 28, a transfer assembly 290 is similar to the transfer assembly 280 described above. The transfer assembly 290 includes two transfer spike portions 291 having a channel 292 extending therethrough. The transfer assembly 290 further includes a mixing chamber 293 within the channel 292 and having a greater diameter than the channel 292 on either side of the mixing chamber 293, similar to the mixing chamber 283 of the transfer assembly 280 relative to the channel 282. However, rather than having one or more floating obstructions, such as the beads 284 of the transfer assembly 280, the transfer assembly 290 includes at least one stationary protrusion 294 extending from an inside surface of at least one of the spike portions 291 into the mixing chamber 293. The protrusion 294 further creates turbulence to facilitate mixing of first and second substances moving through the channel 292 and the mixing chamber 293. The transfer assembly 290 may also include a venting feature 295 for venting air from the transfer assembly 290, as well as interlocking devices similar to the interlocking devices 285 described above.

Additionally, other embodiments of pen injection devices may include one or more devices or apparatuses for mixing the first and second substances, apart from or in addition to a device of a transfer assembly. Further, the mixing devices or apparatuses described below may be configured for use with the pen injection device 10 described above. As such, these mixing devices and apparatuses may obviate the need for a user to repeatedly depress the plunger rod 50 to mix the first and second substances, or alternatively, may be utilized in conjunction with repeated depression of the plunger rod 50 for increased mixing. Also, the devices or mechanisms may be configured to initiate mixing via a single depression of the plunger rod 50.

Figure 29A:
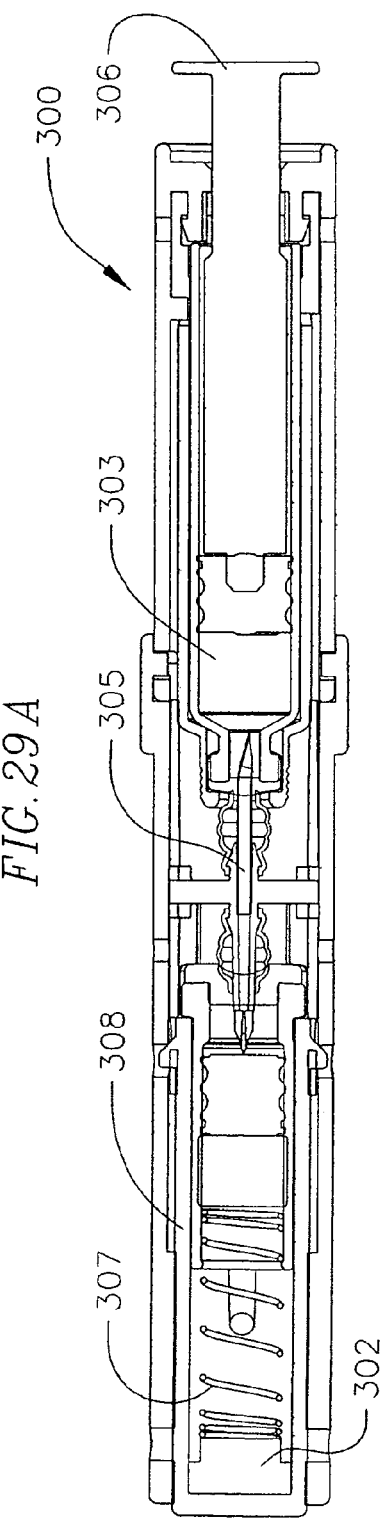
FIGS. 29A-B are sectional views through a pen injection device according to another embodiment of the present invention, the pen injection device at various stages of activation.
Figure 29B:
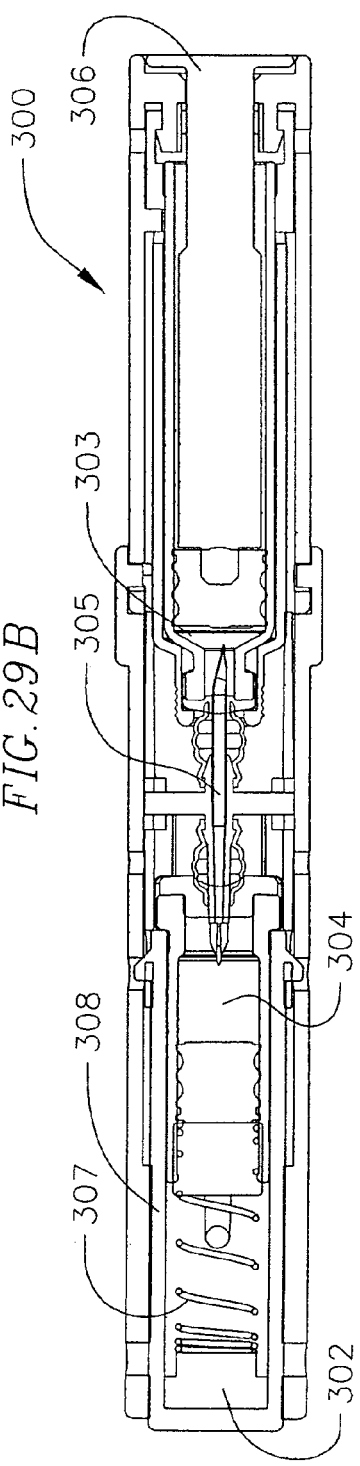

With reference to FIGS. 29A-B, one embodiment of a pen injection device 300 includes a vibrating mechanism 302. The vibrating mechanism 302, according to one embodiment, is configured to shake the first and second substances in a mixing chamber for a predetermined amount of time, thereby mixing the first and second substances. The vibrating mechanism 302 may be any suitable device sized for providing adequate mixing of a first substance from a first container chamber 303 and a second substance in a second container chamber 304. According to the embodiment shown, the mixing occurs in the second container chamber 304, but alternatively, the pen injection device 300 may be configured so that the mixing occurs in the first container chamber 303.

A first substance or mixture is transferred from the first container chamber 303 to the second container chamber 304 through a transfer device 305 (e.g., the dual transfer spike assembly 150 described above with respect to the pen injection device 10) when a plunger rod 306 is depressed from a non-mixing position (see FIG. 29A) to a mixing position (see FIG. 29B). The vibrating mechanism 302 is activated when a biasing mechanism 307 is forced against the vibrating mechanism 302 as a result of the plunger rod 306 being depressed. The mixture in the second container chamber 304 is then shaken by the vibrations of the vibrating mechanism being transmitted through a housing member 308 or the second container. Alternatively, mixing of first and second substances by vibration may be achieved by any other suitable mechanism or process.

With reference to FIGS. 30A-C, a pen injection device 310 is configured to further mix a mixture by rotation. According to one embodiment, the pen injection device 310 includes a torsion spring 312 for rotating a mixing chamber holding the mixture. Alternatively, the rotating motion of the mixing chamber may be driven by a screw, a motor, or any other suitable device or mechanism. The pen injection device 310 is shown in an initial unactivated state in FIG. 30A.

In FIG. 30B, the pen injection device 310 has been activated. That is, a fluidic pathway has been created between a first cartridge chamber 314 and a second cartridge chamber 315 of a second cartridge 316. Further, a plunger rod 313 is in a depressed position, causing a substance or mixture to move from the first cartridge chamber 314 to the second cartridge chamber 315 through a transfer assembly 317 and also compress the torsion spring 312. Once the torsion spring 312 is compressed, a lock is released and torsional motion begins. An interfacing member 318 connecting the torsional spring 312 to a spacer 319 inside the second cartridge 316 is rotated by the torsional motion of the torsion spring 312, causing the second cartridge 316 to spin and thereby mix the substances contained therein.

FIG. 30C shows the pen injection device 310 having the torsion spring 312 unloaded and the plunger rod 313 protruding from the pen injection device 310 rather than depressed. The mixture has been transferred from the second cartridge chamber 315 to the first cartridge chamber 314 through the transfer assembly 317 as a result of the unloading of the torsion spring 312 pressure and release of the plunger rod 313.

Figure 31A:
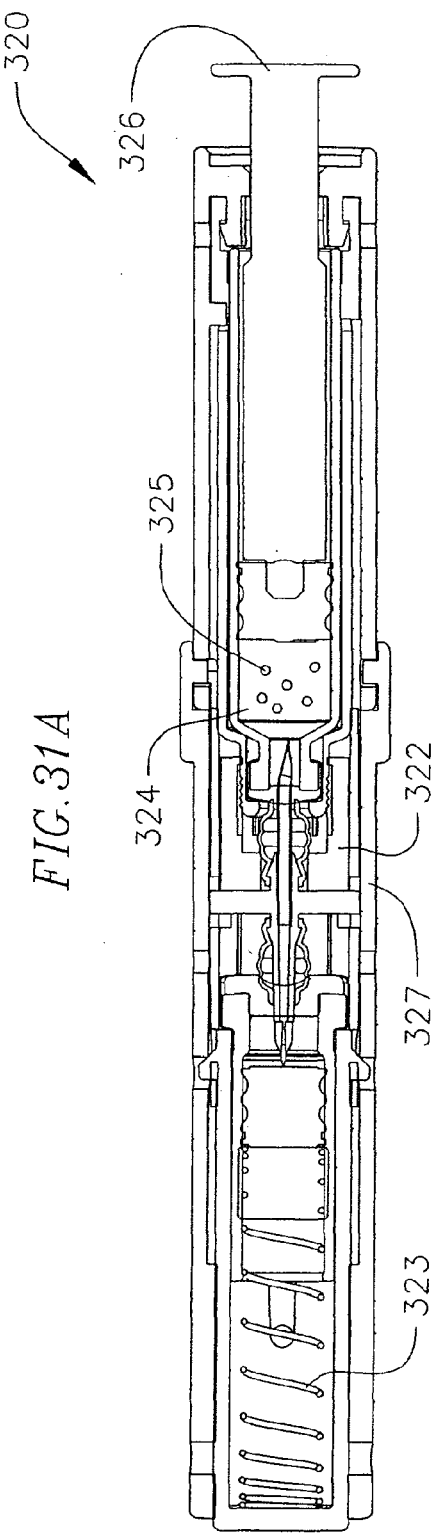
FIG. 31A is a sectional view through a pen injection device according to another embodiment of the present invention.

With reference to FIGS. 31A, a pen injection device 320 includes a magnetic actuator 322 for inducing mixing of first and second substances in a container chamber 324. According to one embodiment, magnetic particles 325 within the container chamber 324 are agitated by the magnetic actuator 322 to actively mix the first and second substances in the container chamber 324 (e.g., one of the first and second cartridges 20, 30 described above with respect to the pen injection device 10). The magnetic actuator 322, according to one embodiment, is activated for agitation of the magnetic particles 325 when a tab of the magnetic actuator 322 is pulled from an initial position wherein a magnetic connection is obstructed to an activated position wherein the tab is not obstructing the magnetic connection. Such motion of the tab may occur when a plunger rod 326 is depressed and compresses a biasing spring 323, or alternatively, when the magnetic actuator 322 is translated relative to an outer housing 327 during activation of the pen injection device 320. Further, the magnetic actuator 322 may remain activated for a predetermined amount of time, after which the pen injection device 320 is ready for injected the mixture. The magnetic particles 325 are sized and shaped for optimal mixing of the first and second substances, and may be formed of an inert, magnetic material. Further, the quantity of the magnetic particles 325 may also be varied depending on the volume of the container chamber 324 or other considerations.

Figure 31B:
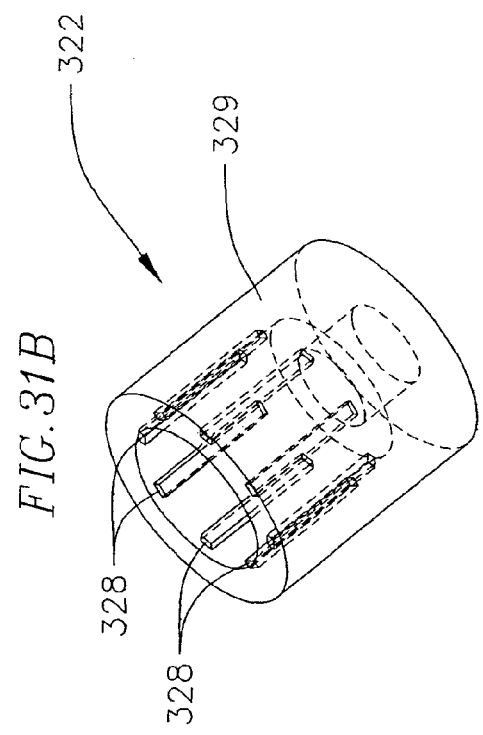
FIG. 31B is a perspective view of a magnet of the pen injection device of FIG. 29A.
Figure 37B:
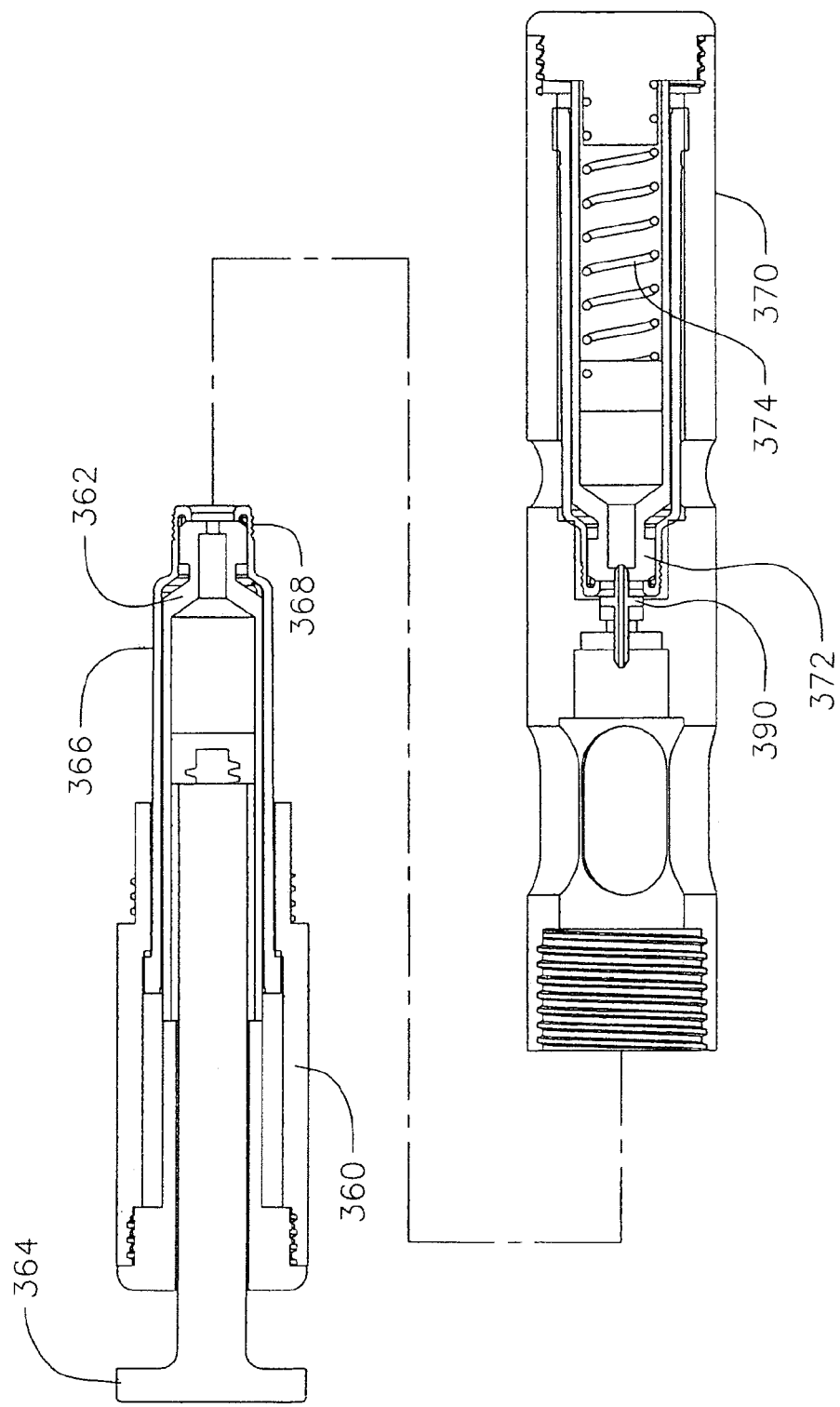
FIG. 37B is a side sectional view through the pen injection device of FIG. 33A taken at line 37B-37B, the pen injection device in an activated state and having a first housing portion disconnected from a second housing portion.

With reference to FIG. 31B, in one embodiment, the magnetic actuator 322 includes alternating polarized magnets 328 within an actuator shell 329. Alternatively, the magnetic actuator 322 may include any other suitable device or mechanism for agitating the magnetic particles 325.

Additionally, another device for mixing a first and second substance may be included in an injection needle, apart from or in combination with a mixing feature of a transfer assembly. With reference to FIGS. 32A-B, according to one embodiment, an injection needle 330 includes an internal feature for increasing turbulence and improving mixing. The injection needle 330 has a first end 332 connectable to a pen injection device, a second end 334 having an opening defining an outlet of an internal channel, and a mixing feature 336 within the channel. In one embodiment, the mixing feature 336 is a spiral fin on an internal surface of the channel of the injection needle 330, similar to the spiral fin 220 of the dual transfer spike assembly 200 described above. Alternatively, the mixing feature 336 may be any other suitable feature or device of the injection needle 330 for creating turbulence and improving mixing of a substance during injection of the substance.

With reference to FIGS. 33A-38B, a pen injection device 350 according to another embodiment is shown. The pen injection device 350 is shown in FIGS. 33A-34B in an unactivated state, that is, not having a fluidic pathway between a first cartridge 362 and a second cartridge 372. In FIGS. 35A-36B, the pen injection device 350 is shown in an activated state wherein a fluidic pathway exists between the first cartridge 362 and the second cartridge 372. Finally, in FIGS. 37A-38B, the pen injection device 350 is shown having a first housing portion 360 disconnected from a second housing portion 370 such that an injection needle or other injection device may be connected to the first housing portion 360 for injecting a mixture into a subject.

The pen injection device 350 includes many components similar to those of the pen injection device 10 and, in many aspects, functions similarly to the pen injection device 10. The pen injection device 350 includes a first housing portion 360, similar to the first cartridge housing 70 of the pen injection device 10, for receiving a first cartridge 362 containing a first substance. The pen injection device 350 also includes a plunger rod 364 similar to the plunger rod 50 of the pen injection device 10. Further, like the first cartridge holder 80 of the pen injection device 10, the pen injection device 350 includes a first cartridge holder 366 configured to hold the first cartridge 362 inside the first housing portion 360. The first cartridge holder 366 has a first end 368, shown in FIGS. 37A-B, configured to couple an injection needle or similar injection device after the pen injection device 350 has been activated.

Further, the pen injection device 350 includes a second housing portion 370 for receiving a second cartridge 372 containing a second substance. The pen injection device 350 also includes a biasing mechanism 374 adapted to bias a mixture toward the first cartridge 362 and the plunger rod 364 toward a first position. In one embodiment, as shown in FIG. 33B, the biasing mechanism 374 is a compression spring. However, as described above with respect to the biasing mechanism 60 of the pen injection device 10, the biasing mechanism 374 may alternatively be a gas spring, a piston, a pneumatic device, a tension spring utilized in a configuration inverted from that of the compression spring, or any other suitable device or apparatus. Also, like the windows 112 of the outer housing 100 of the pen injection device 10, the second housing portion 370 may include one or more windows 380 for viewing the first substance, the second substance, or a mixture thereof, in either or both of the first and second cartridges 362, 372.

Additionally, the pen injection device 350 includes a transfer assembly 390 configured to provide a fluidic pathway between the first cartridge 362 and the second cartridge 372. The transfer assembly 390 may be a double-ended spike having a channel extending between the two ends. Further, each of the two ends of the spike are configured to pierce a seal or similar device of each of the first and second cartridges 362, 372 for containing the first or second substance therein.

The pen injection device 350 houses the first and second cartridges 362, 372 (containing a solid and liquid or liquid and liquid, respectively) and a double-ended spike (rigid tube with sharpened ends) within two pen parts (the first and second housing portions 360, 370). In the unactivated state, the three components are isolated from each other, but are aligned axially.

In one embodiment, the components of the device (the first and second housing portions 360, 370) are plastic, and can be made by injection molding, but in other embodiments can be made of glass, metal, or other materials. The doubled-ended spike of the transfer assembly 390 may also be made of plastic or metal. The first and second cartridges 362, 372 can be pre-filled and sealed for later use.

Once the pen injection device 350 is activated (either by screwing the first and second housing portions 360, 370 together or by pushing them together), the components come together (i.e. the double-ended spike pierces both of the first and second cartridges 362, 372 and provides for communication between the two (solid and liquid) cartridges.

Mixing of the first and second substances is facilitated by depressing the plunger rod 364, which forces the contents of the first cartridge 362 through the transfer assembly 390 and into the second cartridge 372. Once the plunger rod 364 is released, the biasing mechanism 374 forces the contents of the mixture back through the transfer assembly 390 into the first cartridge 362. This process of depressing and releasing the plunger rod 364 is repeated until the first and second substances are mixed. In some embodiments, the windows 380 are incorporated into either or both of the first and second housing portions 360, 370 to allow visual assessment and confirmation of adequate mixing. At the end of each depression and release of the plunger rod 364, the mixed substances will move to the first cartridge 362 (i.e. the cartridge that originally contained the liquid component).

Once the contents (i.e. the first and second substances) are mixed, the first and second housing portions 360, 370 are separated (in different embodiments by unscrewing or pulling apart), and a needle is attached to the exposed first end 368 of the first cartridge holder 366, thus preparing the mixture of the contents for injection by depressing the plunger rod 364.

The second housing portion 370 includes features and performs functions similar to some of the features and functions of each of the activation member 40 and the outer housing 100 of the pen injection device 10. For example, like the outer housing 100 of the pen injection device 10, the second housing portion 370 houses the transfer assembly 390 and is removably coupled to the first housing portion 360. But, like the activation member 40 of the pen injection device 10, the second housing portion 370 houses the second cartridge 372 and the biasing mechanism 374 and is also movable relative to the first housing portion 360 to activate the pen injection device 350.

A feature of the pen injection device 350 that differs from the pen injection device 10 described above is the manner in which the pen injection device 350 is activated to create a fluidic pathway between the first and second cartridges 362, 372. That is, the second housing portion 370 is movable relative to the first housing portion 360 by rotation or threaded engagement. This rotating movement, however, causes an axial movement of the second housing portion 370 toward the first housing portion 360 to pierce a seal of each of the first and second cartridges 362, 372 on either end of the double-ended spike of the transfer assembly 390. In contrast, the pen injection device 10 is configured such that the activation member 40 is translatable relative to the first cartridge housing 70 by a direct axial activation force to create a fluidic pathway between the first and second cartridges 20, 30. However, alternative embodiments of the pen injection device 10 may be activated by a rotating or threading motion of components relative to each other. Similarly, the pen injection device 350 may alternatively be activated by providing an activation force to one end of one of the first and second housing portions 360, 370, as described above with respect to the present embodiment of the pen injection device 10. That is, many of the components, as well as methods of assembly and use, of embodiments of the pen injection device 10 and embodiments of the pen injection device 350 described herein are interchangeable.

In another embodiment, a pen injection device facilitates the connection of two separate vessels (one pre-filled with diluent and one pre-filled with powder) in a "pen-type" device via a two-piece adapter. The vessels may be any combination of vial or cartridge. Mixing of the powder and diluent can occur by transferring the contents from chamber to chamber through a spike channel or other adapter via motion of plungers. At the completion of mixing, the suspension is contained entirely within the chamber that originally contained the diluent. The two chambers are then separated. During this separation, the two-piece transfer device separates with one part remaining attached to the suspended drug. A needle is attached to the exposed end of the chamber containing the suspension in preparation for injection of the drug.

Figure 39:
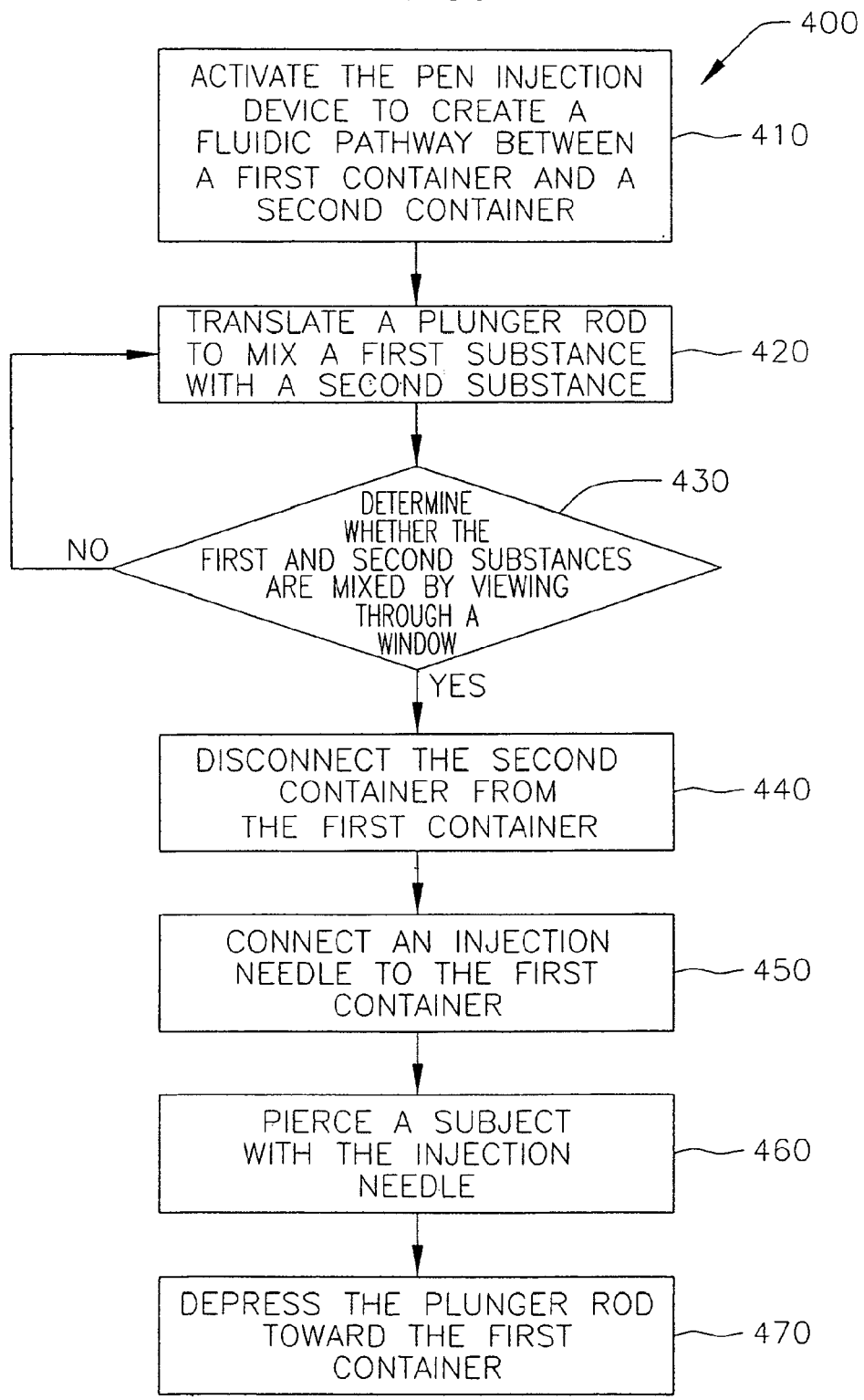
FIG. 39 is a flow diagram of a method of using a pen injection device according to aspects of the present invention.

With reference to FIG. 39, a flow diagram is shown illustrating a method 400 of using a pen injection device having a first container, a second container, a plunger rod, and a biasing mechanism. For the sake of clarity and consistency in description, the method 400 is described below in connection with the pen injection device 10 described above. However, the method 400 of using a pen injection device may also be performed using the pen injection device 300 or alternative embodiments of a pen injection device. As described below, the first container and the first cartridge 20 described above are interchangeable, and similarly, the second container and the second cartridge 30 are interchangeable.

The method 400 of using a pen injection device, according to the present embodiment, commences with task 410. In task 410, a pen injection device is activated, thereby creating a fluidic pathway between the first container and the second container. With respect to the embodiment of the pen injection device 10, as described above, the pen injection device 10 is activated by applying an activation force to the activation member 40, the pen injection device 10 initially in an unactivated position, as shown in FIGS. 1 and 3A-B.

The activation force required may vary depending on the geometry and/or components and features of the pen injection device 10. For example, the size and location of the protrusions 46 of the activation member 40 relative to the openings 108 of the outer housing 100 may be determinative of the amount of force that is required to activate the pen injection device 10. In the present embodiment, as a user applies an activation force to the activation member 40, the chamfered faces 47 of the protrusions 46 (see FIG. 14) are forced against opposite edges of the openings 108 of the outer housing 100 (see FIG. 15A) and thereby create an inward force on the activation member 40. This inward force and the geometry of the slots 45 of the activation member 40 allow the diameter of the first end 42 of the activation member 40 to be reduced, thereby allowing the protrusions 46 to be released from the openings 108 of the outer housing 100 and allowing the activation member 40 to be translated toward an activated position. As the activation force is applied to the activation member 40, a fluidic pathway is created between the first cartridge 20 and the second cartridge 30.

FIGS. 4A and 4B show the pen injection device 10 in a first partially activated position. That is, activation has been initiated by applying an activation force to the activation member 40, but the activation member 40 has moved only a portion of the distance required for complete activation. As the activation member 40 is moved from the unactivated position (see FIGS. 3A and 3B), wherein the plunger rod 50 is substantially inside the first cartridge housing 70 and cannot be depressed, to the first partially activated position, the plunger rod 50 is translated to an activated position, wherein the plunger rod 50 protrudes from the first cartridge housing 70 such that it can be depressed to transfer the contents of the first cartridge 20. In the present embodiment, the plunger rod 50 is partially ejected from the first cartridge housing 70 to the activated position as a result of the activation member 40 being indirectly forced against the second cartridge 30, the second cartridge 30 thereby being forced against the dual transfer spike assembly 150, which, in turn, is forced against the first cartridge 20, pushing the plunger rod 50 partially from the first cartridge housing 70. At the same time, the first cartridge holder 80 slides axially relative to the first cartridge housing 70, and continues, so long as an activation force is applied to the activation member 40, until the second end 82 of the first cartridge holder 80 abuts the bases of the cavities 77 of the first cartridge housing 70 and the protrusion 87 of the first cartridge holder 80 interlocks with the protrusions 76 of the first cartridge housing 70 to deter further axial movement of the first cartridge holder 80 relative to the first cartridge housing 70.

After the second end 82 of the first cartridge holder 80 abuts the bases of the cavities 77 of the first cartridge housing 70, continued force on the activation member 40 causes each of the seal 38 of the second cartridge 30 and the second separating member 162 to be pierced by the second spike 156 (second end of the dual transfer spike). After the seal 38 and the second separating member 162 have been pierced in the first partially activated position, air may be vented from the second cartridge 30. The pen injection device 10 may be configured through various features, such as the protrusions of the outer housing 100, to control a sequence of activation of the pen injection device 10. For example, as shown in FIGS. 4B and 5B, the seal 38 of the second cartridge 30 and the second separating member 162 may be pierced by the second spike 156 (second end of the dual transfer spike) before each of the seal 28 of the first cartridge 20 and the first separating member 160 are pierced by the first spike 154 (first end of the dual transfer spike). Alternatively, the pen injection device may be configured such that the seal 28 of the first cartridge 20 and the first separating member 160 are pierced first.

Figure 5A:
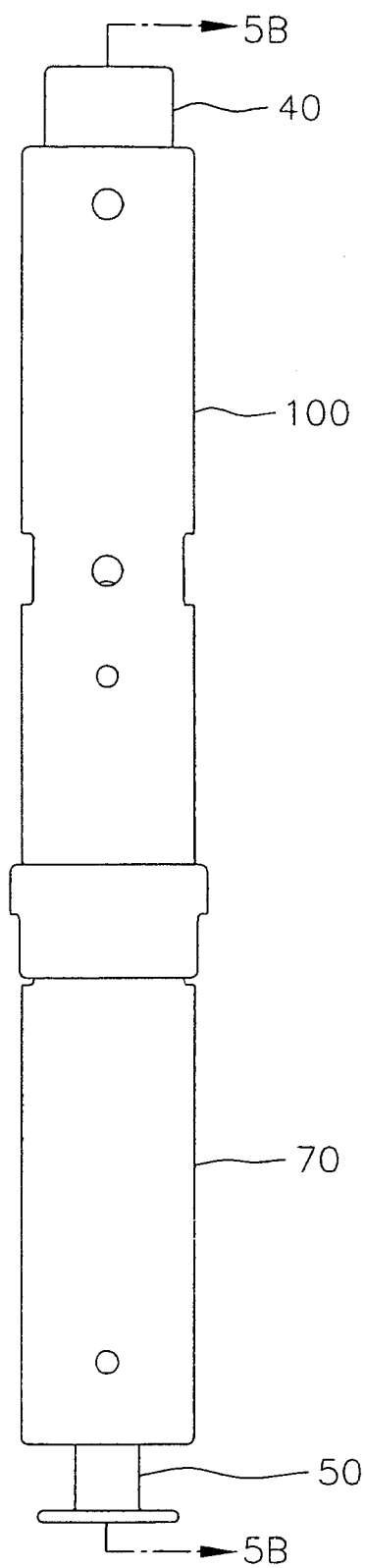
FIG. 5A is a side view of the pen injection device of FIG. 1, the pen injection device in a second partially activated position.
Figure 5B:
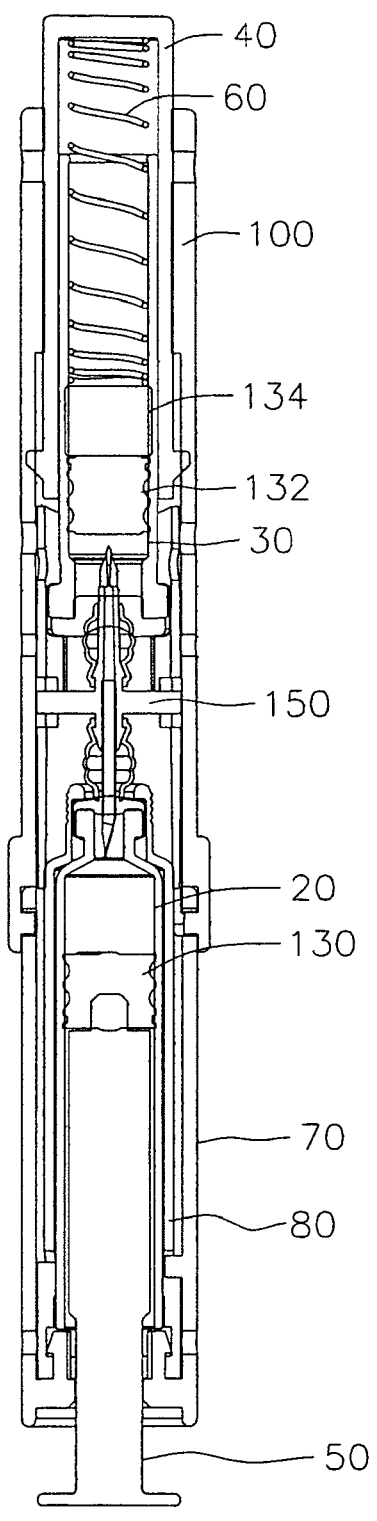
FIG. 5B is a side sectional view through the pen injection device of FIG. 1 taken at line 5B-5B, the pen injection device in a second partially activated position.

FIGS. 5A-B show the pen injection device 10 in a second partially activated position. At this stage of the activation process, the activation member 40 has moved closer to a position wherein the pen injection device 10 is completely activated. At the second partially activated position, each of the seal 28 of the first cartridge 20 and the first separating member 160 are pierced by the first spike 154 (first end of the dual transfer spike). At this stage, air may be vented from the first cartridge 20. The fluidic pathway is provided between the first cartridge 20 and the second cartridge 30 at this stage of the activation process of task 410. Alternatively, each of the seal 28 of the first cartridge 20 and the first separating member 160 may be pierced by the first spike 154 (first end of the dual transfer spike) before each of the seal 38 of the second cartridge 30 and the second separating member 162 are pierced by the second spike 156 (second end of the dual transfer spike). Further, the order in which a fluidic pathway is created to or from the first and second cartridges 20, 30 may be predetermined and may be controlled by features of the pen injection device 10, such as protrusions or other structural features on the outer housing 100 or the dual transfer spike assembly 150.

Figure 6A:
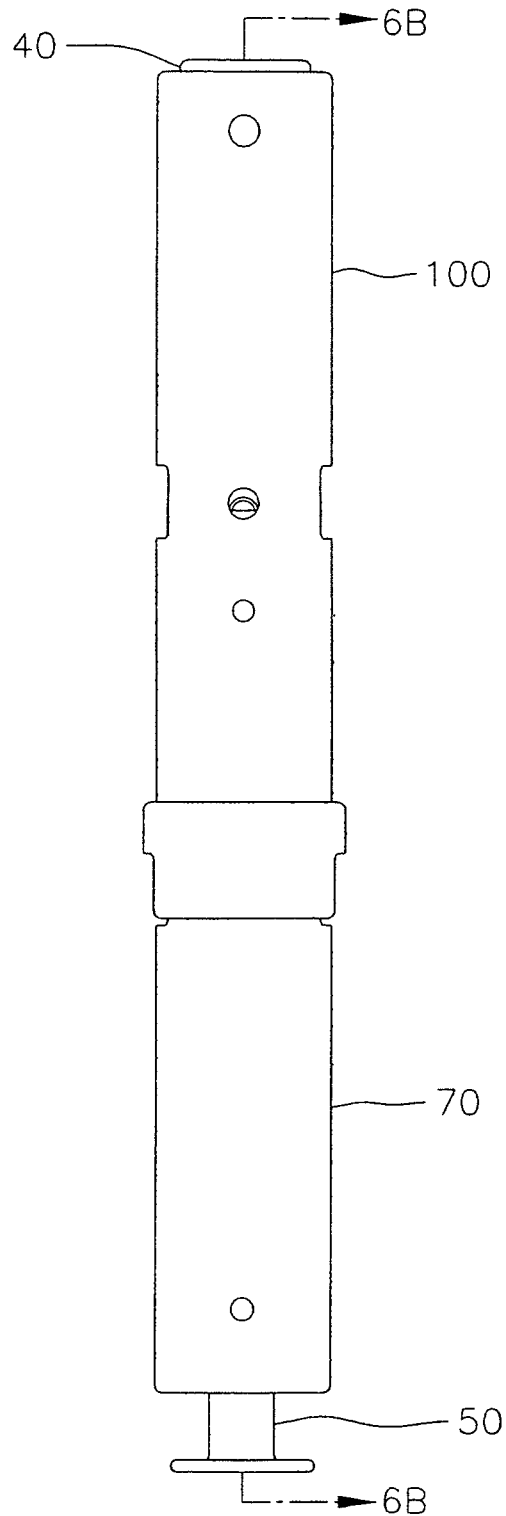
FIG. 6A is a side view of the pen injection device of FIG. 1, the pen injection device in an activated state.
Figure 6B:
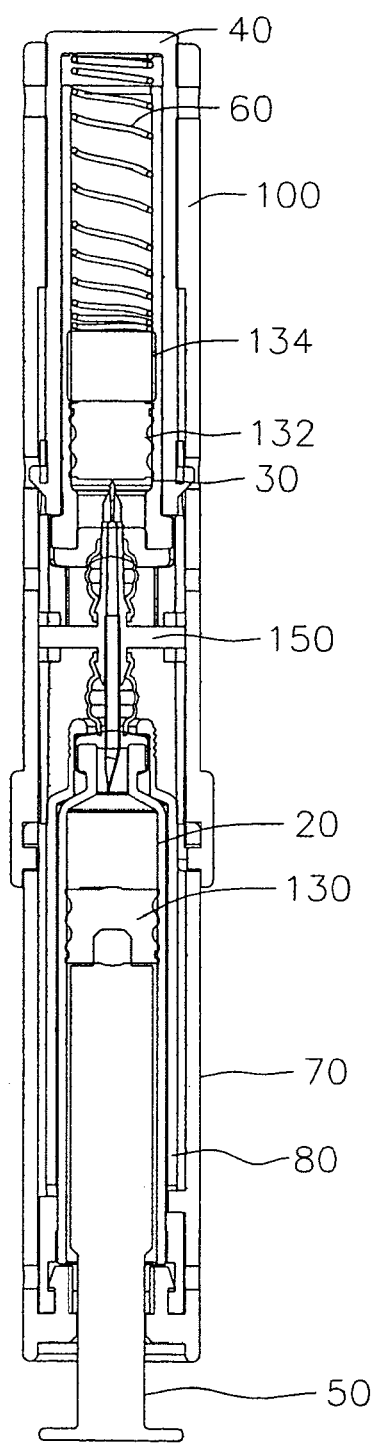
FIG. 6B is a side sectional view through the pen injection device of FIG. 1 taken at line 6B-6B, the pen injection device in an activated state.

The pen injection device 10 is shown in FIGS. 6A-B in a completely activated position, such as after task 410 has been performed. In the activated position, the protrusions 46 of the activation member 40 are received by the openings 110 of the outer housing 100. As the activation force is applied to the activation member 40, at least a portion of a first substance may move from the first cartridge 20 to the second cartridge 30 to combine with a second substance and form a mixture. The biasing mechanism 60 causes the mixture to move to the first cartridge 20.

The fluidic pathway may be created by any of the components or features, or any combination thereof, according to the embodiments of the pen injection device 10 described above, such as the dual transfer spike assembly 150, or by any other suitable device or apparatus. According to another embodiment, a fluidic pathway may be created between the first and second cartridges 20, 30 by threading or rotating the activation member 40 relative to the outer housing 100, rather than by translating the activation member 40 toward the outer housing 100 by applying an activation force, as described above. Such a threading or rotating task for creating a fluidic pathway between a first container and a second container is shown, for example, in FIGS. 34A-35B with respect to the pen injection device 300, wherein the first housing portion 310 is rotated relative to the second housing portion 320 to create a fluidic pathway between the first cartridge 312 and the second cartridge 322. Alternatively, task 410 may include activating a pen injection device by any other suitable device, such as by creating a fluidic pathway by releasing a latch to exert a pre-loaded spring, as opposed to manually depressing the activation member 40 of the pen injection device 10.

Figure 7A:
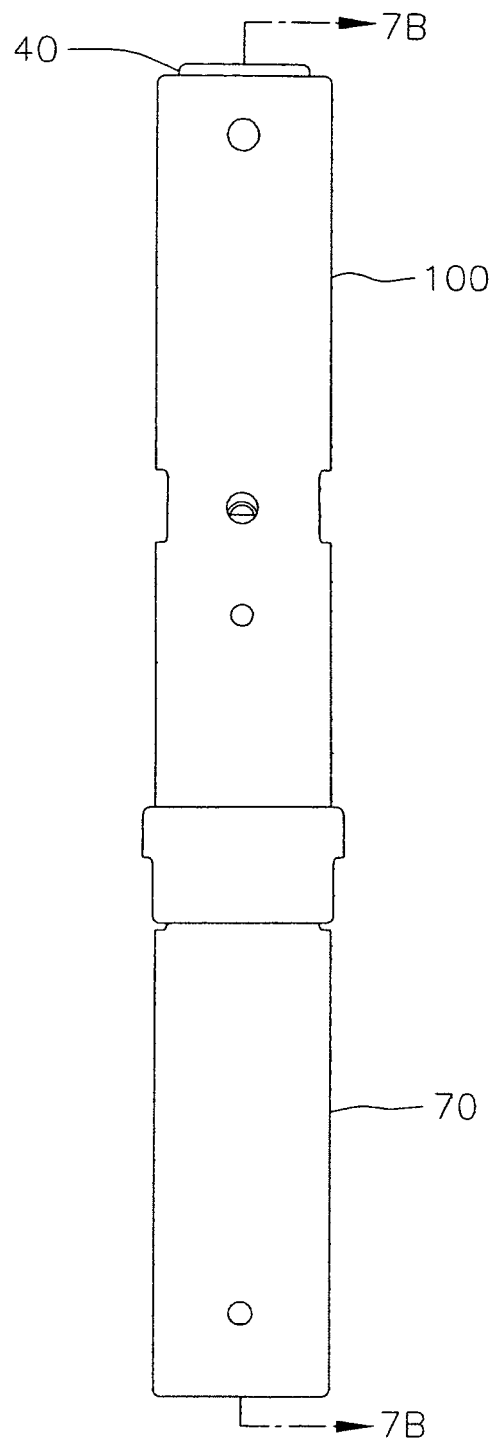
FIG. 7A is a side view of the pen injection device of FIG. 1, the pen injection device in a mixing position.
Figure 7B:
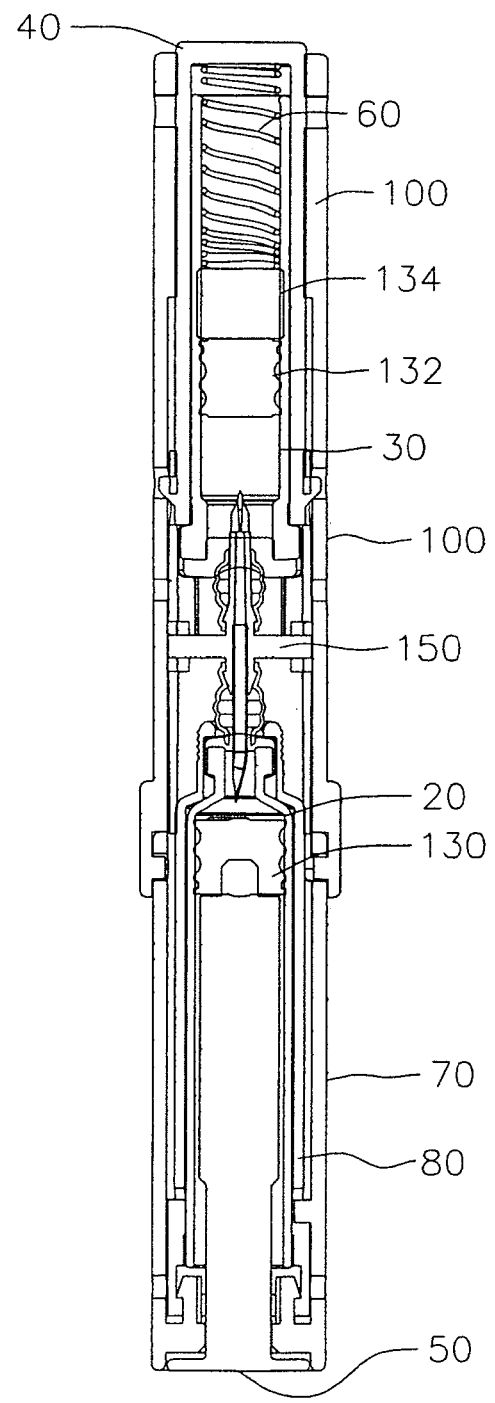
FIG. 7B is a side sectional view through the pen injection device of FIG. 1 taken at line 7B-7B, the pen injection device in a mixing position.

Task 420 includes translating the plunger rod of the pen injection device in a first direction from a first position at least once, as depicted, for example, in FIGS. 7A-B. This action transfers at least a portion of the first substance or the mixture of the first and second substances from one of the first and second containers to the other container to mix or further mix therein with the second substance as a result of the movement and associated turbulence. This mixing may be improved if task 420 is performed with the pen injection device in a vertical, or upright, position. After the plunger rod is depressed toward the first container, the biasing mechanism moves at least a portion of the second substance or the mixture to the first container. Task 420 may be repeated one or more times. For instance, task 420 may be repeated at least five times, or as determined to be sufficient, as further described below with respect to task 430, for example.

With respect to the embodiment of the pen injection device 10 described above, a user depresses the plunger rod 50 toward the second cartridge 30, transferring at least a portion of one of the first and second substances, or a mixture thereof, from the first cartridge 20 to the second cartridge 30. Subsequently, the biasing mechanism 60, which, in the present embodiment, is a compression spring, causes at least a portion of one of the substances, or a mixture thereof, to move from the second cartridge 30 to the first cartridge 20. In an alternative embodiment, a user pulls the plunger rod 50 in a direction away from the second cartridge 30 to facilitate mixing of the first and second substances, and the biasing mechanism 60 is a tension spring configured to bias the plunger rod 50 toward the second cartridge 30.

Task 430 includes viewing the first and second substances, or the mixture thereof, through at least one window of the pen injection device, such as at least one of the windows 112 of the outer housing 100 and/or one of the windows 90 of the first cartridge housing 70, and determining whether the first and second substances are sufficiently mixed (e.g., the mixture is clear and does not contain unmixed powder or clumps). If it is determined that the first and second substances have not been sufficiently mixed, task 420 may be repeated. Task 430 may then also be repeated, and so on until it is determined that the first and second substances have been sufficiently mixed.

In task 440, the second container is disconnected from the first container. The outer housing 100 of the pen injection device 10 may be disconnected from the first cartridge 20 at the first cartridge housing 70 by disconnecting the bayonet-style L-shaped slots 75 of the first cartridge housing 70 and the pins 106 of the outer housing 100, or by disconnecting an alternative connecting device, such as a threaded connection, of the pen injection device 10. Also, the second cartridge 30 and the activation member 40 may remain connected to the outer housing 100 and, as such, may be indirectly disconnected from the first cartridge 20 by disconnecting the outer housing 100 and the first cartridge 20. Also, in the present embodiment, the dual transfer spike assembly 150 remains in the outer housing 100, and one or both of the dual transfer spike assembly 150 and the outer housing 100 may include a feature configured to restrain the dual transfer spike assembly 150 from separating from the outer housing 100 during or following task 440. The one or more protrusions 114 of the outer housing 100 may be received, for example, by the one or more openings 164 of the dual transfer spike assembly 150. In the present embodiment, the plunger rod 50 remains connected to the first cartridge 20, as it is utilized in a later task for injecting a mixture of the first and second substances.

Task 450 includes connecting an injection needle, such as the injection needle 18, to the first container, e.g., the first cartridge 20, as shown in FIG. 5 with respect to the pen injection device 10. Alternatively, instead of the injection needle 18, any other mechanism for administering the mixture in the first container 20 to a subject may be connected to the first cartridge 20. The injection needle 18 or other administering mechanism may be connected to the first cartridge holder 80 by a threaded connection, a push-on connection, or any other suitable connecting or coupling device. Alternatively, the injection needle 18 or other administering mechanism may be connected directly to the first cartridge 20 or the first cartridge housing 70 by a threaded connection or other suitable connecting device.

Task 460 includes piercing a subject with the injection needle or other administering mechanism. The subject may be a person performing the method 400 of using a pen injection device, or another person. Alternatively, instead of self-administering or injecting the mixture into another person, the method 400 of using a pen injection device may be performed by injecting the mixture into an object, such as a training pad.

In task 470, the plunger rod is depressed toward the first container, thereby injecting a mixture of the first and second substances into the subject. As the plunger rod 50 is depressed, it pushes the mixture through the first cartridge 20 toward the first end 22 of the first cartridge 20, where the injection needle 18 is connected, after which the mixture moves through the injection needle 18 and enters the subject. It may be desirable to retain the injection needle in the subject for at least five seconds.

Although the present invention has been described in certain specific embodiments, many additional modifications and variations would be apparent to those skilled in the art. For example, the outer housing 100 or the first and second spikes 154, 156 (dual transfer spike) may have varying configurations or structures. Also, as another example, some of the tasks of the method 400 of using a pen injection device may be performed in a different order than the one described above and shown in FIG. 39. Furthermore, some of the tasks of the method 400 of using a pen injection device may be omitted, or additional tasks not described above may be included, without departing from the invention.

It is therefore to be understood that this invention may be practiced otherwise than as specifically described. Thus, the present embodiments of the invention should be considered in all respects as illustrative and not restrictive, the scope of the invention to be determined by the claims supported by this application and the claims' equivalents.

The invention claimed is:

1. A pen injection device comprising:
 a sterile dual transfer spike assembly comprising a dual transfer spike having a first open end and a second open end, the dual transfer spike defining a fluidic pathway extending through the dual transfer spike from the first end to the second end;
 a first cartridge assembly comprising a first cartridge housing, and a first cartridge containing a first substance inside the first cartridge housing;
 a second cartridge assembly comprising a second cartridge housing, and a second cartridge containing a second substance inside the second cartridge housing, wherein the second cartridge housing is movable relative to the first cartridge housing from a first position wherein the first and second cartridges are not in fluid communication through the dual transfer spike to a second position wherein the first and second cartridges are in fluid communication through the dual transfer spike;
 a plunger rod in the first cartridge, translatable in a first direction to transfer at least a portion of the first and second substances from one of the first and second cartridges to the other of the first and second cartridges via the fluidic pathway between the first cartridge and the second cartridge; and
 a biasing mechanism configured to bias the plunger rod in a second direction opposite the first direction upon release of the plunger rod after said plunger rod has been translated in said first direction, in order to transfer at least a portion of the first and second substances from the other of the first and second cartridges to the one of the first and second cartridges.

2. The pen injection device of claim 1 wherein the dual transfer spike assembly further comprises a first separating member located at the first end of the dual transfer spike and pierceable by the first end of the dual transfer spike, and a second separating member located at the second end of the dual transfer spike and pierceable by the second end of the dual transfer spike.

3. The pen injection device of claim 2 wherein the first separating member is pierceable by the first end of the dual transfer spike only after the second separating member is pierced by the second end of the dual transfer spike.

4. The pen injection device of claim 3 wherein the first substance comprises a diluent, and the second substance comprises a powder.

5. The pen injection device of claim 2 wherein the first separating member of the dual transfer spike assembly comprises a first sheath surrounding the first end of the dual transfer spike, and the second separating member of the dual transfer spike assembly comprises a second sheath surrounding the second end of the dual transfer spike.

6. The pen injection device of claim 5 wherein one of the first and second ends of the dual transfer spike comprises a Huber-style point.

7. The pen injection device of claim 2 wherein the dual transfer spike assembly further comprises at least one vent opening for venting air from at least one of the first and second cartridges.

8. The pen injection device of claim 7 wherein one of the first and second separating members is pierceable by the dual transfer spike only after the other of the first and second separating members is pierced by the dual transfer spike and one of the first and second cartridges is vented.

9. The pen injection device of claim 1 further comprising an outer housing comprising a first end receiving the first cartridge assembly, and a second end receiving the second cartridge assembly, wherein the dual transfer spike assembly is slidable in the outer housing between the first cartridge assembly and the second cartridge assembly.

10. The pen injection device of claim 9 wherein the first cartridge housing is removably coupled to the outer housing.

11. The pen injection device of claim 10 wherein the dual transfer spike assembly is retained in the outer housing when the first cartridge housing and the outer housing are uncoupled.

12. The pen injection device of claim 2 wherein the dual transfer spike assembly further comprises a collapsible housing surrounding the dual transfer spike.

13. The pen injection device of claim 12 wherein the first separating member of the dual transfer spike assembly comprises a first end of the collapsible housing, and the second separating member of the dual transfer spike assembly comprises a second end of the collapsible housing.

14. The pen injection device of claim 12 wherein the first separating member of the dual transfer spike assembly comprises a first sheath surrounding the first end of the dual transfer spike, and the second separating member of the dual transfer spike assembly comprises a second sheath surrounding the second end of the dual transfer spike.

15. The pen injection device of claim 1 wherein the first cartridge housing is removably coupled to the second cartridge housing.

16. The pen injection device of claim 1 wherein the first cartridge assembly further comprises a first cartridge holder receiving the first cartridge therein, the first cartridge holder is received in the first cartridge housing, and the first cartridge holder is interlocked with the first cartridge housing and not axially movable relative to the first cartridge housing when the second cartridge housing is in the second position.

17. The pen injection device of claim 1 wherein the second cartridge housing is slidable in the outer housing.

18. The pen injection device of claim 1 wherein the second cartridge housing is rotatable relative to the first cartridge housing from the first position to the second position.

19. The pen injection device of claim 1 wherein the fluidic pathway of the dual transfer spike and contents of the first and second cartridges are sterile before the first and second cartridges are in fluid communication through the dual transfer spike.

20. The pen injection device of claim 1 wherein the plunger rod is not translatable in the first direction and is substantially inside the first cartridge housing when the second cartridge housing is in the first position, and the plunger rod protrudes from the first cartridge housing and is translatable in the first direction when the second cartridge housing is in the second position.

* * * * *